US006420345B1

(12) United States Patent
Patel et al.

(10) Patent No.: US 6,420,345 B1
(45) Date of Patent: Jul. 16, 2002

(54) METHODS AND REAGENTS FOR INHIBITING ANGIOGENESIS

(75) Inventors: Salil Patel, Cupertino; James McArthur, San Carlos, both of CA (US); Jeno Gyuris, Winchester, MA (US)

(73) Assignees: Cell Genesys, Inc., Foster City, CA (US); GPC Biotech Inc., Waltham, MA (US)

( * ) Notice: Subject to any disclaimer, the term of this patent is extended or adjusted under 35 U.S.C. 154(b) by 0 days.

(21) Appl. No.: 09/457,646

(22) Filed: Dec. 9, 1999

Related U.S. Application Data
(60) Provisional application No. 60/122,974, filed on Mar. 1, 1999, and provisional application No. 60/163,382, filed on Nov. 5, 1999.

(51) Int. Cl.[7] .................. A61K 48/00; A61K 35/00; A61K 35/70; C12N 15/00; C12N 15/63; C12N 15/86; C07H 21/02; C07H 21/04

(52) U.S. Cl. ............... 514/44; 424/93.1; 424/93.21; 435/440; 435/455; 435/475; 435/476; 435/320.1; 536/23.1

(58) Field of Search .................. 514/44; 424/93.1, 424/93.2; 435/320.1, 440, 455, 475, 476; 536/23.5

(56) References Cited

U.S. PATENT DOCUMENTS

| | | | |
|---|---|---|---|
| 4,994,443 A | | 2/1991 | Folkman et al. .............. 514/56 |
| 5,672,508 A | * | 9/1997 | Gyuris et al. ............ 435/320.1 |
| 5,733,876 A | | 3/1998 | O'Reilly et al. .............. 514/12 |
| 5,854,205 A | | 12/1998 | O'Reilly et al. ................ 514/2 |
| 6,177,272 B1 | * | 1/2001 | Nabel et al. ............. 435/320.1 |

FOREIGN PATENT DOCUMENTS

| | | | |
|---|---|---|---|
| JP | 10-52285 | | 2/1998 |
| WO | WO-97/03635 | * | 2/1997 |
| WO | 9727297 | | 7/1997 |
| WO | 9903508 | | 1/1999 |
| WO | WO99/06540 | | 2/1999 |

OTHER PUBLICATIONS

A Vidal et al., Elsevier, "Cell–cycle inhibitors: three families united by a common cause," Review, 2000, 247:1–15.*

Folkman, J. et al., The Journal of Biological Chemistry, vol. 267, No. 16, Jun. 1992, "Angiogenesi", pp. 10931–10934.

Robertson, E.S. et al., Proc. Natl. Acad. Sci. USA, vol. 93, Oct. 1996, "Epstein–Barr virus vectors for gene delivery of B lymphocytes"; pp. 11334–11340.

Zheng, L. et al., Aids Research and Human Retroviruses, vol. 15, No. 11, 1999, "Delivery of Liposome–Encapsulated HIV Type I Proteins to Human Dendritic Cells for Stimulation of HIV Type 1–Specific Memory Cytotoxic T Lymphocyte Responses", pp. 1011–1020.

Villaschi, S. et al., American Journal of Pathology, vol. 143, No. 1, Jul. 1993, "Angiogenic Role of Endogenous Basic Fibroblast Growth Factor Released by Rat Aorta After Injury"; pp. 181–190.

Fang, B. et al., Analytical Biochemistry 254 (1997), Article No. AB972417, "A Packaging System for SV40 Vectors without Viral Coding Sequences", pp. 139–143.

(List continued on next page.)

*Primary Examiner*—James Ketter
*Assistant Examiner*—Q. Janice Li
(74) *Attorney, Agent, or Firm*—Roylance, Abrams, Berdo & Goodman, L.L.P.

(57) ABSTRACT

Disclosed are methods for inhibiting angiogenesis using cyclin dependent kinase inhibitors (CDKi) and fusion proteins thereof, recombinant viruses comprising transgenes and nucleic acid sequences encoding the same, and liposomes carrying the same as angiogenesis-inhibiting reagents.

21 Claims, 18 Drawing Sheets

OTHER PUBLICATIONS

Risau, W. et al., Annu. Rev. Cell Dev. Biol. 1995, 11, "Vasculogenesis", pp. 73–91.
Aiello, L. P., Current Opinion in Opthalmology 1997, 8, "Clinical implications in vascular growth factors in proliferative retinopathies", pp. 19–31.
Glorioso, J. C. et al., Annu. Rev. Microbiol. 1995, 49, "Development and Application of Herpes Simplex Virus Vectors for Human Gene Therapy", pp. 675–710.
Finer, M.H. et al., Blood, vol. 83, No. 1 (Jan. 1, 1994), "kat: A High–Efficiency Retroviral Transduction System for Primary Human T. Lymphocytes", pp.43–50.
Spaete, R.R. et al., Cell, vol. 40, Aug. 1982, "The Herpes Simplex Virus Amplicon: A New Eucaryotic Defective–Virus Cloning–Amplifying Vector", pp. 295–304.
Cullen, B.R., Cell, vol. 46, Sep. 26, 1986, "Trans–Activation of Human Immunodeficiency Virus Occurs via a Bimodal Mechanism", pp. 973–982.
Romeo, C. et al., Cell, vol. 68, Mar. 6, 1992, "Sequence Requirements for Induction of Cytolysis by the T Cell Antigen/Fc Receptor Cell ζ Chain", pp. 889–897.
Kolanus, W. et al., Cell, vol. 74, Jul. 16, 1993, "T Cell Activation by Clustered Tyrosine Kinases", pp. 171–183.
Selzman, C.H. et al., Cir, Res. 1999; 84, "Liposomal Delivery of Purified Inhibitoryκ–Bα–Inhibits Tumor Necrosis Factor–α–Induced Human Vascular Smooth Muscle Proliferation", pp. 867–875.
Healy, D.L., et al., Human Reproduction Update, 1998, vol. 4, No. 5, "Angiogenesis: a new theory for endometriosis", pp. 736–740.
Nicosia R.F. et al., In Vitro Cell. Dev. Biol, Feb. 26, 1990. "Modulation of Microvascular Growth and Morphogenesis by Reconstituted Basement Membrane Gel In Three–Dimensional Cultures of Rat Aorta: A Comparative Study of Angiogenesis in Matrigel, Collagen, Fibrin and Plasma Clot"; pp. 119–128.
Samulski, R. J. et al., Journal of Virology, Sep. 1989, "Helper–Free Stocks of Recombinant Adeno–Associated Viruses: Normal Integration Does Not Require Viral Gene Expression", pp. 3822–3828.
Perkus, M.E. et al., Journal of Virology, Sep. 1989, "Cloning and Expression of Foreign Genes in Vaccinia Virus, Using Host Range Selection System", pp. 3829–3836.
Shimizu, N. et al., "Journal of Virology, Oct. 1996, "Clonal Propagation of Epstein–Barr Virus (EBV) Recombinants in EBV–Negative Akata Cells, pp. 7260–7263.
Fong, S.E. et al., Journal of Virological Methods 66 (1997), "Cationic liposome–mediated uptake of human immunodeficiency virus type 1 Tat protein into cells", pp. 149–157.
Weidner, M.D., N. et al., The New England Journal of Medicine, vol. 324, No. 1, Jan. 23, 1991, "Tumor Angiogenesis and Metastasis–Correlation in Invasive Breast Carcinoma", pp. 1–8.
Risau, W. Nature, vol. 386, Apr. 17, 1997, "Mechanisms of angiogenesis", pp. 671–674.
Abulafia, M.D., O. et al. Obstetrics & Gynecology, 1999, 94, "Angiogenesis of the endometrium", pp. 148–153.
Mouritsen, O.G. et al., Pharmaceutical Research, vol. 15, No. 10, 1998, "A New Look at Lipid–Membrane Structure in Relation to Drug Research", pp. 1507–1519.
Blaise, A. et al., Biochemical and Biophysical Research Communications 247 (1998), Article No. RC988497, "Structure of the Gene Encoding the Human Cyclin–Dependent Kinase Inhibitor p18 and Mutational Analysis in Breast Cancer", pp. 146–153.
Jen, J. et al., Cancer Research 54, Dec. 15, 1994, "Deletion of p16 and p15 Genes in Brain Tumors", pp. 6353–6358.
Fawell, S. et al., Proc. Natl. Acad. Sci USA, vol. 91, Jan. 1994, "Tat–mediated delivery of heterologous proteins of cells", pp. 664–668.
Gyuris, J. et al. Cell,vol. 75, Nov. 19, 1993, "Cdi1, a Human G1 and S Phase Protein Phosphatase That Associates with Cdk2", pp. 791–803.
Harper, J. W. et al., Cell, vol. 75, Nov. 19, 1993, "The p21 Cdk–Interacting Protein Cip1 Is a Potent Inhibitor of G1 Cyclin–Dependent Kinases", pp. 805–816.
Polyak, K. et al., Cell, vol. 78, Jul. 15, 1994, "Cloning of p27$^{kip1}$, a Cyclin Dependent Kinase Inhibitor and a Potential Mediator of Extracellular Antimitogenic Signals", pp. 59–66.
Nomura, H. et al., Gene 191 (1997), "Cloning and characterization of rat p27$^{Kip1}$, a cyclin–dependent kinase inhibitor", pp. 211–218.
Lee, M.H. et al., Genes & Development 9, 1995, "Cloning of p57$^{kip2}$, a cyclin–dependent kinase inhibitor with unique domain structure and tissue distribution", pp. 639–649.
Matsuoka, S. et al., Genes & Development 9, 1995, "p57$^{kip2}$, a structurally distinct member of the p21$^{CIP1}$ Cdk inhibitor family, is a candidate tumor suppressor gene", pp. 650–662.
Graham, F.L. et al., J. gen. Virol. 36 (1997), "Characteristics of a Human Cell Line Transformed by DNA from Human Adenovirus Type 5", pp. 59–72.
Guan, K.L. et al., Molecular Biology of the Cell, vol. 7, Jan. 1996, "Isolation and Characterization of p19$^{INK4d}$, a p16–related Inhibitor Specific to CDK6 and CDK4", pp. 57–70.
Serrano, M. et al., Nature, vol. 366, Dec. 16, 1993, "A new regulatory motif in cell–cycle control causing specific inhibition of cyclin D/CDK4", pp. 704–707.
Russo, A.A., et al., Nature, vol. 395, Sep. 17, 1998, "Structural basis for inhibition of the cyclin–dependent kinase Cdk6 by the tumour suppressor p16$^{INK4a}$", pp. 237–242.
Okamoto, A. et al., Proc. Natl. Acad. Sci. USA, vol. 91, Nov. 1994, "Mutations and altered expression of p16$^{INK4}$ in human cancer", pp. 11045–11049.
Yang, Z.Y. et al., Proc. Natl. Acad. Sci. USA, vol. 98, Jul. 1996, "Role of p21 cyclin–dependent kinase inhibitor in limiting intimal cell proliferation in responses to arterial injury", pp. 7905–7910.
Zhang, S. et al., Proc. Natl. Acad. Sci. USA. vol. 95, Mar. 1998, "Cdkn2a, the cyclin–dependent kinase inhibitor encoding a p16$^{INK4a}$ and p19$^{ARF}$, is a candidate for the plasmacytoma susceptibility locus, Pctr1", pp. 2429–2434.
Jackson, C.J. et al., Ann Rheum Dis, 57(3), 1988, "Rheumatoid synovial endothelial cells secrete decreased levels of tissue inhibitor of MMP (TIMP1)", pp. 158–161.
Pierce, M.D., E.A. et al., Int. Ophth. Clinics 34, 1994, "Controversies in the Management of Retinopathy of Prematurity", pp. 121–148.
*Proc. Amer. Assn. Cancer Res.* vol. 40 p. 630, (1999). McArthur et al. "Cancer Gene Therapy with a Novel Chimeric p27/p/16 Tumor Suppressor Gene."
*J. Amer. Col. Cardiol.* vol. 33, No. 2, Suppl. A, pp. 250A–251A, (1999). Sun et al. "Rapamycin Inhibits Vascular Endothelial Cell Proliferation via Induction of a Cyclin–Dependent Kinase Inhibitor."
*Biochem. Biophys. Res. Com.* vol. 220, pp. 703–709, (1996). Kwon et al. "The cdk2 Binding Domain of the p27$^{kip}$ Correlates with the Inhibition of the Kinase Activity of cdk2/Cyclin Complexes."

* cited by examiner

| | | CDK4/ cyclin D1 (nM) | CDK2/ cyclin E (nM) | CDC2/ cyclin B (nM) | HALF-LIFE (HRS) | |
|---|---|---|---|---|---|---|
| | | | | | $G_0$ | As |
| p16 | 1 — 156 | 100 | >1000 | >1000 | ~3 | ~3 |
| p27 | 1 — 198 | 23 | 2.4 | 12 | ~3 | ~4.5 |
| Δp27 12-178 | 12 — 178 | 52 | 11 | 44 | <2 | <1 |
| Δp27 25-93 | 25 — 93 | 30 | 8.3 | 31 | <1 | <1 |
| W3 | 1 — 198 2 — 156 | 17 | 3.0 | 18 | ~2.5 | ~6.5 |
| W4 | 1 — 198/2 — 156 | 39 | 8.9 | 15 | | |
| W5 | 1 — 156 2 — 198 | 44 | 11 | 18 | | |
| W6 | 1 — 156/2 — 198 | 26 | 8.4 | 17 | | |
| W8 | 12 — 178 2 — 156 | 23 | 4.4 | 17 | | |
| W7 | 12 — 178/2 — 156 | 16 | 2.6 | 9.2 | ~3 | ~20 |
| W10 | 25 — 93 2 — 156 | 38 | 3.0 | 17 | | |
| W9 | 25 — 93/2 — 156 | 47 | 3.5 | 18 | ~2 | ~4.5 |
| p27 + p16 | 1 — 156  1 — 198 | 25 | 1.7 | 12 | | |

FIG. 6

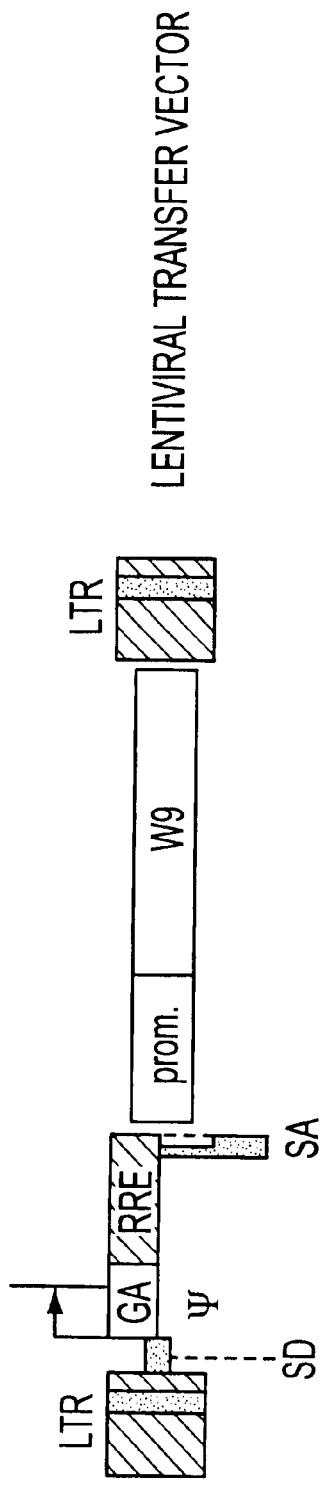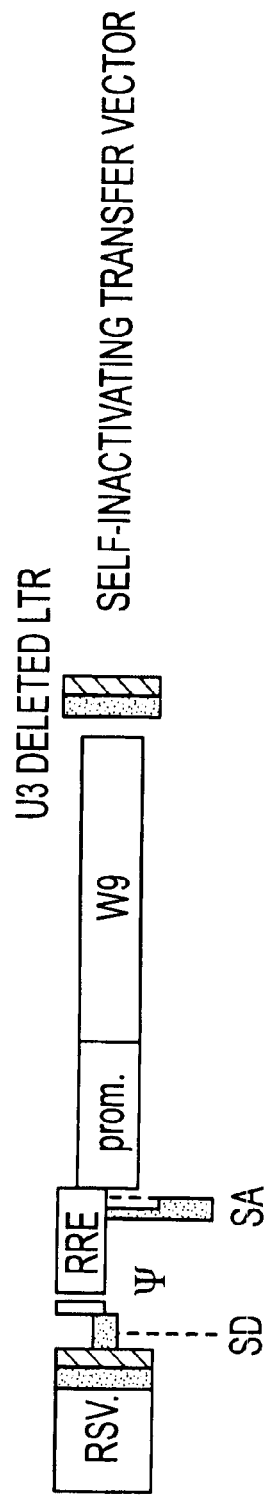
FIG. 14A
FIG. 14B

METHODS AND REAGENTS FOR INHIBITING ANGIOGENESIS

This application claims benefit of U.S. Ser. No. 60/122,974 filed Mar. 1, 1999 and of U.S. Ser. No. 60/163,382 filed Nov. 5, 1999.

BACKGROUND OF THE INVENTION

1. Field of the Invention

This invention relates to the inhibition of angiogenesis, particularly the inhibition of angiogenesis in angiogenesis-associated conditions including, without limitation, neoplasia, rheumatoid arthritis, endometriosis, psoriasis, and vascular retinopathies.

2. Summary of the Related Art

The process of angiogenesis results in the formation of new blood vessels. During the process of angiogenesis, endothelial cells which exist in a quiescent state as part of an existing blood vessel grow and enter a migratory, proliferative state. This migratory, proliferative state of endothelial cells undergoing angiogenesis is eventually resolved when the cells return to the quiescent state as part of a functional new blood vessel. The process of angiogenesis is orchestrated by a complex network of multiple macromolecular interactions. Some essential angiogenic factors include fibroblast growth factor-basic (bFGF), vascular endothelial growth factor (VEGF), the Angiopoietins (Ang -½/3/4), cytokines, extracellular matrix (ECM) proteins, and matrix metalloproteases (MMP). These factors are produced locally by stromal cells (e.g., smooth muscle cells, pericytes, fibroblasts) and by activated leukocytes that are recruited to the area (Risau, W. (1997) *Nature* 386(6626):671–674; Risau and Flamme (1995) *Ann. Rev. Cell Dev. Biol.* 11:73–91).

The interplay of growth factors (e.g., VEGF and Ang-2) and surface protein-ECM interactions (e.g., αvβ3/5 interactions with both collagen and matrix metalloprotease-2) drive the process of angiogenesis through a predictable sequence of events. Activation of endothelial cells by pro-angiogenic stimuli results in vasodilation, hyperpermeability, and local release of proteases which degrade the basement membrane and ECM. This allows the formation of a provisional fibrin matrix, which provides a primary scaffold for the assembly of early microvessels. Motogenic endothelial cells sprout into the matrix and migrate with controlled matrix degradation at the tip. Proliferation occurs proximal to migration with formation of a primitive tube. Extensive remodeling ensues until the new capillary matures and anastomoses (i.e., fuses and joins) with other sprouts (Risau, W. (1997) *Nature* 386(6626):671–674; Risau and Flamme (1995) *Ann. Rev. Cell Dev. Biol.* 11:73–91).

Angiogenesis is stimulated and harnessed by some neoplasms (e.g., tumors) to increase nutrient uptake. However, in contrast to normal angiogenesis, which leads to anastomoses and capillary maturation, angiogenesis associated with neoplasia is a continuous process. Endothelial cells are activated by nearby neoplastic cells to secrete not only VEGF which stimulates angiogenesis, but also matrix metalloproteases (MMP) which degrade the surrounding extracellular matrix. The endothelial cells then invade the extracellular matrix where they proliferate, migrate, and organize to form new blood vessels, which support neoplasm growth and survival.

The newly vascularized neoplasm continues to grow, leading to further nutrient deprivation and chronic pro-angiogenic signaling. The vasculature of neoplasms is characterized by the presence of lacunae and a low rate of anastomosis. This partially dysfunctional vasculature fuels the permanent requirement for angiogenesis. Additionally, this incomplete vasculature allows the shedding of neoplastic cells into the systemic circulation. Hence, the angiogenic potential of a neoplasm correlates with metastatic potential (Weidner et al. (1991) *N. Engl. J. Med.* 324(1):1–8; Folkman and Shing (1992) *J. Biol. Chem.* 267(16):10931–10934). As a significant proportion of neoplasms are dependent on continued angiogenesis, inhibition of angiogenesis blocks neoplasm growth which often leads to complete necrosis of the neoplasm. (Weidner et al. (1991) *N. Engl. J. Med.* 324(1):1–8; Folkman and Shing (1992) *J. Biol. Chem.* 267(16):10931–10934). Thus, methods or reagents for inhibiting angiogenesis associated with neoplasia could represent a viable anti-neoplasia therapy.

Other disease conditions are characterized by aberrant levels of angiogenesis. For example, rheumatoid arthritis (RA) is an inflammatory disease associated with intense angiogenesis (see, e.g., Jackson et al. (1988) *Ann. Rheum. Dis.* 57(3):158–161). Another angiogenesis-associated condition is psoriasis, a chronic skin disorder that affects one in fifty people world wide and over five million people in the United States. The most common form of the disease is called plaque psoriasis or psoriasis vulgaris. Other forms are pustular, guttate, inverse, and erythrodermic psoriasis.

Yet another angiogenesis-associated condition is vascular retinopathy, which includes diabetic retinopathy, retinal vein occlusion, retinopathy of prematurity (ROP), exudative age-related macular degeneration, sickle cell retinopathy, and radiation retinopathy (see, e.g., Aiello, L. P. (1997) *Curr. Opin. Ophthalmol.* 8(3):19–31; Pierce et al. (1994) *Int. Ophth. Clinics* 34:121–148). An additional angiogenesis-associated condition is endometriosis (see, e.g., Abulafia and Sherer (1999) *Obstet. Gynecol.* 94(1):148–153; Healy (1998) *Hum. Reprod. Update* 4(5):736–740). Thus, there exists a need to control angiogenesis as a means for treating and/or alleviating the symptoms of angiogenesis-associated conditions.

There are a number of known reagents that inhibit angiogenesis that have been used for various conditions associated with angiogenesis. For example, O'Reilly et al. teach that isolated endostatin protein is allegedly an inhibitor of endothelial cell proliferation and angiogenesis (O'Reilly et al., U.S. Pat. No. 5,854,205). Another compound with alleged anti-angiogenesis activity is heparin or heparin fragments (Folkman et al., U.S. Pat. No. 4,994,443). O'Reilly et al. also teach that angiostatin can allegedly reversibly inhibit proliferation of endothelial cells (O'Reilly et al., U.S. Pat. No. 5,733,876). However, many of the known anti-angiogenesis reagents and therapies have limitations. For example, for ROP, a common cause of blindness in children, two therapeutic methods, cryotherapy and laser therapy, are not completely effective and themselves cause damage to the eye, resulting in a reduction of vision (Pierce et al. (1994) *Int. Ophth. Clinics* 34:121–148).

Therefore, there still exists a need for improved reagents that reduce angiogenesis while overcoming the shortcomings of known reagents for inhibiting angiogenesis. Such novel reagents and methods for using them are useful for treating conditions associated with angiogenesis including, without limitation, neoplasia, rheumatoid arthritis, endometriosis, psoriasis, and vascular retinopathies.

BRIEF SUMMARY OF THE INVENTION

The invention provides methods and reagents for inhibiting angiogenesis and allows for the treatment of various angiogenesis-associated conditions.

It has been discovered that cyclin dependent kinase inhibitors (CDKi's) can inhibit angiogenesis. This discovery has been exploited to develop the present invention which includes methods and compositions for inhibiting angiogenesis.

In a first aspect, the invention provides a method for inhibiting angiogenesis comprising introducing into a target endothelial cell an effective amount of a recombinant virus that comprises a transgene encoding a cyclin dependent kinase inhibitor (CDKi), wherein proliferation and/or migration of the endothelial cell is inhibited. In a certain preferred embodiment, the cyclin dependent kinase inhibitor is derived from a mammal (e.g., a human). In a certain embodiment, the cyclin dependent kinase inhibitor is a protein from the CIP/KIP family or an active fragment thereof, such as an active fragment selected from the group consisting of amino acids 25–93 of human p27 protein (SEQ ID NO:26) and amino acids 12–178 of human p27 protein. In a certain embodiment, the cyclin dependent kinase inhibitor is a protein from the INK4 family or an active fragment thereof, such as human p1116 protein (SEQ ID NO:28) or an active fragment thereof. In a certain embodiment, the transgene encodes a cyclin dependent kinase inhibitor which can be internalized by a cell. In certain embodiments, the cyclin dependent kinase inhibitor is secretable.

In a certain preferred embodiment, the transgene encodes a cyclin dependent kinase inhibitor which is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the active fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p1 16. In some embodiments, the cyclin dependent kinase inhibitor is a fusion protein comprising at least an active fragment of human p16 and at least an active fragment of human p27, and is W3 (SEQ ID NO:4), W4 (SEQ ID NO:6), W5 (SEQ ID NO:8), W6 (SEQ ID NO:10), W7 (SEQ ID NO:14), W8 (SEQ ID NO:16), W9 (SEQ ID NO:20), or W10 (SEQ ID NO:22). In preferred embodiments, the cyclin dependent kinase inhibitor is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

In a preferred embodiment, the recombinant virus is an adenovirus, a lentivirus, a retrovirus, an SV-40 virus, an Epstein Barr virus, a herpesvirus, an adeno-associated virus, or a pox virus, such as a vaccinia virus. In a certain embodiment, the adenovirus lacks an essential viral protein-encoding sequence. In a certain embodiment, the adenovirus is replication-deficient. In one embodiment, the replication-deficient recombinant virus lacks a functional E1 region. In a certain embodiment, the adenovirus lacking the functional E1 region additionally lacks a functional second region, such as an E2 region, an E3 region, or an E4 region.

In a certain embodiment of the first aspect of the invention, the endothelial cell is in a mammal. In a certain embodiment, the mammal is afflicted with a condition associated with angiogenesis, which causes proliferation and/or migration of endothelial cells. In certain embodiments, the condition is neoplasia, rheumatoid arthritis, psoriasis, vascular retinopathy, or endometriosis. In one embodiment, the condition is neoplasia. In the case of neoplasia, the angiogenesis is stimulated by factors produced by a tumor.

In a second aspect, the invention provides a method for inhibiting angiogenesis comprising contacting an endothelial cell with an effective amount of a liposome that comprises a transgene encoding a mammalian cyclin dependent kinase inhibitor, wherein the transgene is internalized by the endothelial cell, wherein proliferation and/or migration of the contacted endothelial cell is inhibited. In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof.

In a certain embodiment of the second aspect of the invention, the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the active fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In some embodiments, the cyclin dependent kinase inhibitor is a fusion protein comprising at least an active fragment of human p16 and at least an active fragment of human p27, and is W7 or W9.

In certain embodiments of the second aspect of the invention, the liposome contains on its external surface a molecule that binds to a cell surface protein on the endothelial cell, wherein binding of the molecule to the cell surface protein facilitates the internalization. In some embodiments, the cyclin dependent kinase inhibitor is internalizable. In certain embodiments, the internalizable cyclin dependent kinase inhibitor is secretable.

In a third aspect, the invention provides a method for inhibiting angiogenesis, comprising contacting a target endothelial cell with a mammalian internalizable cyclin dependent kinase inhibitor, wherein proliferation and/or migration of the target endothelial cell is inhibited, and wherein the inhibitor is selected from the group consisting of a protein from the INK4 family or an active fragment thereof, a protein from the CIP/KIP family or an active fragment thereof, and a fusion protein comprising at least an active fragment of the protein from the INK4 family and at least an active fragment of the protein from the CIP/KIP family. In some embodiments, the active fragment of the protein from the CIP/KIP family is amino acids 25–93 of human p27 protein or amino acids 12–178 of human p27 protein. In one embodiment, the cyclin dependent kinase inhibitor is W7 or W9. In a preferred embodiment, the cell internalizes the cyclin dependent kinase inhibitor. In certain embodiments, the method further comprises delivering a transgene encoding the cyclin dependent kinase inhibitor to an auxiliary cell, wherein the transgene is expressed by the auxiliary cell to produce the cyclin dependent kinase inhibitor, wherein the auxiliary cell releases the cyclin dependent kinase inhibitor into the blood and wherein the bloodborne cyclin dependent kinase inhibitor contacts the target endothelial cell. In a certain embodiment, the cyclin dependent kinase inhibitor comprises a secretable segment and the auxiliary cell releases the cyclin dependent kinase inhibitor by secretion.

In a fourth aspect, the invention provides a purified internalizable form of a cyclin dependent kinase inhibitor. In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. In a certain preferred embodiment, the cyclin dependent kinase inhibitor is derived from a mammal (e.g., a human).

In a certain embodiment of the fourth aspect of the invention, the purified internalizable form of the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the active fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In some embodiments, the cyclin dependent kinase inhibitor is a fusion protein comprising at least an active fragment of human p16 and at least an active fragment of human p27, and is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

In a fifth aspect, the invention provides a method for treating a condition associated with angiogenesis. In this method, a therapeutically effective amount of a therapeutic composition comprising a purified internalizable form of a cyclin dependent kinase inhibitor and a pharmaceutically acceptable carrier is administered to a patient having or suspected of having the condition.

In a sixth aspect, the invention provides a method for treating a condition associated with angiogenesis wherein a therapeutically effective amount of a recombinant virus comprising a transgene encoding a cyclin dependent kinase inhibitor is administered to a patient having or suspected of having the condition. In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. In a certain preferred embodiment, the cyclin dependent kinase inhibitor is a derived from a mammal (e.g., a human).

In a certain embodiment of the sixth aspect of the invention, the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In some embodiments, the cyclin dependent kinase inhibitor is a fusion protein comprising at least an active fragment of human p16 and at least an active fragment of human p27, and is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

In a particular embodiment of the sixth aspect of the invention, the recombinant virus is an adenovirus, a lentivirus, a retrovirus, an SV-40 virus, an Epstein Barr virus, a herpesvirus, an adeno-associated virus, or a pox virus, such as a vaccinia virus. In a certain embodiment, the adenovirus lacks an essential viral protein-encoding sequence. In a certain embodiment, the adenovirus is replication-deficient, preferably because it lacks a functional E1 region. In a certain embodiment, the adenovirus lacking the functional E1 region additionally lacks a functional second region, such as an E2 region, an E3 region, or an E4 region. In a certain embodiment, the recombinant virus expresses on its external surface a molecule that binds to a cell surface protein on the endothelial cell, wherein binding of the molecule to the cell surface protein facilitates the transduction of the endothelial cell by the recombinant virus.

In a seventh aspect, the invention provides a recombinant virus comprising a transgene encoding a cyclin dependent kinase inhibitor, wherein the recombinant virus is an adenovirus lacking an E1 region, a lentivirus, a retrovirus, an SV-40 virus, an Epstein Barr virus, a herpesvirus, an adeno-associated virus, or a pox virus, such as a vaccinia virus. In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. In a certain preferred embodiment, the cyclin dependent kinase inhibitor is a derived from a mammal (e.g., a human).

In a certain embodiment of the seventh aspect of the invention, the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In some embodiments, the cyclin dependent kinase inhibitor is a fusion protein comprising at least an active fragment of human p16 and at least an active fragment of human p27, and is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

In an eighth aspect, the invention provides a liposome comprising a cyclin dependent kinase inhibitor. In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. In a certain preferred embodiment, the cyclin dependent kinase inhibitor is a derived from a mammal (e.g., a human).

In a certain embodiment of the eighth aspect of the invention, the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In some embodiments, the cyclin dependent kinase inhibitor is a fusion protein comprising at least an active fragment of human p16 and at least an active fragment of human p27, and is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

In a ninth aspect, the invention provides a nucleic acid composition comprising a nucleic acid sequence encoding an internalizable form of a cyclin dependent kinase inhibitor, wherein the nucleic acid sequence is operably linked to a regulatory sequence which regulates cellular expression of the nucleic acid sequence. In one embodiment, the nucleic acid sequence encodes a secretion signal.

In a tenth aspect, the invention provides a therapeutic composition comprising a nucleic acid sequence encoding an internalizable form of a cyclin dependent kinase inhibitor, wherein the nucleic acid sequence is operably linked to a regulatory sequence which regulates cellular expression of the nucleic acid sequence, and a pharmaceutically acceptable carrier. In one embodiment, the therapeutic composition further comprises a delivery system that facilitates the internalization of the composition by an endothelial cell. In certain embodiments, the delivery system is a liposome comprising the nucleic acid composition. In certain embodiments, the delivery system is a recombinant virus comprising the nucleic acid composition. In preferred embodiments, the recombinant virus is an adenovirus, a retrovirus, an SV-40 virus, an Epstein Barr virus, a herpesvirus, an adeno-associated virus, or a pox virus. In one embodiment, the nucleic acid sequence also encodes a secretion signal.

In an eleventh aspect, the invention provides a method for treating a patient having or suspected of having a condition associated with angiogenesis comprising delivering a therapeutically effective amount of a transgene encoding a secretable, internalizable form of a cyclin dependent kinase inhibitor to cells of the patient that are in close proximity to endothelial cells affected by the condition. In one embodiment, the therapeutic composition further comprises a delivery system that facilitates the internalization of the composition by an endothelial cell. In certain embodiments, the delivery system is a liposome comprising the transgene. In certain embodiments, the delivery system is a recombinant virus comprising the transgene. In preferred embodiments, the recombinant virus is an adenovirus, a retrovirus, an SV-40 virus, an Epstein Barr virus, a herpesvirus, an adeno-associated virus, or a pox virus.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 14A is a schematic representation of a recombinant lentivirus vector, according to the invention, which contains a nucleic acid sequence encoding a non-limiting representative CDKi of the invention, W9, operably linked to regulatory sequences and flanked by HIV LTRs;

FIG. 14B is a schematic representation of a recombinant, self-inactivating lentiviral vector according to the invention, which contains a nucleic acid sequence encoding a non-limiting representative CDKi of the invention, W9, operably linked to regulatory sequences.

DETAILED DESCRIPTION OF THE PREFERRED EMBODIMENTS

Figure 1:
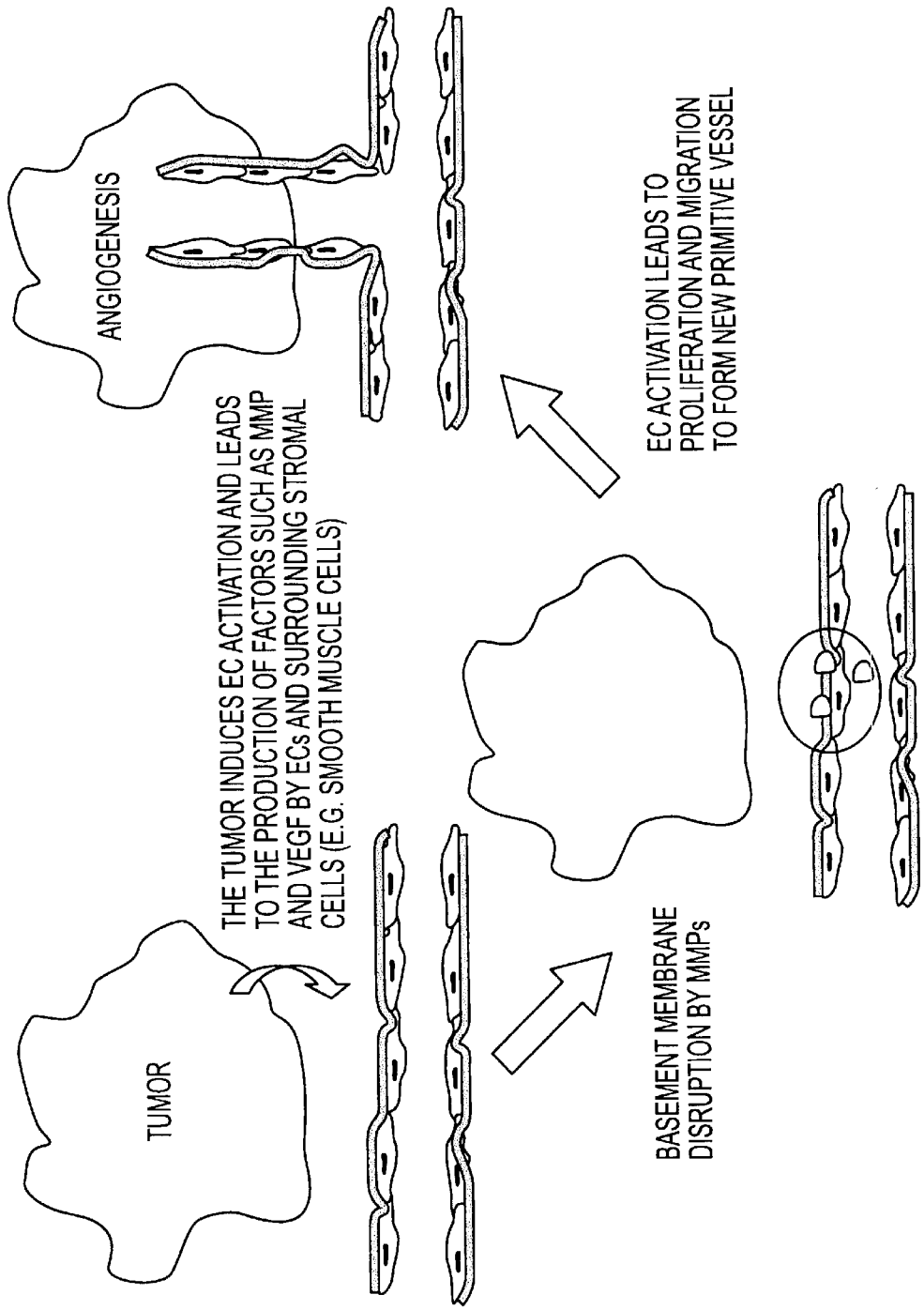
FIG. 1 is a diagrammatic representation showing the steps involved in tumor-induced angiogenesis. Endothelial cells and possibly smooth muscle cells are induced by nearby tumor cells to secrete VEGF and MMP. The endothelial cells then invade the extracellular matrix where they proliferate and organize to form new blood vessels.

The patent and scientific literature referred to herein establishes knowledge that is available to those with skill in the art. The issued patents, applications, and references, including GenBank database sequences, that are cited herein are hereby incorporated by reference to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The invention provides methods and compositions for inhibiting angiogenesis. In addition, therapeutic compositions for treating a condition associated with increased angiogenesis may be developed using the methods and reagents of the invention. Moreover, the process of angiogenesis can be better understood and studied using the methods and reagents of the invention. Thus, the reagents according to the invention are useful as analytical tools and as therapeutic tools, such as gene therapy tools. The invention also provides methods and compositions which may be manipulated and fine-tuned to fit the condition(s) to be treated.

Accordingly, in a first aspect, the invention provides a method for inhibiting angiogenesis comprising introducing into an endothelial cell an effective amount of a transgene encoding a cyclin dependent kinase inhibitor, wherein proliferation and/or migration of the endothelial cell is inhibited.

Cyclin dependent kinase inhibitors (CDKi's) are proteins which regulate the activity of cyclin-dependent kinase (CDK)/cyclin complexes which play a key role in the cell cycle. CDK/cyclin complexes are comprised of a catalytic kinase subunit (such as cdc2, CDK2, CDK4, or CDK6) with one of a variety of regulatory cyclin subunits (such as cyclin A, B1, B2, D1, D2, D3, or E) which results in the assembly of functionally distinct CDK/cyclin complexes.

Thus, in accordance with the invention, by "cyclin dependent kinase inhibitor (CDKi)" is meant any protein which inhibits and/or regulates a CDK/cyclin complex. The definition includes, without limitation, proteins from the CIP/KIP family of CDKi proteins which includes, without limitation, human p27$^{kip1}$ (GenBank Accession No. U10906, Polyak et al. (1994) Cell 78:56–66); murine p27$^{kip1}$ (GenBank Accession No. U09968, Polyak et al. (1994) Cell 78:56–66); rat p27$^{kip1}$ (GenBank Accession Nos. D86924 and D83792, Nomura et al. (1997) Gene 191(2):211–218); human p57$^{KIP2}$ (GenBank Accession No. NM_000076, Matsuoka et al. (1995) Genes Dev. 9(6):650–662); murine p57$^{KIP2}$ (GenBank Accession No. U20553, Lee et al. (1995) Genes Dev. 9(6):639–649); canine p21$^{Waf1/Cip1}$ (GenBank Accession No. AF076469); and human p21$^{Waf1/Cip1}$ (GenBank Accession No. L25610; Harper et al. (1993) Cell 75:806–816, 1993); as well as proteins from the INK4 family of CDKi proteins which includes, without limitation, human p18$^{CDKN2C}$ (GenBank Accession Nos. AF041248 and NM_001262, Blais et al. (1998) Biochem. Biophys. Res. Commun. 247(1):146–153); human Cdi1 (GenBank Accession No. NM_005192, Gyuris et al. (1993) Cell 75(4):791–803); human p19$^{INK4d}$ (GenBank Accession No. NM_001800, Guan et al. (1996) Mol. Biol. Cell 7(1):57–70); human p15 (GenBank Accession No. S75756, Jen et al. (1994) Cancer Res. 54(24):6353–6358); murine p15$^{INK4b}$ (GenBank Accession Nos. U80415, U79634, and U79639); murine p16$^{Ink4/MTS1}$ (GenBank Accession Nos. AF044336 and AF044335, Zhang et al. (1998) Proc. Natl. Acad. Sci. USA 95(5):2429–2434); and human p16$^{INK4}$ (GenBank Accession No. NM_000077; Serrano et al. (1993) Nature 366(6456):704–707 and Okamoto et al. (1994) Proc. Natl. Acad. Sci. USA 91(23):11045–11049). Exemplary CDKi's according to the invention are the fusion proteins described herein and described in PCT Publication No. WO99/06540, hereby incorporated by reference.

By "angiogenesis" is meant the growth of a new blood vessel in which the proliferation and/or migration of an endothelial cell is a key step. One non-limiting example of angiogenesis is schematically depicted in FIG. 1. By "inhibiting angiogenesis" is meant the inhibition of any of the steps of the process of angiogenesis that includes, without limitation, proliferation and/or migration of endothelial cells. By "an effective amount" is meant an amount of a CDKi of the invention, a gene encoding a CDKi, a recombinant virus comprising a transgene encoding a CDKi, a liposome carrying a CDKi or transgene encoding a CDKi, as appropriate, that, when introduced into endothelial cells, is effective and sufficient for inhibiting proliferation and/or migration of those cells. One of skill in the art will appreciate that such an effective amount may be readily determined by comparing the inhibition of proliferation and/or migration of endothelial cells into which has been introduced a CDKi, a transgene encoding a CDKi, a liposome carrying a transgene or CDKi, or a recombinant virus comprising a transgene encoding a CDKi, as compared to endothelial cells subjected to the same culture and/or in vivo conditions, but which have not received a CDKi, a transgene encoding a CDKi, a liposome carrying the CDKi or the transgene encoding a CDKi, or recombinant virus comprising the transgene according to the invention. Assays for measuring angiogenesis, and for measuring the inhibition of angiogenesis, are described below and include, without limitation, the matrigel tube assay and the aortic ring sprouting assay.

In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. By "active fragment" is meant a polypeptide that encompasses at least the amino acid sequence required for inhibition of the appropriate cyclin dependent kinase which is targeted by the indicated CDKi (e.g., for human p27, see, Russo et. al. (1998) Nature 395:237–243). In a preferred embodiment, the cyclin dependent kinase inhibitor is derived from a mammal (e.g., a human).

In a certain embodiment of the invention, angiogenesis is inhibited by transducing the cell with a recombinant virus that comprises a transgene encoding the cyclin dependent kinase inhibitor. By "transducing" is meant the introduction of exogenous nucleic acid into a cell using a recombinant virus. A recombinant virus is made by introducing appropriate viral vector sequences encoding a protein of interest into a packaging or complementing cell line. By "introducing" a nucleic acid into a cell is meant the introduction of exogenous nucleic acid into a cell by any means, including, without limitation, methods known in the art as transfection, transduction, infection, and transformation. For various techniques for manipulating mammalian cells, see Keown et al. (1990) *Meth. Enzymol.* 185:527–537.

By "transgene" is meant a nucleic acid sequence encoding a desired protein or polypeptide fragment operably linked to one or more regulatory sequences such that the nucleic acid sequence is transcribed and translated when the transgene is introduced into a cell. Transgenes typically comprise in the following order a promoter/enhancer, protein-encoding nucleic acid sequence, and polyA signal. A polycistronic transgene comprising two protein encoding nucleic acid sequences separated by an IRES sequence is also within this definition. By "regulatory sequence" is meant nucleic acid sequences, such as initiation signals, polyadenylation (polyA) signals, promoters, and enhancers which control expression of protein coding sequences with which they are operably linked. By "operably linked" is meant that the nucleic acid sequence encoding a protein of interest and transcriptional regulatory sequences are connected in such a way as to permit expression of the nucleic acid sequence when introduced into a cell. By "expression" of a nucleic acid sequence encoding a protein is meant expression of an mRNA leading to production of that protein. Where a cell is transduced with a recombinant virus containing a transgene encoding a CDKi, it will be understood that the "effective amount" of the CDKi is determined by transducing the cell with an appropriate multiplicity of infection of virus. For example, if the endothelial cell to be transduced is in vitro, standard techniques (e.g., FACS analysis) may be employed to determined the percentage of CDKi-expressing cells.

Any recombinant virus can be employed to deliver the transgene encoding CDKi of the invention. Preferably, the virus can transduce both dividing and non-dividing endothelial cells and confers to the transduced cell a high level of transgene expression. Thus, a variety of recombinant viruses may be engineered to encode and deliver the CDKi of the invention to endothelial cells to inhibit angiogenesis. For example, a CDKi of the invention may be packaged in a recombinant adenovirus, a recombinant lentivirus, a recombinant retrovirus, a recombinant adeno-associated virus (AAV), a recombinant herpesvirus, a recombinant SV-40 virus, an Epstein-Barr virus, or a recombinant pox virus, such as, but not limited to, a recombinant vaccinia virus. Preferably, the recombinant virus is an adenovirus. Preferably, the adenovirus is replication-deficient. By "replication-deficient" is meant a recombinant virus that is unable to replicate in a cell other than a packaging cell. This can be accomplished, for example, when a replication-deficient adenovirus lacks a functional E1 region.

In an embodiment in which the delivery virus is a recombinant adenovirus, the adenovirus may be of any isotype. In a certain embodiment, the adenovirus lacks an essential viral protein-encoding sequence. The CDKi-encoding sequences may be inserted into one of the sequences of the adenovirus genome whose removal is not lethal. One known sequence of the adenovirus genome that may be removed is the E1 region, which controls adenovirus replication. Other non-essential regions (or combinations thereof) may also be used (e.g., the CDKi-encoding transgene may be inserted into the E2, E3, and/or E4 regions). Promoter/enhancer sequences may be constitutively active (e.g., the CMV promoter or the EF1α promoter), cell-type specific (e.g., a promoter of a VEGF-receptor gene that is specifically expressed by endothelial cells such as the VEGF-R1(Flt-1) gene promoter (GenBank Accession No.E13256) or the VEGF-R2 (Flk-1) gene promoter (GenBank Accession No. AF035121), or inducible (e.g., the cytokine-stimulated inducible nitric oxide synthase (iNOS) gene promoter). Numerous promoter/enhancer sequences are well known and their sequences available, for example, in the GenBank database (National Center for Biotechnology Information, National Institutes of Health, Bethesda, Md.).

In a preferred embodiment, the adenovirus encoding the CDKi of the invention is replication-deficient, lacking a functional E1 region. One non-limiting way to make such a recombinant adenovirus expressing a CDKi protein is to replace the E1 region of a recombinant replication-deficient adenovirus type 5 (Ad5) vector with a CDKi-encoding transgene (e.g., a CDKi protein-encoding nucleic acid sequence operably linked to a CMV promoter/enhancer and an SV40 poly A signal). The recombinant vector is then packaged in 293 cells to produce infectious recombinant adenovirus particles.

The recombinant adenovirus encoding a CDKi of the invention may be used to transduce cells in vivo or in vitro. Such administration may be standardized by determining the multiplicity of infection (MOI) of the recombinant adenovirus, or by determining the actual number of viral particles based on the amount of viral DNA. Such standardization of viral particles is routine and is generally described in Phillipson et al., *Molecular Biology of Adenoviruses*, Virology Monograph, Springer Verlag, New York, N.Y., 1975.

Both amphotropic and ecotropic recombinant retroviral vectors that may be used to generate recombinant retroviral particles have been described in the art. Accordingly, a nucleic acid sequence encoding CDKi fusion protein of the invention operably linked to an appropriate regulatory sequence (e.g., a CMV promoter and/or a SV40 poly A signal) may be inserted into a retroviral vector using standard techniques. The resulting CDKi-encoding vector may then be packaged in an appropriate packaging cell line to generate recombinant retrovirus encoding a CDKi fusion protein of the invention. For a standard retrovirus, such as a Moloney murine leukemia virus (MMLV), recombinant MMLV encoding a CDKi protein of the invention may be generated. In a standard MMLV transfer vector, such as the rkat43.3 vector (Finer et al. (1994) Blood 83:43–50), the transgene is inserted between the gag-encoding region and the 3'LTR. A standard MMLV transfer vector has a 7 kB transgene capacity.

Where the virus is an adeno-associated virus (AAV), standard recombinant DNA techniques may be employed to generate recombinant AAV encoding a CDKi protein of the invention. Recombinant AAV can be made by transfecting a producer cell with two trans-complementing plasmids, one plasmid encoding the rep and cap proteins, and the other plasmid encoding the transgene with the AAV inverted terminal repeat (ITR) sequences. The =transfected producer cell line then produces recombinant AAV infectious viral particles, which can be used to transduce cells. The transgene size capacity of an AAV transgene-ITR plasmid is typically approximately 4.5 kB. One exemplary CDKi protein of the invention, W9, is encoded by a nucleic acid sequence that is less than 0.7 kB. Thus, a transgene encompassing, for example, in the following or a CMV promoter/enhancer, CDKi-encoding nucleic acid sequence, IRES sequence, and SV40 polyA signal may be readily accommodated by a standard AAV transgene-ITR plasmid and may be used to generate recombinant AAV particles.

Figure 2:
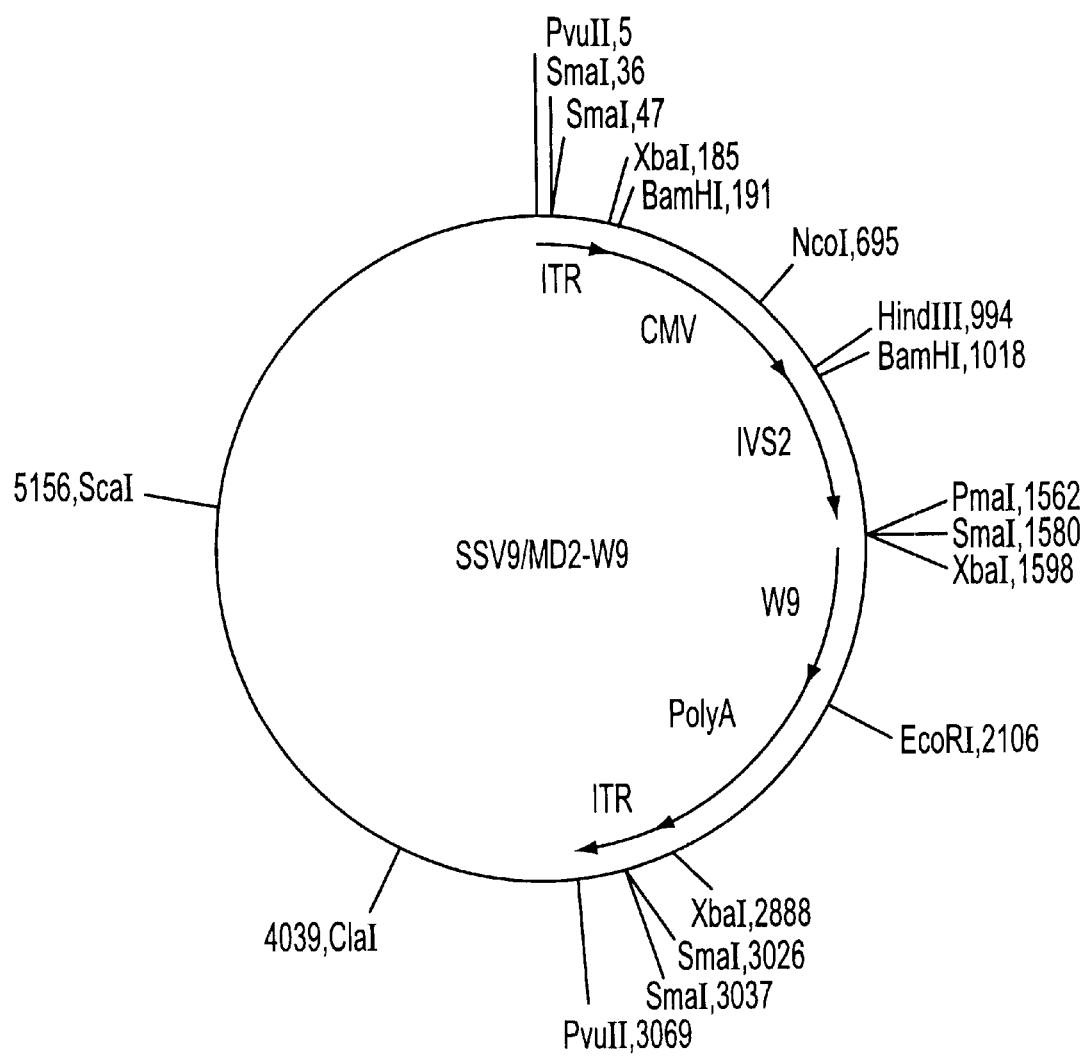
FIG. 2 is a diagrammatic representation of an adeno-associated viral (AAV) vector containing a transgene encoding W9, a non-limiting representative CDKi of the invention.

FIG. 2 depicts a representative AAV vector in which a transgene encoding the W9 fusion protein lies between the inverted terminal repeats (ITR) of AAV. The W9 protein-encoding transgene comprises a nucleic acid sequence encoding the W9 fusion protein operably linked at the 5' end to cytomegalovirus (CMV) immediate early gene promoter/enhancer (Genbank Accession No. X03922) from pBC12/CMV/IL-2 (Cullen (1986) *Cell* 46:973–982), a shortened second intervening sequence (IVS2; helps process the resulting mRNA), and at the 3' end to a poly adenylation signal. Recombinant AAV may be produced by cotransfecting this AAV vector together with an AAV helper plasmid into 293 cells and then infecting the transfected 293 cells with adenovirus d1312 as described in Samulski et al. (1989) *J. Virol.* 63:3822–3828.

Figure 3A:
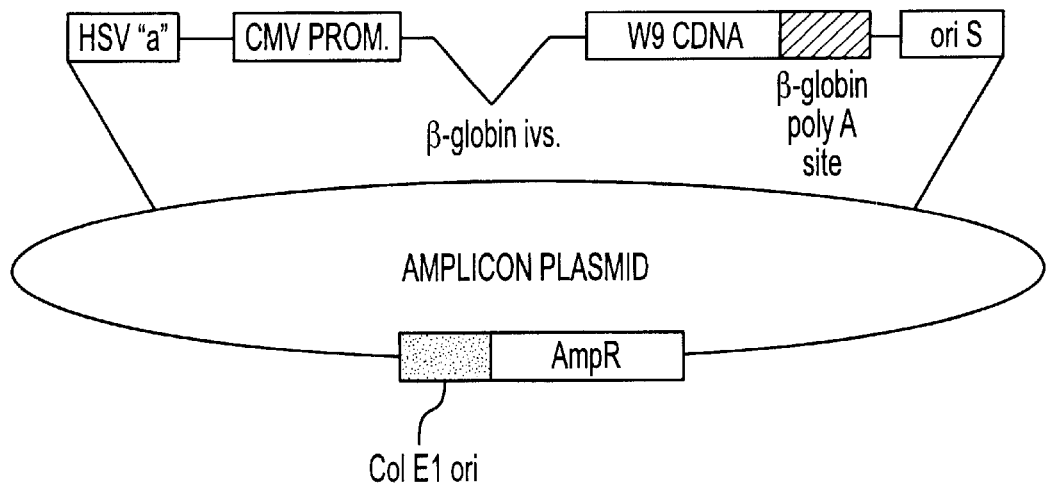
FIG. 3A is a schematic representation of an HSV-based amplicon, according to the invention, which contains a transgene encoding W9, a non-limiting representative CDKi of the invention, a W9-encoding nucleic acid sequence operably linked to appropriate regulatory sequences.

FIG. 3A depicts a representative herpesvirus (HSV)-based construct or amplicon which contains a transgene comprising a nucleic acid sequence encoding an exemplary CDKi protein of the invention (e.g., the W9 fusion protein) operably linked to exemplary regulatory sequences. The HSV "a" and ori sequences permit replication and packaging of recombinant HSV in complementing cells infected with the d120 helper virus. The complementing cells supply ICP4 function missing from the d120 (see, e.g., Spete et al. (1982) *Cell* 30:295–304).

Figure 3B:
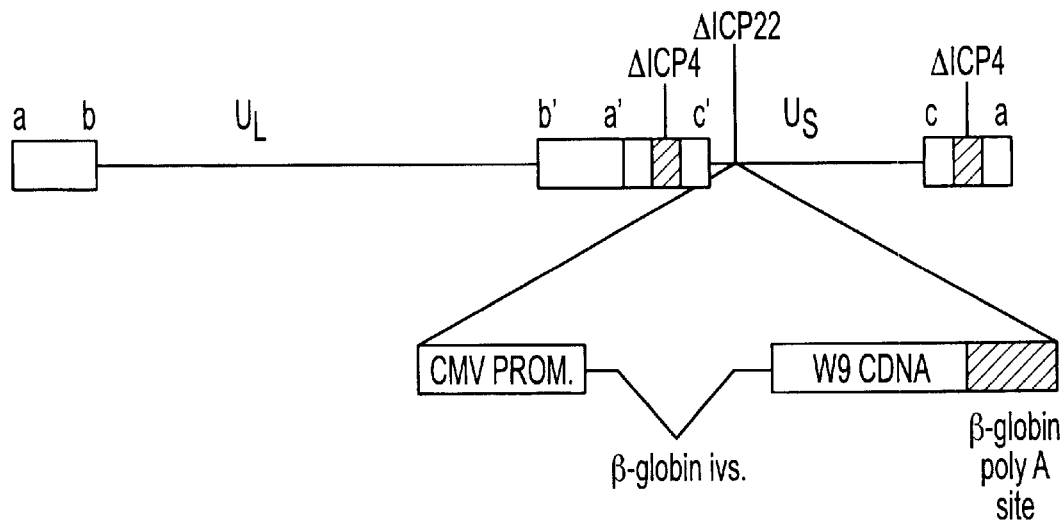
FIG. 3B is a schematic representation of an HSV-1-based vector, according to the invention, which contains a transgene encoding W9, a non-limiting representative CDKi of the invention, replacing the ICP22 HSV gene.

Another useful herpesvirus vector is the HSV-1 based vector depicted in FIG. 3B. Many regions of the HSV genome not needed for growth in cultured cells can be removed and a transgene encoding a fusion CDKi of the invention substituted in. In the non-limiting example shown, the ICP22 gene has been substituted with a W9 fusion protein-encoding transgene. This transgene comprises a CMV promoter, a β globin IVS (to help process the resulting mRNA), W9-encoding cDNA, and a β-globin polyA site. The resulting vector is defective for growth on normal cells, as the ICP4 genes in the vector have also been removed. This vector may be packaged in a cell line such as 7B (which provides the ICP4 and ICP27 proteins) to generate recombinant herpes virus particles that encode W9 and allow expression of W9 protein in a transduced cell (see, e.g., Glorioso et al. (1995) *Ann. Rev. Microbiol.* 49:675–710).

Figure 4A:
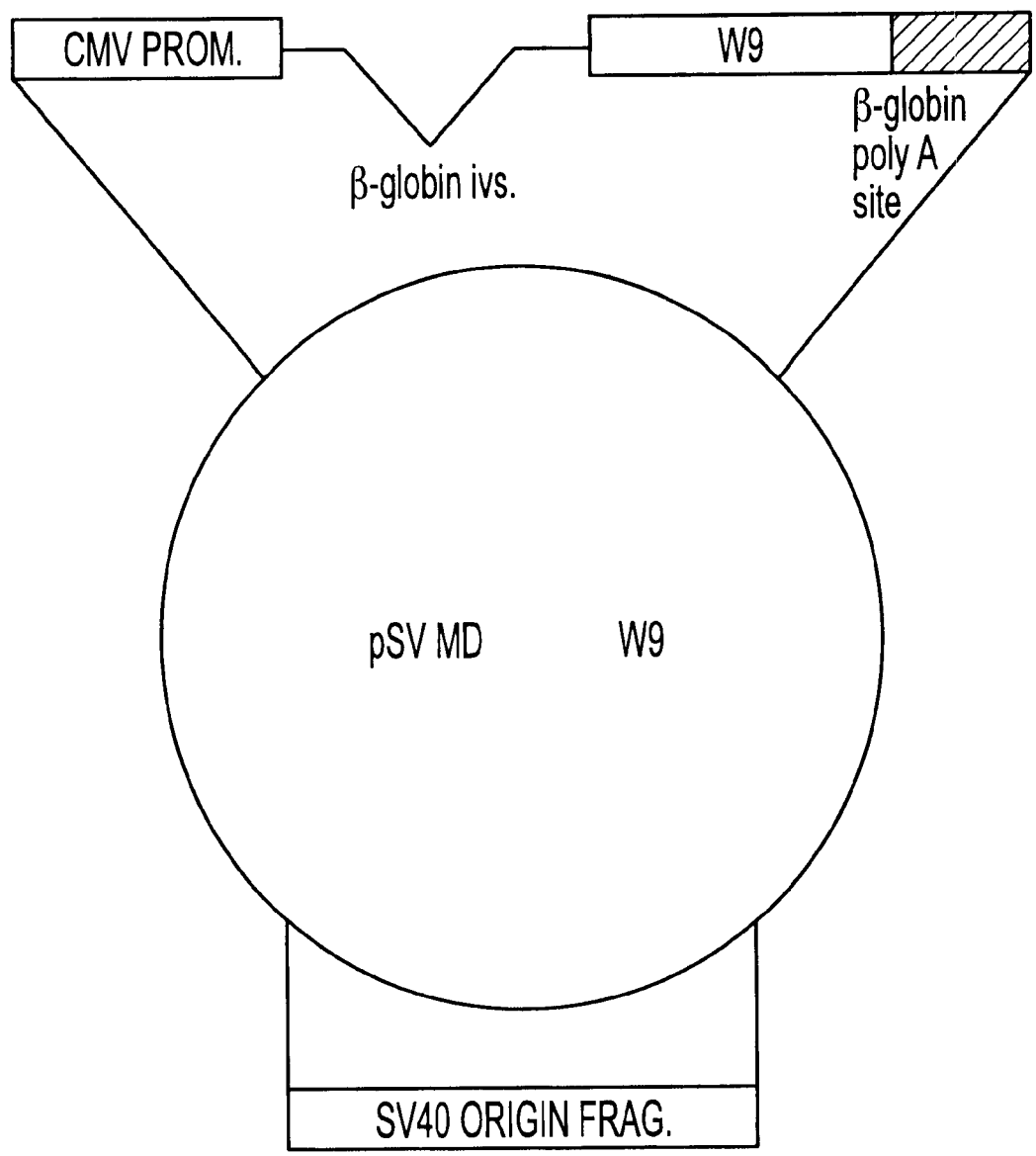
FIG. 4A is a schematic representation of an SV-40 vector (pSV MD W9) according to the invention, which includes a transgene encoding W9, a non-limiting representative CDKi of the invention, and the SV-40 origin of replication.

FIG. 4A illustrates a representative SV40-based W9 vector which contains a W9-encoding transgene comprising the following operably linked nucleic acid sequences: a CMV promoter, a β globin IVS, W9-encoding cDNA, and a β-globin polyA site. The vector also contains the SV-40 ori (SV-40 nucleotides 5177–290). The total size of the plasmid is preferably less than 5243 bases and packaging can be accomplished, for example, in COS-7 cells according to Fang et al. (1997) *Analyt. Biochem.* 254:139–143.

Figure 4B:
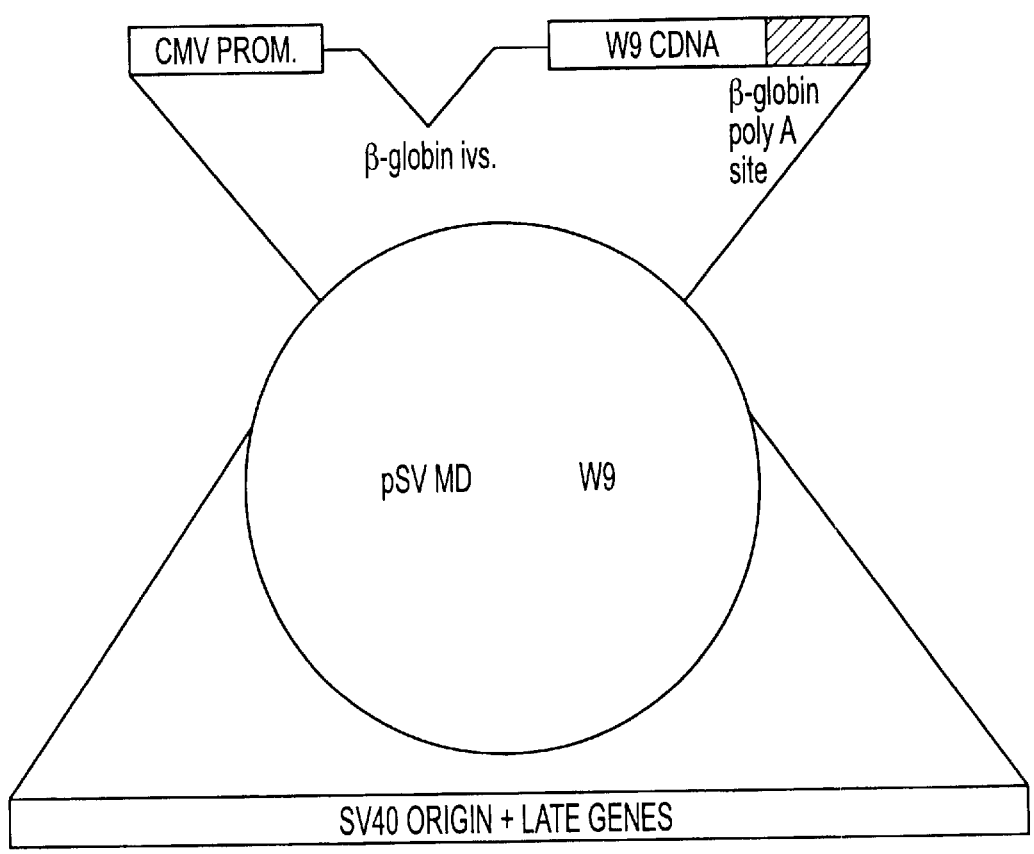
FIG. 4B is a schematic representation of an SV-40-based vector (pSV MD W9 II), according to the invention, which includes a transgene encoding W9, a non-limiting representative CDKi of the invention, the SV-40 origin of replication, and viral late genes.

An alternative SV-40 based recombinant vector is shown in FIG. 4B and includes a W9-encoding transgene, and the SV-40 ori plus the viral late genes (SV-40 nucleotides 5177–2770). The total size of the vector is preferably less than 5243 bases. Packaging of the vector can be accomplished, for example, in COS-7 cells as described in Fang et al. (1997) *Analyt. Biochem.* 254:139–143). This vector can be generated from a larger plasmid containing a plasmid origin and selectable marker. The sequences are removed by restriction digestion, and the ends of the vector fragment are joined to make a circle by T4 DNA ligase.

Recombinant Epstein Barr viruses can also be used to deliver the CDKi of the invention to endothelial cells (see, e.g., Robertson et al. (1996) *Proc. Natl. Acad. Sci. USA* 93(21):11334–11340, and Shimizu (1996) *J. Virol.* 70(10):7260–7263).

Figure 5:
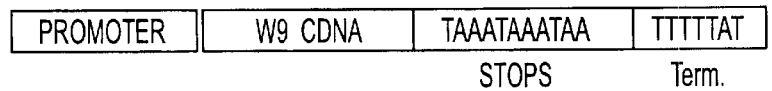
FIG. 5 is a schematic representation of a vaccinia virus vector including a vaccinia virus promoter, a transgene encoding W9, a non-limiting representative CDKi of the invention, and a termination sequence.

The vaccinia virus expression cassette shown in FIG. 5 is also useful in the methods of the invention. As vaccinia viruses do not rely on the host cell's expression machinery, the inserted transgene (e.g., nucleic acid sequence encoding a CDKi fusion protein operably linked to appropriate regulatory sequences) must be flanked with the appropriate vaccinia sequences. The promoter is preferably a vaccinia virus promoter, such as H6 which is active in both early and late phases of the vaccinia virus life cycle. Additionally, after the inserted nucleic acid, a termination sequence of TTTTTNT is required in the early phase. Using homologous recombination, this vaccinia virus expression cassette, which consists of a CDKi fusion protein-encoding nucleic acid sequence operably linked to regulatory sequences derived from the vaccinia virus, can be inserted into any region of the vaccinia genome which is dispensable for growth in cells (see, e.g., Perkus et al. (1989) *J. Virol.* 63:3829–3836).

It should be noted that where a recombinant virus is used to deliver the transgene encoding the CDKi of the invention, the inserted transgene may also use regulatory sequences endogenous to the virus (e.g., a viral promoter/enhancer).

In a certain embodiment of the first aspect of the invention, the endothelial cell is in a mammal. In a certain embodiment, the endothelial cell is a cultured endothelial cell.

In a certain preferred embodiment of the first aspect of the invention, the endothelial cell to which the transgene encoding a CDKi of the invention is later administered is an endothelial cell that is induced to proliferate and/or migrate by a condition associated with angiogenesis.

In particular embodiments, the angiogenesis-associated condition is neoplasia, rheumatoid arthritis, vascular retinopathy, or endometriosis. By "neoplasia" is meant a condition involving any tissue or organ that shows aberrant growth. In one case, the aberrant cell growth of a neoplasm is due to increased cell growth. Thus, neoplasia includes hyperplasia, a growth of cells showing a lack of contact inhibition of growth in vitro, a benign tumor that is incapable of metastasis in vivo, or a cancer that is capable of metastases in vivo and that may recur after attempted removal. By "tumor angiogenesis" is meant angiogenesis induced by or stimulated by neoplasia.

There are several means by which tumor cells evade common anti-tumor therapies: tumor cells downregulate MHC molecules on their surface to evade immuno-surveillance by T cells; and tumor cells are also often radio-resistant (unaffected by radiation) or chemo-resistant (unaffected by normally toxic chemotherapeutic agents) because (mutated) proteins within the tumor cells lead to, for example, disruption of apoptotic or other programmed cell death pathways or removal of the chemotherapeutic drug from the cell. One example of a tumor cell protein that confers chemo-resistance is the multi-drug resistance (MDR) protein on the cell surface which "pumps" out chemotherapeutic drugs which would have to be within the cell to function. Similarly, tumor cells that lack functional retinoblastoma protein (Rb) are resistant to apoptosis induced by over expression of the CDKi p15, and tumor cells that have a normal p53 are not killed by over expression of p53. Finally, cells can become resistant to apoptosis due to defects in the caspase family of proteins which are critical components of the apoptotic pathway. These are just some examples of how tumors evade death. The anti-angiogenic approaches of the present invention circumvent these evasion strategies because they do not target the tumor cells, but rather target downstream target cells that are required to form the vasculature that provides the tumor with its essential nutrients. Thus, the method of the first aspect of the invention includes an embodiment wherein the angiogenic condition is vascularization of neoplasia, wherein the tumor is insensitive to the anti-proliferative activity of p16, e.g., the cells are defective for the retinoblastoma protein (such as a loss of function mutation) or have a mutation in the CDK4 or CDK6 gene which disrupts binding of the encoded proteins with p16 protein.

Accordingly, the recombinant virus comprising CDKi of the invention may be administered to an individual having, or suspected of having a condition associated with angiogenesis. In one example, the angiogenesis-inhibiting reagents and compositions of the invention are administered to an individual within a pharmaceutically-acceptable diluent, carrier, or excipient, in unit dosage form according to conventional pharmaceutical practice. Administration may begin before the individual is symptomatic. If desired, treatment of a cancer patient with the angiogenesis-inhibiting reagents and compositions of the invention may be combined with more traditional therapies or other angiogenesis-inhibiting reagents.

Recombinant viral particles, such as recombinant adenoviruses, carrying transgenes encoding a CDKi protein may be administered in a pharmaceutically acceptable formulation systemically via the blood stream or lymphatic system. Preferably, recombinant viruses of the invention are administered locally to a site in close proximity to a cell affected by a condition associated with angiogenesis. Devices, including cannulas and i.v. lines, can be used to supply recombinant virus particles to an artery or vein lined with endothelial cells that are induced to proliferate and migrate by the condition associated with angiogenesis.

In a second aspect, the invention provides a method for inhibiting angiogenesis comprising contacting an endothelial cell with an effective amount of a liposome that comprises a transgene encoding a mammalian cyclin dependent kinase inhibitor, wherein the transgene is internalized by the endothelial cell, and wherein proliferation and/or migration of the contacted endothelial cell is inhibited.

In a certain preferred embodiment, the liposome contains on its external surface a molecule that binds to a cell surface protein on the endothelial cell, wherein binding of the molecule to the cell surface protein facilitates the fusion of the endothelial cell with the liposome. Alternatively or additionally, the molecule that binds to a cell surface protein on the endothelial cell facilitates the DNA transfection of the endothelial cell by the liposome. By "external surface" of a liposome is meant the surface facing away from the interior of the liposome and, thus, away from the compartment of the liposome containing a CDKi of the invention, or a nucleic sequence encoding the same. Thus, a molecule expressed on the external surface of a liposome may be attached only to the outer leaflet of the exterior surface of the liposome, or may traverse the surface of the liposome, such that part of the molecule is expressed external to and part of the molecule is expressed internal to the liposome.

By "cell surface protein" is meant a protein that is expressed and transported to the cell surface of an endothelial cell. Such a protein may be attached only to the outer leaflet of the cell membrane of an endothelial cell (e.g., a glycosylphosphatidylinositol-anchored protein), or may traverse the cell membrane. One example of a cell surface protein on an endothelial cell is the VEGF receptor.

By "binds" is meant that the molecule on the external surface of the recombinant virus or liposome interacts with a cell surface protein on an endothelial cell such that the transgene contained by the recombinant virus or liposome is taken up by the endothelial cell.

Liposomes, which closely resemble the lipid composition of natural cell membranes, can be generated which incorporate the transgene encoding a CDKi or, alternatively, the CDKi proteins of the invention. In the latter case, the CDKi protein need not be internalizable, as the liposome will fuse to the cell membrane of an endothelial cell, thereby depositing its contents into the cytoplasm of the cell. For example, the composition may first be packaged in a liposome that bears a surface positive charge. Upon delivery to a cell either in vitro or in vivo, the liposome will fuse with the cell membrane and deposit the protein contained within the liposome into the cytoplasm of the cell. Liposome packaging and delivery of proteins is well known (see, generally, Mouritsen and Jorgensen (1998) *Pharm. Res.* 15(10):1507–1519; Selzman et al. (1999) *Circ. Res.* 84(8):867–875; and Zheng et al. (1999) *AIDS Res. Hum. Retroviruses* 15(11):1011–1020; Fong et al. (1997) *J. Virol. Methods* 66(1):149–157.

Liposomes containing a transgene encoding a CDKi of the invention can be formed such that the liposome expresses on its external surface a molecule that binds to a cell surface protein on an endothelial cell (e.g., a VEGF molecule that is modified to comprise a transmembrane domain).

In one example where the molecule that binds to a cell surface protein on an endothelial cell is a transmembrane domain-containing VEGF protein, the VEGF-tm protein can be made in sufficient quantities by standard molecular biology techniques. For example, VEGF-encoding sequences are known (e.g., human VEGF sequence is available in GenBank Accession No. E15157, Uchida, K., Japanese Patent No. JP 1998052285-A), as are transmembrane domains (see, e.g., Romeo et al. (1992) *Cell* 68(5):889–897; Kolanus et al. (1993) *Cell* 74(1):171–183). To produce a VEGF-tm protein (i.e., a VEGF molecule modified to comprise a transmembrane domain), a VEGF-tm-encoding transgene (e.g., nucleic acid sequence encoding VEGF-tm operably linked to a regulatory sequences such that the VEGF-tm protein is expressed by a cell into which the nucleic acid sequence has been introduced) may be subcloned into any standard expression vector (e.g., bacteriophage, baculovirus vector or mammalian expression vector). The VEGF-tm-encoding expression vector may then be introduced into a host cell, such as a bacterium, an insect cell, or a mammalian cell, and the resulting VEGF-tm protein isolated and purified by standard techniques (e.g., HPLC, dialysis or immunoprecipitation).

To generate a CDKi-encoding transgene-containing liposome expressing a molecule that binds to a cell surface protein on an endothelial cell, the molecule (e.g., VEGF-tm) is combined with the liposome-forming components and the CDKi-encoding transgene under conditions to facilitate formation of liposomes.

In a certain embodiment, the CDKi is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. CDKi's are as described above for the first aspect of the invention.

In a certain embodiment of the second aspect of the invention, the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In certain embodiments, the fusion protein comprises an active fragment of a protein from the CIP/KIP family, wherein the fragment is selected from the group consisting of amino acids 25–93 of human p27 protein and amino acids 12–178 of human p27 protein. In a certain embodiment, the second cyclin dependent kinase inhibitor is a protein from the INK4 family. In certain embodiments, the second cyclin dependent kinase inhibitor is human p16. In some embodiments, the cyclin dependent kinase inhibitor is a fusion protein comprising at least an active fragment of human p16 and at least an active fragment of human p27, and is W7 or W9.

In certain embodiments of the second aspect of the invention, the encoded cyclin dependent kinase inhibitor is internalizable. In certain embodiments, the cyclin dependent kinase inhibitor is secretable. A "secretable" protein is one that is engineered such that it will be discharged or released by the cell which produces it.

In a third aspect, the invention provides a method for inhibiting angiogenesis by contacting a target endothelial cell with a cyclin dependent kinase inhibitor of the invention, wherein proliferation and/or migration of the cell is inhibited, and wherein the inhibitor is selected from the group consisting of a protein from the INK4 family or an active fragment thereof; a protein from the CIP/KIP family or an active fragment thereof; and a fusion protein comprising at least an active fragment of the protein from the INK4 family and at least an active fragment of the protein from the CIP/KIP family. Preferably the CDKi is mammalian and is internalizable. In some nonlimiting examples, the active fragment of the protein from the CIP/KIP family in amino acids 25–93 or 12–178 of human p27 protein. In some preferred examples, the CDKi is W7 or W9. As used herein, a "target cell" is the cell which is to be contacted by the CDKi.

In one embodiment of the third aspect of the invention, the endothelial cell internalizes the internalizable cyclin dependent kinase inhibitor. By "internalize" is meant that the cell takes up a protein into its cytoplasm and/or nucleus, where the internalized protein can participate in intracellular functions.

Preferably, a cyclin dependent kinase inhibitor of the invention is engineered such that it includes a translocation sequence, thereby allowing it to be internalized by a cell. A protein engineered such that it can be internalized by a cell is called an "internalizable" protein. By "engineered" is meant using standard molecular biology techniques to modify a nucleic acid sequence (and the resulting encoded protein) (see general laboratory manuals Maniatis et al., *Molecular Cloning: A Laboratory Manual* (2nd ed.), Cold Spring Harbor Press, 1989; and Ausubel et al., *Current Protocols in Molecular Biology,* John Wiley & Sons, New York, N.Y., 1994). "Nucleic acid sequence" includes, without limitation, deoxyribonucleic acid (DNA), ribonucleic acid (RNA), analogs of either DNA or RNA, mRNA, and cDNA. Engineered proteins and/or nucleic acids may be modified such that amino acid residues or nucleotide bases are added or subtracted, or even replaced with other amino acid residues or nucleotide bases. As used herein, an "engineered" recombinant virus is one in which a nucleic acid sequence contained within its genomic material has been modified according to standard molecular biology techniques.

Accordingly, an engineered cyclin dependent kinase inhibitor of the invention preferably comprises translocation sequences that facilitate the translocation of a protein across the cell membrane of a cell, thereby allowing the protein to be internalized by that cell. Several representative translocation sequences sufficient to direct protein internalization are known and include a portion of the Drosophila antepennepedia protein (GenBank Accession No. E01911; Asato et al. (1989) Japanese Patent No. 1989085092-A1; Derossi et al. (1996) *J. Biol. Chem.* 271:18188–18193; Derossi et al. (1994) *J. Biol. Chem.* 269:10444–10450; Perez et al. (1992) *J. Cell. Sci.* 102:717–722) the HIV transactivator (TAT) protein (Kuppuswamy et al. (1989) *Nucl. Acids Res.* 17:3551–3561; Frankel and Pabo (1989) *Cell* 55:1189–1193; Green and Lowenstein (1989) *Cell* 55:1179–1188), and mastoparan (Higashijima et al. (1990) *J. Biol. Chem.* 265:14176–141860). In certain embodiments, the engineered internalizable CDKi of the invention comprises a translocation sequence that is the sequence encoding amino acids 48–60 or amino acids 47–72 of the HIV tat protein.

In a certain preferred embodiment, the cyclin dependent kinase inhibitor is a fusion protein comprising at least an active fragment of a first cyclin dependent kinase inhibitor and at least an active fragment of a second cyclin dependent kinase inhibitor. A "fusion protein" of the invention is a single polypeptide chain that comprises at least a active fragment of a first protein and at least a active fragment of a second protein, wherein the two fragments are joined either directly or indirectly with a peptide bond. It will be understood that the fusion protein of the invention may comprise more than two proteins (or active fragments thereof). Each fragment of a fusion protein may be from a separate CDKi, or may be from the same CDKi. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the active fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16.

For example, one fusion protein of the invention comprises the full length murine p16 protein joined to the full length human p21 protein. Another fusion protein of the invention comprises an active fragment of the human p27 protein with the full length human p16 protein. Yet another fusion protein of the invention includes the ten N-terminal amino acids of the human p27 protein joined to the ten C-terminal amino acids of the human p27 protein. In some embodiments, the cyclin dependent kinase inhibitor is a fusion protein comprising at least an active fragment of human p16 and at least an active fragment of human p27, and is W3, W4, W5, W6, W7, W8, W9, or W10. In preferred embodiments, the cyclin dependent kinase inhibitor is W7 or W9. In a particularly preferred embodiment, the cyclin dependent kinase inhibitor is W9.

Fusion proteins of the invention may include a linker between the two joined active fragments. A "linker" is any chemical, synthetic, carbohydrate, lipid, polypeptide (or combination thereof) molecule positioned between and joined to two adjacent active fragments in a fusion protein. A preferred linker of the invention is a polypeptide chain consisting one or more amino acid residues joined by amino acid bonds to the two active fragments. For example, a (Gly$_4$Ser)$_3$ linker may be positioned between the two active fragments in the fusion protein.

In certain embodiments, the method further comprises delivering a transgene encoding an internalizable cyclin dependent kinase inhibitor to an auxiliary cell, wherein the transgene is expressed by the auxiliary cell to produce the cyclin dependent kinase inhibitor, wherein the auxiliary cell releases the cyclin dependent kinase inhibitor into the blood, and wherein the bloodborne cyclin dependent kinase inhibitor contacts the target endothelial cell. An "auxiliary cell" is a cell which is not the target cell. In one embodiment, the encoded CDKI also contains a signal sequence enabling the CDKi to be secreted from the auxiliary cell.

For example, a secretable, internalizable CDKi of the invention may comprise a leader sequence from an immunoglobulin protein fused to the entire HIV tat protein fused to the amino-terminal end of a CDKi of the invention (see, e.g., Fawell et al. (1994) *Proc. Natl. Acad. Sci. USA* 91(2):664–668). Preferably, the internalizable CDKi of the invention comprises a translocation sequence that is the sequence encoding amino acids 48–60 or amino acids 47–72 of the full length HIV tat protein.

Figure 15A:
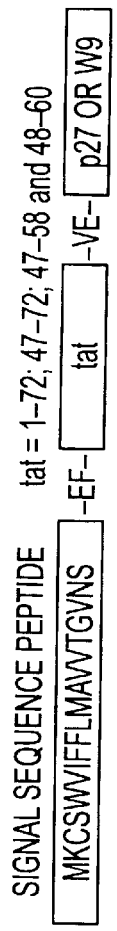
FIG. 15A is a diagrammatic representation of a representative secretable, internalizable form of W9 containing a signal sequence peptide from the murine immunoglobulin heavy chain gene.
Figure 15B:
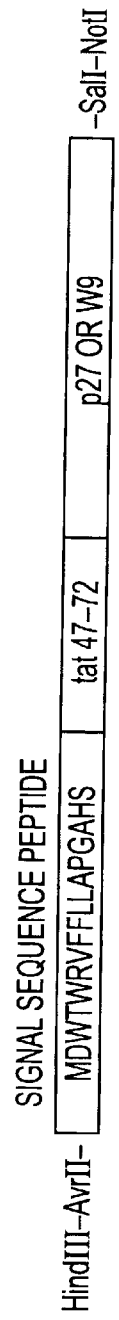
FIG. 15B is a diagrammatic representation of a representative secretable, internalizable form of W9 containing a signal sequence peptide from the human immunoglobulin heavy chain gene.
Figure 15C:
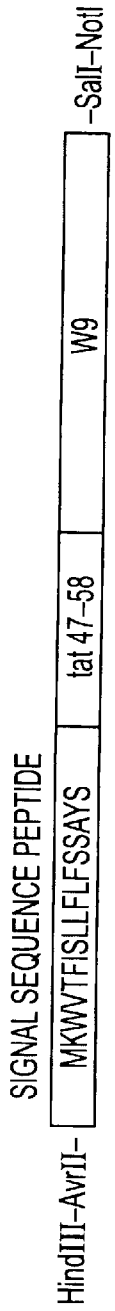
FIG. 15C is a diagrammatic representation of a representative secretable, internalizable form of W9 containing a signal sequence form the human serum albumin gene.

In one embodiment, the secretable, internalizable form of a CDKi of the invention has the following sequence: N terminus-(Leader peptide) bonded to (HIV tat amino acids 1–72 peptide) bonded to (CDKi protein) -C terminus. Other preferred embodiments of secretable, internalizable CDKi proteins of the invention are generated in cells introduced with transgenes encoding the constructs schematically depicted in FIGS. 15A–15C. In yet additional embodiments, the secretable, internalizable form of a CDKi of the invention has a signal (leader) sequence from proinsulin, a translocation sequence from HIV tat amino acids 1–72, and where the secretable, internalizable CDKi is W9, the nucleic acid sequence is provided in SEQ ID NO:29, and the amino acid sequence is provided in SEQ ID NO:30.

In addition, the signal peptide and translocation sequences may be separated from the CDKi with a linker, such as a (Gly$_4$Ser)$_3$ linker. Where the secretable, internalizable CDKi is W9, the linker is the (Gly$_4$Ser)$_3$ linker, the translocation sequence is HIV tat amino acids 1–72, and the signal (leader) sequence is from proinsulin, the nucleic acid sequence is provided in SEQ ID NO:31, and the amino acid sequence is provided in SEQ ID NO:32.

In certain embodiments, the internalizable CDKi does not possess a secretion signal. When this CDKi is expressed from a recombinant virus that promotes lysis of a transduced cell, the internalizable CDKi is released, allowing uptake by neighboring or distant endothelial cells, whereupon it inhibits angiogenesis.

To deliver the CDKi of the invention to endothelial cells, standard administration protocols may be employed. The CDKi proteins, or nucleic acid sequences, liposomes or recombinant viruses including transgenes encoding a CDKi protein of the invention may be combined with pharmaceutically acceptable carriers and/or other therapeutic reagents to generate therapeutic compositions for use in vivo. Accordingly, the CDKi protein, nucleic acid sequences encoding the CDKi proteins, recombinant viruses, or liposomes of the invention may be formulated for administration with pharmaceutically acceptable carriers such as water, buffered saline, polyol (e.g., glycerol, propylene glycol, liquid polyethylene glycol), or suitable mixtures thereof. In one embodiment, the nucleic acid sequences or proteins of the invention are dispersed in liquid formulations, such as micelles or liposomes, which closely resemble the lipid composition of natural cell membranes.

Formulations for parenteral administration may, for example, contain sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-poloxypropylene copolymers may be used to control the release of the CDKi of the invention. Other potentially useful parenteral delivery systems include ethylene-vinyl acetate copolymer particles, osmotic pumps, and implantable infusion system. By "pharmaceutically acceptable carrier" is meant a carrier that is physiologically acceptable to the administered individual and that retains the therapeutic properties of the cyclin dependent kinase inhibitor or nucleic acid encoding the inhibitor with which is it administered. One exemplary pharmaceutically acceptable carrier is physiological saline. Other pharmaceutically-acceptable carriers and their formulations are well-known and generally described in, for example, *Remington's Pharmaceutical Sciences* (18th Edition, ed. A. Gennaro, Mack Publishing Co., Easton, Pa., 1990).

For the delivery of proteins lacking translocation sequences such that they will not be internalized by target cells, the protein is preferably first combined with a delivery system that will facilitate the internalization of the protein by cells. In one nonlimiting example, the protein may first be packaged in a liposome, for example, that bears a surface positive charge.

Administration of a CDKi protein or nucleic acid encoding a CDKi protein to cells in vivo may be accomplished by any suitable method or route including without limitation, parenteral intravenous, intra-arterial, subcutaneous, intramuscular, intraperitoneal, intranasal, aerosol, by suppositories, or oral administration. Therapeutics may be in the form of liquid solutions or suspensions; for oral administration, formulations may be in the form of tablets or capsules; and for intranasal formulations, in the form of powders, nasal drops, or aerosols. Preferably, the angiogenesis-inhibiting reagents and compositions of the invention are administered locally to the affected area (e.g., directly into the tumor mass), or may be administered systemically. Preferably, where the CDKi proteins themselves are injected, the proteins are purified, administered with a pharmaceutically acceptable carrier (e.g., physiological saline), and are internalizable by endothelial cells. For example, compositions that comprise a CDKi protein (e.g., a secretable, internalizable form of a CDKi protein) or a nucleic acid sequence encoding a CDKi protein may be diluted in culture media and added to cells cultured in vitro. Similarly, for in vivo delivery, compositions comprising a CDKi protein or nucleic acid sequences encoding a CDKi protein may be combined with a pharmaceutically acceptable carrier, such as buffered saline, and administered (e.g., to the site of cells affected by a condition associated with angiogenesis) by injection with a syringe or catheter.

In a fourth aspect, the invention provides a purified internalizable form of a cyclin dependent kinase inhibitor. An "internalizable" protein is one that is engineered such that it will be internalized by an endothelial cell, as described above in the first aspect of the invention. By "purified" is meant a protein that has been separated from components which naturally accompany it or, in the case of a protein generated by recombinant biology techniques, components that accompany it in the engineered cell or virus. Of course, those of ordinary skill in protein chemistry will understand that water, buffers, and other small molecules may additionally be present in a purified protein preparation. Typically, a purified protein is pure when it is at least 60%, by weight, free from other accompanying proteins and organic molecules (e.g., nucleic acid). Preferably, a purified protein is at least 75%, more preferably, at least 90%, even more preferably, at least 95%, and most preferably at least 99% by weight, free from accompanying proteins and organic molecules. Preferably, a purified internalizable form of a CDKi protein of the invention is obtained by expression of a nucleic acid sequence encoding the secretable, internalizable form of the CDKi protein. Purity can be measured by any appropriate method including, without limitation, column chromatography, polyacrylamide gel electrophoresis, and HPLC analysis.

For example, a nucleic acid sequence encoding a secretable, internalizable form of a CDKi protein of the invention may be introduced into a prokaryotic or eukaryotic cell in vitro, such that the nucleic acid sequence can be expressed in that cell. The protein is then secreted, in which case it may be purified from the conditioned culture media of the cell. Recombinant virus encoding a secretable, internalizable form of a CDKi protein may also be used to transduce eukaryotic cells. The expressed secretable, internalizable CDKi protein may then be purified from the transduced cell by lysis of the cell. Alternatively, internalizable forms of the CDKi proteins of the invention (e.g., an internalizable W9 CDKi fusion protein) may be completely synthetic and be chemically produced on a peptide synthesizer.

In a certain embodiment of the fourth aspect of the invention, the purified internalizable form of a cyclin dependent kinase inhibitor is a fusion protein comprising at least an active fragment of a first cyclin dependent kinase inhibitor and at least an active fragment of a second cyclin dependent kinase inhibitor. "Fusion proteins" are as defined above in the first aspect of the invention. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In preferred embodiments, the cyclin dependent kinase inhibitor is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

The cells according to the third and fourth aspects of the invention containing the transgenes encoding and expressing the secretable, internalizable CDKi proteins secrete internalizable CDKi proteins, which can then be purified, in accordance with the fourth aspect of the invention, or used in a paracrine fashion. By "paracrine" is meant action by a protein on a target cell wherein the protein was not produced in the target cell, but was produced in an auxiliary cell. It should be noted that the leader sequence (signal sequence peptide) is cleaved by the transduced cell prior to the secretion of the internalizable CDKi protein of the invention. It should also be noted that while some of the CDKi's described in the examples below comprise a 6 His and/or Hemagglutinin (HA) tag at their N-terminus, the internalizable forms of the CDKi of this aspect of the invention do not have a 6 His and/or HA tag at their N-terminus. Accordingly, to generate an internalizable form of a CDKi of this aspect of the invention, a nucleic acid sequence encoding the CDKi to which is operably linked the translocation sequence with or without the signal peptide sequence preferably does not comprise a 6 His tag or a HA tag. For example, a nucleic acid sequence encoding a W9 CDKi protein of the invention which lacks a 6 His, HA tag is provided in SEQ ID NO:23.

According to the third and fourth aspects of the invention, a transgene encoding a secretable, internalizable CDKi of the invention may be introduced into any cell type by any means. The cell according to this aspect of the invention includes, without limitation, a smooth muscle cell or an endothelial cell.

The internalizable form of the CDKi proteins of the fourth aspect of the invention may be combined with pharmaceutically acceptable carriers and/or other therapeutic reagents to generate therapeutic compositions for use in vivo. Such formulations are as described for the first aspect of the invention. In a fifth aspect, the invention provides a method for treating a condition associated with angiogenesis. In this method, a therapeutically effective amount of the therapeutic composition comprising a purified internalizable form of a cyclin dependent kinase inhibitor and a pharmaceutically acceptable carrier is administered to a patient having or suspected of having the condition.

By "therapeutically effective amount" is meant the total amount of each active component of a therapeutic composition that is sufficient to show a meaningful patient benefit. When administered to a subject having a condition associated with angiogenesis, a therapeutically effective amount is an amount sufficient to slow angiogenesis, more preferably, to arrest angiogenesis, and, most preferably, to completely inhibit angiogenesis.

In a sixth aspect, the invention provides a method for treating a condition associated with angiogenesis. In this method, a therapeutically effective amount of a recombinant virus comprising a transgene encoding a cyclin dependent kinase inhibitor is administered to a patient having or suspected of having the condition. In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. In a certain preferred embodiment, the cyclin dependent kinase inhibitor is derived from a mammal (e.g., a human).

In a certain embodiment of the sixth aspect of the invention, the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In preferred embodiments, the cyclin dependent kinase inhibitor is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

It is contemplated that any virus can be used which comprises the transgene and which can be administered to a patient. In a particular embodiment of the sixth aspect of the invention, the recombinant virus is an adenovirus, a lentivirus, a retrovirus, an SV-40 virus, an Epstein Barr virus, a herpesvirus, an adeno-associated virus, or a pox virus, such as a vaccinia virus. In a certain embodiment, the adenovirus lacks an essential viral protein-encoding sequence region. In a certain embodiment, the adenovirus is replication-deficient. In a preferred embodiment, the adenovirus lacks a functional E1 region. In a certain embodiment, the adenovirus lacking the functional E1 region additionally lacks a functional second region, such as an E2 region, an E3 region, or an E4 region. In a particularly preferred embodiment, the functional second region is the E4 region.

In a seventh aspect, the invention provides a recombinant virus comprising a transgene encoding a cyclin dependent kinase inhibitor, wherein the recombinant virus is selected from the group consisting of an adenovirus lacking an E1 and an E4 region, a lentivirus, a retrovirus, an SV-40 virus, an Epstein Barr virus, a herpesvirus, an adeno-associated virus, and a pox virus.

Recombinant viruses containing transgenes encoding the CDKi of the invention, and methods for making them, are as described above in the first aspect of the invention. In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. In a certain preferred embodiment, the cyclin dependent kinase inhibitor is a derived from a mammal (e.g., a human).

In a certain embodiment of the seventh aspect of the invention, the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In preferred embodiments, the cyclin dependent kinase inhibitor is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

In an eighth aspect, the invention provides a liposome comprising a cyclin dependent kinase inhibitor. Liposomes containing the CDKi proteins of the invention, and methods for making them, are as described above in the first aspect of the invention. In a certain embodiment, the cyclin dependent kinase inhibitor is a protein from the CIP/KIP family or an active fragment thereof, such as an active fragment selected from the group consisting of amino acids 25–93 of human p27 protein and amino acids 12–178 of human p27 protein. In a certain embodiment, the cyclin dependent kinase inhibitor is a protein from the INK4 family or an active fragment thereof, such as human p16 protein or an active fragment thereof. In a certain preferred embodiment, the cyclin dependent kinase inhibitor is a derived from a mammal (e.g., a human).

In a certain embodiment of the eight aspect of the invention, the cyclin dependent kinase inhibitor is a fusion protein comprising at least an active fragment of a first cyclin dependent kinase inhibitor and at least an active fragment of a second cyclin dependent kinase inhibitor. In a certain embodiment, the first cyclin dependent kinase inhibitor is a protein from the CIP/KIP family. In certain embodiments, the first cyclin dependent kinase inhibitor is human p27. In a certain embodiment, the fusion protein comprises an active fragment of a protein from the CIP/KIP family, wherein the fragment is selected from the group consisting of amino acids 25–93 of human p27 protein and amino acids 12–178 of human p27 protein. In a certain embodiment, the second cyclin dependent kinase inhibitor is a protein from the INK4 family. In a certain embodiment, the second cyclin dependent kinase inhibitor is human p16. In preferred embodiments, the cyclin dependent kinase inhibitor is W7 or W9. In a particularly preferred embodiment, the cyclin dependent kinase inhibitor is W9. In a certain embodiment, the fusion protein comprises a linker positioned between the active fragment of the first cyclin dependent kinase inhibitor and the active fragment of the second cyclin dependent kinase inhibitor.

In a ninth aspect, the invention provides a nucleic acid composition comprising a nucleic acid sequence encoding an internalizable form of a cyclin dependent kinase inhibitor, wherein the nucleic acid sequence is operably linked to a regulatory sequence such that the cyclin dependent kinase inhibitor is expressed by an endothelial cell to which is administered the composition. In one embodiment, the nucleic acid sequence further encodes a secretory sequence.

In a tenth aspect, the invention provides a therapeutic composition comprising a nucleic acid composition comprising a nucleic acid sequence encoding a secretable, internalizable form of a cyclin dependent kinase inhibitor, wherein the nucleic acid sequence is operably linked to a regulatory sequence such that the cyclin dependent kinase inhibitor is expressed by an endothelial cell to which is administered the composition and a pharmaceutically acceptable carrier. In one embodiment, the therapeutic composition further comprises a delivery system that facilitates the internalization of the composition by the endothelial cell. In a certain embodiment, the delivery system is a recombinant virus. In preferred embodiments, the recombinant virus is an adenovirus, a lentivirus, a retrovirus, an SV-40 virus, an Epstein Barr virus, a herpesvirus, an adeno-associated virus, or a pox virus.

In an eleventh aspect, the invention provides a method for treating a patient having or suspected of having a condition associated with angiogenesis. In this method a therapeutically effective amount of a transgene encoding a secretable, internalizable form of a cyclin dependent kinase inhibitor is administered to a cell of the patient that is in close proximity to endothelial cells affected by the condition. In certain embodiments, the transgene is incorporated into a recombinant virus.

The invention now being generally described will be more readily understood by reference to the following examples which are included merely for purposes of illustration of certain aspects and embodiments of the present invention, and are not intended to limit the invention.

EXAMPLE I

Generation of p27/p16 Fusion Proteins

To create more potent anti-proliferative molecules that possess the activities of both the 1NK4 (p16) and CIP/KIP (p27) families, a number of recombinant CDKi's were created that fused the parental human p16 and p27 molecules, or their derivatives. The engineered CDKi's included fusion proteins of p16 fused to 5' and 3' truncated p27 molecules. These fusion proteins were designed to increase the protein's half-life and eliminate potential phosphorylation sites involved in the negative regulation of CDKi activity. The p27-p16 fusion proteins interacted with the CDK4/cyclinD, CDK2/cyclinA, and CDK2/cyclinE complexes and inhibited cell cycle progression at multiple points.

To generate the following non-limiting, representative CDKi fusion proteins of the present invention (and nucleic acid sequences encoding these proteins), the published sequences of the human p16 and p27 molecules were utilized. The nucleic acid (SEQ ID NO:25) and amino acid (SEQ ID NO:26) sequence of human p27 is available as GenBank Accession No. U10906 (Polyak et al. (1994) *Cell* 78:56–66). The nucleic acid (SEQ ID NO:27) and amino acid (SEQ ID NO:28) sequence of human p16 is available as GenBank Accession No. L27211 (Serrano et al. (1993) *Nature* 366:704–707; Okamoto et al. (1994) *Proc. Natl. Acad. Sci. USA* 91:11045–11049). To construct the representative, non-limiting CDKi fusion proteins of the invention, in general, PCR primers were used to insert a NdeI cloning site followed by sequence encoding 6×His and an epitope tag from the influenza virus hemagglutinin protein (HA tag) at the 5' end of full length p27 or truncated p27$_{25-93}$ and p27$_{12-178}$. In each instance, the CDKi gene was followed by an amber stop codon with SalI cloning site. The NdeI-SalI fragments were amplified by Deep Vent polymerase (commercially available from New England Biolabs, Beverly, Mass.) and cloned into plasmid pT7-7 (commercially available from US Biological (USB), Swampscott, Mass.) to yield pT7-His6-HA-p27, pT7-His6-HA-p27$_{25-93}$ and pT7-His6-HA-p27$_{12-178}$. To generate fragments without a stop codon and a (Gly$_4$Ser)3 linker, an alternate set of 3' PCR primers were used to insert sequence coding for a (Gly$_4$Ser)$_3$ linker in place of the stop codon with SalI cloning site at the 3' end. These NdeI-SalI amplified fragments were then subcloned into a NdeI and XhoI digested pKS plasmid containing full length p16, with the initiating ATG removed, generating an open reading frame in which the various p27 derivatives and full length p16 are linked by (Gly$_4$Ser)$_3$, histidine, and aspartic acid. The representative, non-limiting CDKi proteins of this example are schematically depicted in FIG. 2A, and were constructed as follows:

To construct the nucleic acid sequence encoding the p27-p16 fusion protein (i.e., N-terminal p27 and C-terminal p16) having a (Gly$_4$Ser)$_3$ hinge region between the p27 and p16 portions (W3), the p27 coding sequence was first PCR amplified using the following primers: N-terminal primer, which carries an NdeI site and 6 histidine codons that are inserted between the ATG and the second amino acid of p27 (SEQ ID NO:1):

5'-GCGGCCGGTCATATGCACCACCATCACCATCAC-TCAAACGTGCGAGTG TCT-3'; and C-terminal primer, which carries the (Gly$_4$Ser)$_3$ repeat and EcoRI, SalI, and HindIII restriction sites and eliminates the stop codon of p27 (SEQ ID iO NO:2): 5'-GCCGCCGGCGTC-GACTCGGCCGAATTCGGATCCACCCCCGCCG-GAACCCCACCCCCGCTGCCCCCGCCAC-CCGTTTGACGTCTTCTGAGGCCAGG-3'

The p27 PCR product was digested with NdeI and HindIII and inserted into pT7-7 linearized with NdeI and HindIII. The resulted construct was digested with EcoRI and SalI and a full length p16 PCR product was inserted as an EcoRI-XhoI fragment. The position of the EcoRI site allows the in-frame insertion of p16. The rest of the hinge region between the p27 and p16 coding sequences is derived from the 5' end of the p16 cDNA. The nucleic acid and amino acid sequence of W3 are provided, respectively, in SEQ ID NO:3 and SEQ ID NO:4.

A nucleic acid sequence encoding a second p27-p16 fusion protein, W4, was generated, where the p27 and p16 portions were not separated by a (Gly$_4$Ser)$_3$ hinge region. The W4-encoding nucleic acid sequence construct includes a 5' EcoRI site, along with the coding sequence for a N-terminal HA tag, and a 3' NotI site. The nucleic acid and amino acid sequence of W4 are provided, respectively, in SEQ ID NO:5 and SEQ ID NO:6.

Two p16-p27 fusion proteins (i.e., N-terminal p16 and C-terminal p27), W5 (having a (Gly$_4$Ser)$_3$ hinge region located between the p16 and p27 portions) and W6 (not having a (Gly$_4$Ser)$_3$ hinge region) were similarly generated. The nucleic acid and amino acid sequence of W5 are provided, respectively, in SEQ ID NO:7 and SEQ ID NO:8. The nucleic acid and amino acid sequence of W6 are provided, respectively, in SEQ ID NO:9 and SEQ ID NO:10.

In addition, a series of a series of truncated versions of p27 designed to increase the protein half-life were fused to full-length p16 at the N-terminus. In one p27 truncation, p27$_{12-178}$, the first 12 N-terminal and the last 20 C-terminal amino acids were removed from full length p27 to remove a CDK consensus phosphorylation site (TPKK) at amino acids 187–190, two other potential phosphorylation sites for proline directed kinases, at amino acids 178–181 (SPN), and a weak CDK phosphorylation site (SPSL) at amino acids 10–13 (Sheaff et al. (1997) *Genes & Dev.* 11:1464–1478; Morisaki et al. (1997) *Biochem. Biophys. Res. Commun.* 240:386–390). The nucleic acid and amino acid sequences of this truncated p27 protein (12aa–178aa) are shown in SEQ ID NO:11 and SEQ ID NO:12, respectively, which provide a polypeptide of the formula EcoRI-ATG-HA epitope-p27 (12–178aa)-Stop-NotI.

W7 comprises amino acids 12–178 of p27 fused to full length p16, where the p27 and p16 portions are separated by a (Gly$_4$Ser)$_3$ hinge region. The nucleic acid and amino acid sequence of W7 are provided, respectively, in SEQ ID NO:13 and SEQ ID NO:14. W8 comprises amino acids 12–178 of p27 fused to full length p16, where the p27 and p16 portions are not separated by a (Gly$_4$Ser)$_3$ hinge region. The nucleic acid and amino acid sequence of W8 are provided, respectively, in SEQ ID NO:15 and SEQ ID NO:16.

In a second truncation of p27, p27$_{25-93}$, only the CDK inhibitory domain of p27 (amino acids 25–93) was retained. This domain contacts both the CDK and cyclin binding subunits and is sufficient for kinase inhibition, while lacking the nuclear localization signal at amino acids 152–166 and the QT domain at amino acids 144–194 (Russo et al. (1998) *Nature* 395:237–243). Thus, the p27$_{25-93}$ CDKi was created to eliminate amino acid residues that may play a role in targeting the parental p27 molecule to the ubiquitin- proteosome degradation pathway or may play a role in p27 phosphorylation. The nucleic acid and amino acid sequences of this truncated p27 protein (25aa–93aa) are shown in SEQ ID NO:17 and SEQ ID NO:18, respectively, which provide a polypeptide of the formula EcoRI-ATG-HA epitope-p27 (25–93aa)-Stop-NotI.

Figures 4, 10A:
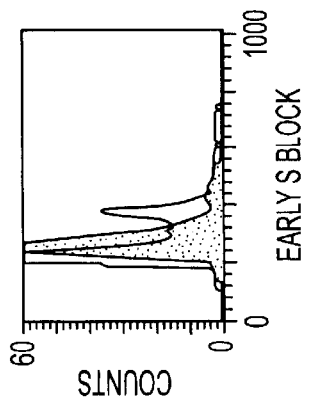
FIG. 10A shows a series of DNA histograms comparing CASMC's transduced with recombinant adenovirus encoding the various indicated CDKi or Null (i.e., AV-CMV) at 50 MOI. Twenty-four hours after transduction, virus was removed, and the cells were restimulated with 10% FBS-containing media. Three days later, the cells were fixed and stained with propidium iodide, and then subjected to FAC-scan analysis. Cells that were kept in 0.05% FBS for 48 hours (Serum Low) as well as cells that were treated with nothing (Mock Control), n-butyrate (early $G_1$ block), or aphidicolin (early S block) were also analyzed for DNA content as control profiles.
Figures 3, 10A:
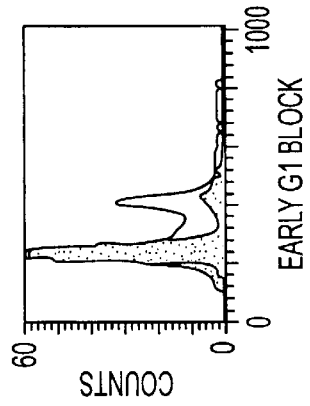
Figures 2, 10A:
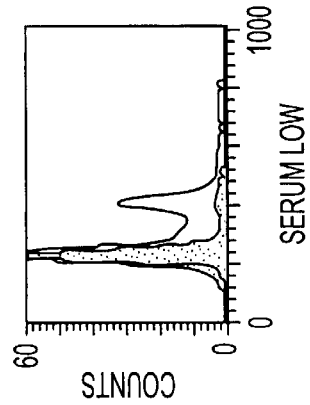
Figures 1, 10A:
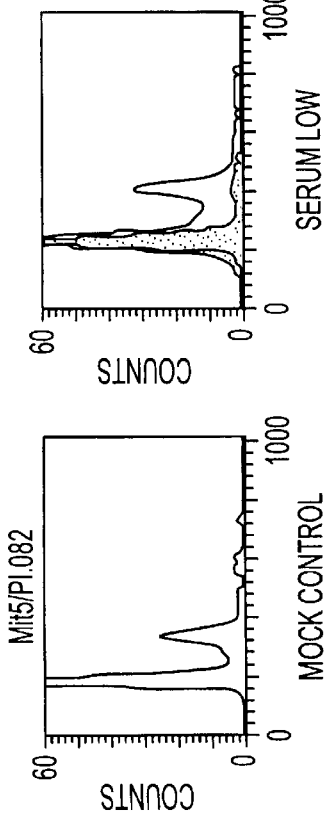
Figures 8, 10A:
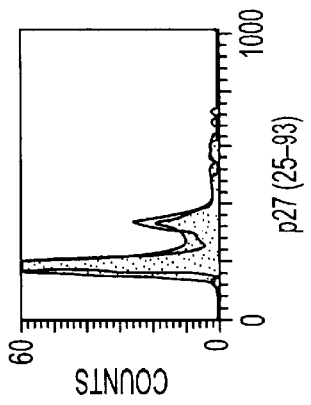
Figures 7, 10A:
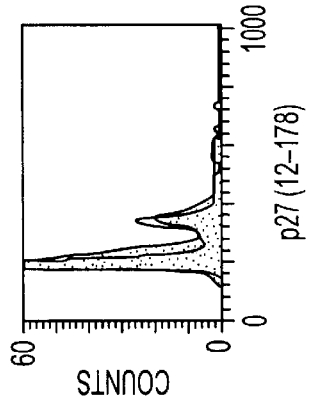
Figures 6, 10A:
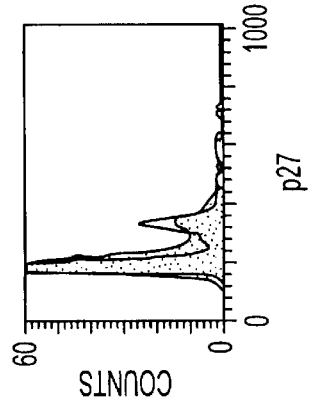
FIG. 6 is a diagrammatic representation showing representative, non-limiting recombinant CDK inhibitors of the invention tested in in vitro kinase assays. The p16 molecule is indicated by the open box; the p27 molecule and its derivatives are indicated by the hatched boxes; and the 15 amino acids long $(Gly_4Ser)_3$ linker between the p16 and p27 moieties is indicated by the black boxes. Above the schematic for each molecule is the corresponding 5' and 3' amino acid from the parental molecule. The table in the middle shows the $IC_{50}$'s (in nM) of the purified inhibitors as determined by in vitro kinase assays that utilized CDK4/cyclin D1, CDK2/cyclin E, and CDC2/cyclin B kinases. At the right of FIG. 6 is listed the estimated half-life of the adenovirus expressed CDKi protein (in hours) as measured by pulse-chase experiments.
Figures 5, 10A:
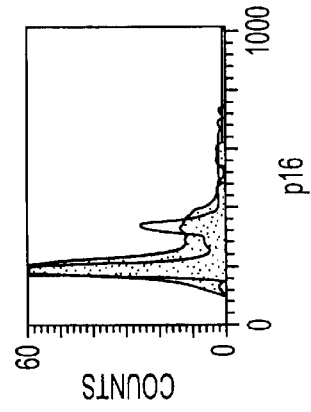

The p27$_{25-93}$ fragment were fused to the N-terminus of p16 with (W10) or without (W9) the (Gly$_4$Ser)$_3$ hinge (FIG. 6). The nucleic acid and amino acid sequence of W9 are provided, respectively, in SEQ ID NO:19 and SEQ ID NO:20. The nucleic acid and amino acid sequence of W10 are provided, respectively, in SEQ ID NO:21 and SEQ ID NO:22.

W3, W8, and W10 were further subcloned into a modified pGEX4T-1 plasmid (Pharmacia Biotech, Uppsala, Sweden) (where a NdeI cloning site was inserted between the BamHI and EcoRI sites) as NdeI-NotI fragments to generate glutathione S-transferase (GST) tagged fusion proteins. A similar strategy was used to generate fusion proteins without the (Gly$_4$Ser)$_3$ linker (i.e., W4 (p27-p16), W7 (p27$_{12-178}$-p16), and W9 (p27$_{25-93}$-p16)). The nucleic acid and amino acid sequences of the p27$_{25-93}$-p16 fusion CDKi, W9, without the HA tag and six histidine residues are provided in SEQ ID NO:23 and SEQ ID NO:24, respectively.

p27, p27$_{25-93}$, and p27$_{12-178}$ proteins were expressed in *E. coli* BL21 strain using the pT7 plasmids described above. For protein expression, cells were grown in LB+50 mg/ml ampicillin at 37° C. to OD$_{600}$=0.8 and protein expression was induced by IPTG (final; conc.: 20 mM) for 4 hours as 37° C. Cells were collected and the pellet was frozen at –80° C. The preparation of the cell lysate and binding to a Ni$^{2+}$ charged sepharose resin (Invitrogen Corp, San Diego, Calif.; Catalog No. R801) was done according to the manufacturer's instruction (Invitrogen; see also Hochuli et al. (1987) *J. Chromatography* 411:177–184; Janknecht et al. (1991) *Proc. Natl. Acad. Sci. USA* 88:8972–8976). The bound proteins were eluted with 50 mM, 200 mM, 350 mM, and 500 mM imidazol and the fractions were analyzed on SDS/PAGE. The 200 mM, 350 mM, and 500 mM imidazol fractions were collected, dialyzed against 1×PBS (1 mM KH$_2$PO$_4$, 10 mM Na$_2$HPO$_4$, 137 mM NaCl, 2.7 mM KCl, pH 7.4)+10% glycerol and stored at –80° C. in aliquots. Approximately 25% of the prep was the protein.

p27$_{25-93}$ and p27$_{12-178}$ were further purified by gel filtration column chromatography using a Superdex 75 FPLC column equilibrated with 10% glycerol in PBS. Expression and purification of the GST-tagged W3, W4, W7, W8, W9, and W10 fusion proteins was essentially as described (Gyuris et al. (1993) *Cell* 75:791–803). The purified GST-fusion proteins were then buffer exchanged by dialysis into 50 mM Tris-HCl pH 8.0, 150 mM NaCl, 2 mM CaCl$_2$. The GST domain was removed from the proteins by enzymatic cleavage with 1 unit (USB units) of thrombin/mg of protein/hour (thrombin commercially available from USB). Following cleavage, the thrombin was inactivated with 2 fold molar excess of PPACK (USB). The cleaved GST moiety was then removed by passing the protein solution over a column of glutathione-Sepharose. Protein concentration was determined using a protein assay (BioRad, Cambridge, Mass.) with bovine serum albumin (BSA) as a standard. In order to more accurately determine the concentration and purity of the specific proteins in each of the preparations, the protein samples were subjected to SDS-PAGE, and stained with Coomasie blue. The stained gels were analyzed using the Gel Doc 1000 image analysis system and Molecular Analyst software (BioRad).

The p27 and p16 CDKi's appear to fold correctly in all of the fusion protein CDKi's, as the biochemical data indicates that the p27 moieties were functional and intra-cellular staining with anti-p16 antibodies indicate that at least at a gross level, the p16 molecules were folded correctly.

EXAMPLE II in vitro Kinase-Inhibiting Activities of the p27/p16 Fusion Proteins

The natural substrates for p27 and p16 CDKi's are cyclin-dependent kinase (CDK) complexes that are formed via the association of different catalytic CDK and regulatory cyclin subunits. The CDK4/cyclin D and CDK6/cyclin D complexes regulate progression through G$_1$ phase, the CDK2/cyclin E kinase regulates the G$_1$/S transition, the CDK2/cyclin A complex drives the cells through S-phase, and the entry and exit from mitosis is controlled by the CDC2/cyclin B complex (Sherr, C. J. (1996) *Science* 274:1672–1677). CDKi's regulate the activity of the CDK complexes through a combination of phosphorylation events and physical association (Morgan, M. (1995) *Nature* 374:131–134). The redistribution of CDKi's between the different CDK/cyclin complexes during the cell cycle coordinates the timing of activation and de-activation of their kinase activity (Sherr and Roberts (1995) *Genes and Dev.* 9:1149–1163).

To determine the ability of the CDKi proteins of the invention, their abilities to inhibit the in vitro kinase activity of CDK4/cyclin D1, CDK2/cyclin E, and CDC2/cyclin B complexes was determined. The purity of the various p$^{27}$-p16 fusion proteins, p27, and p16 preparations were normalized using p16 and p27 specific antibodies.

Active CDK4/cyclin D1, CDK2/cyclin E, and CDC2/cyclin B complexes were obtained from Sf9 insect cells transfected with baculoviruses expressing recombinant cyclins and CDK's. Briefly, the assay employed Sf9 cell extracts that were made from cells that were coinfected with the proper CDK and cyclin expression constructs. Typically, 44 mg of Sf9 extract in 50 ml of 50 mM Tris-HCl pH 7.6, 10 mM MgCl$_2$, 1 mM DTT, 25 mM ATP, 10 mCi $^{32}$P-γ-ATP was used in the absence or the presence of the particular inhibitor (inhibitor concentration was between 25 nM to 1 mM). Partial purification of CDK4/cyclin D1 was achieved by a 20–40% ammonium sulfate preparation of the cell lysate and was used in the assays. CDK2/cyclin E was purified to greater than 90% and pretreated with CDK-activating kinase (CAK) (Morgan, M., supra) for full activation. CDC2/cyclin B was expressed as a GST fusion protein (CDC2/GST-cyclin B) and purified on glutathione-Sepharose column, cleaved by thrombin, and followed by another glutathione-Sepharose separation for the removal of the cleaved GST. GST-fused Rb (glutathione S-transferase fusion with amino acids 379–928 from the C terminus of pRB; GST-Rb) was used as a substrate for the CDK4/cyclin D1 and CDK2/cyclin E assays; histone H1 was the substrate for CDC2/cyclin B. The reaction was carried out at 30° C. for 30 minutes using 2 mg of substrate. These assays were carried out in 96 well plates (Nunc, Naperville, Ill.) and monitored by γ-$^{32}$P-ATP incorporation.

The reactions were initiated by addition of the insect cell-produced CDK (e.g., CDC2/cyclin B) and the *E. coli*- produced CDKi (e.g., p27 and W9). The concentrations of GST-Rb and histone H1 were 4.4 mM and 19 mM, respectively, and the concentration of ATP was 50–60 mM. The reaction mixtures contained 50 mM Tris-Cl pH 7.5, 10 mM $MgCl_2$, and 1 mM DTT in a total volume of 50 or 100 µl. After incubation at 30° C. for 10–20 minutes, the reaction was terminated by the addition of a stop solution containing EDTA. The phosphorylated substrates were captured either by GST-Sepharose or TCA precipitation and then monitored for radioactivity (Microplate Scintillation Counter, Packard, Meriden, Conn.).

The concentration of CDKi protein at which 50% of the kinase activity was blocked ($IC_{50}$) was calculated for various cyclin/CDK pairs. The results are indicated in Table I and in FIG. 6, the latter showing three columns labeled CDK4/cyclin D1 (nM), CDK2/cyclin E (nM), and CDC2/cyclin B (nM). Moreover, the inhibition constant, $K_i$ for the inhibition of CDK4/cyclin D1 by p27/p16 fusion protein was determined to be 23 nM, compared to a $K_i$ of 75 nM for p16 inhibition of the same CDK4 complex.

TABLE I

Inhibition of Cyclin Dependent Kinase Complexes by p27-p16 Fusion Protein

| inhibitor | CDK4/ cyclin D1 | CDK2/ cyclin E | CDK2/ cyclin A | cdc2/ cyclin B |
|---|---|---|---|---|
| p27-p16 | 25 nM | 30 nM | 25 nM | 15 nM |
| p27 | 63 nM | 52 nM | 65 nM | 20 nM |
| p16 | 250 nM | >500 nM | >500 nM | >500 nM | nM = nanomolar

As shown in Table I and FIG. 6, p16 was a potent inhibitor of the CDK4/cyclin D1 kinase. In contrast, p27 was a powerful inhibitor of all three kinase complexes. The various p27 modifications did not positively impact the monomeric or fusion protein CDKi's inhibitory activity in vitro (see FIG. 6). In general, the order of the p16 and p27 CDK in the fusion CDKi does not appear to impact the activity of the fusion CDKi. Moreover, the $(Gly_4Ser)_3$ hinge region is not necessary to retain p27 function in the fusion CDKi.

Thus, in vitro kinase inhibition experiments indicated that the potency of the purified $p27_{12-178}$, $p27_{25-93}$ or the fusion p27/p16 proteins (W3, W4, W7, W8, W9, anid W10) were not appreciably different from that of full-length p27 or an equimolar mixture of p16 and p27. The activity of the CDK4/cyclin D1 complex was inhibited by both p16 and p27.

EXAMPLE III

Figure 7:
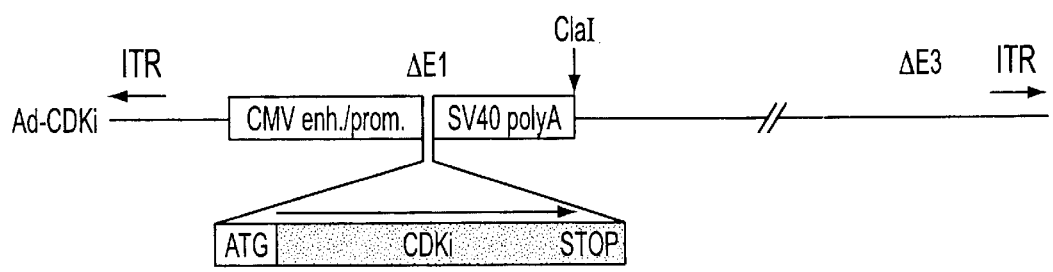
FIG. 7 is a diagrammatic representation of the genomic structure of a representative, non-limiting recombinant adenovirus that expresses a CDKi of the invention. The expression of the inhibitors is regulated by the CMV enhancer and promoter and the SV40 poly A sequence. The ATG is in the context of the optimal Kozak sequence.

Construction of Recombinant Adenoviruses Expressing p16. p27. and the p27/p16 Fusion Proteins Based on the in vitro kinase data, a representative of each of the CDKi species was selected for further analysis. The genes encoding p16, p27 and its derivatives, W3, W7, or W9 CDKi were introduced into the E1 region of a replication deficient, E1 and E3 deleted (ΔE1/ΔE3) recombinant adenovirus (FIG. 7). The adenovirus vector system used for the construction of replication deficient, E1 region- and E3 region-deleted, E4 region-containing adenovirus 5 (Ad5) recombinants was purchased from Microbix Biosystems Inc. (Toronto, Ontario, Canada). The six-his residue, HA-tagged CDKI's were expressed under the control of the CMV promoter/enhancer and the SV40 polyA signal (FIG. 7).

The ΔE1/ΔE3 adenovirus encoding p27 (AV-p27) was constructed by in vivo recombination in 293 cells following the manufacturer's instructions (Microbix). 293 cells, a human embryonic kidney cell line which contains the E1 region of the adenovirus and, therefore, provides the E1 region gene products lacking in the E1-deleted recombinant adenoviruses, are commercially available from the American Type Culture Collection, Manassas, Va. (ATCC No. CRL 1573) (Graham et al. (1977) J. Gen. Virol. 36:59–72). AV-p27 DNA was isolated from the amplified virus and digested with ClaI. This digest removed the p27 expression cassette (i.e., nucleic acid sequence encoding p27 operably linked to regulatory sequences) and the left inverted terminal repeat (ITR) and packaging signals of Ad5 (see FIG. 7). HA-tagged p16, $p27_{25-93}$, $p27_{12-178}$, W3, W7, and W9 molecules were cloned into a plasmid, pKS-ITR-CMV, which contains the expression cassette as well as the left ITR and packaging signals with flanking EcoRV and ClaI restriction sites. The order of the functional elements is the following from 5' to 3': EcoRV-left ITR-packaging signal-CMV enhancer/promoter-CDKi insert-SV40 polyA-ClaI. The EcoRV-ClaI fragments containing the CDKi inserts were ligated to the deleted, large Ad5 DNA in vitro and the ligated DNA was transfected into 293 cells.

Infectious, recombinant virus particles were rescued from 293 cells. The unligated, large Ad5 fragment was unable to generate infectious viruses alone because of the lack of the left ITR and packaging signal that are essential for virus replication. Infectious recombinants formed only when the small EcoRV-ClaI fragment containing the left ITR, packaging signal, the expression cassette and the CDKi insert was ligated to the ClaI digested end of the Ad5 DNA re-creating an infectious Ad5 recombinant virus DNA.

EXAMPLE IV

Stability of p16, p27,and the p27/p16 Fusion Proteins Delivered by an Adenovirus Containing the Entire E4 region To determine the half-life of the various CDKi in CASMC's, pulse-chase experiments were performed using growth arrested and proliferating CASMC's transduced with the adenoviruses containing the entire E4 region and expressing the various CDKi (AV-CDKi's).

Human coronary artery smooth muscle cells (CASMCs) were obtained from Clonetics (Walkersville, Md.). Low passage CASMC (less than passage 10) were plated at 3500 cells/$cm^2$ in complete SMC media (Clonetics, plus 5% FBS and growth factors) and allowed to recover overnight. For proliferating cells, cultures were maintained throughout in complete SMC. For quiescent cells, cultures were serum starved for 48 hours in low serum media (SMC media with 0.05% FBS and 1:100 growth factors).

Growth arrested ($G_0$) and proliferating ($A_s$) CASMC were transduced at an MOI of 50 with the various recombinant adenoviruses containing the E4 region and expressing CDKi's. Twenty-four hours later, the cells were radiolabeled ("pulsed") for 2 hours in media containing $^{35}S$-methionine. The $^{35}S$-methionine containing media was then removed and replaced with media containing an excess of non-radiolabeled amino acids, and the cells "chased" for 0, 1, 3, 9, 18 hours and 0, 1, 2, 3, 4, and 5 days. Cell pellets were lysed in 50 mM Tris-Cl pH 7.5,250 mM NaCl, 0.5% NP-40, 50 mM NaF, 5 mM EDTA, 1 mM PMSF, 1 mM Sodium Vanadate, and protease inhibitors. Protein concentrations were determined using a protein assay (Biorad) with bovine serum albumin (BSA) as a standard. Equivalent amounts of total protein from the cells were then immunoprecipitated using antibodies bound to protein A-sepharose. The antibodies used were p27 (Kip1, commercially available from Transduction Laboratories, Lexington, Ky.), and p16-C20 (commercially available from Santa Cruz Biotech., Santa Cruz, Calif.). The immunoprecipitates were separated by SDS-PAGE, and the gels vacuum dried and exposed to film. Estimated half life was determined from the radiolabeled proteins on the autoradiographs, which were analyzed using the Gel Doc 1000 image analysis system and Molecular Analysts software (Biorad).

The observed molecular weights of the expressed, HA epitope tagged proteins corresponded to the expected sizes: p27, approximately 30 kD; $p27_{12-178}$, approximately 28 kD; $p27_{25-93}$, approximately 10 kD; p16, approximately 19 kD; W3, approximately 48 kD; W7, approximately 46 kD; and W9, approximately 30 kD. Interestingly, in AV-$p27_{25-93}$ infected cells, a protein band with the apparent molecular weight of approximately 24 kD was observed. The band was recognized by both p27 and HA epitope specific antibodies (data not shown) suggesting that it might be a stable dimer of two $p27_{25-93}$ molecules.

The kinetics of signal decay from the immunoprecipitated CDKi's was assessed by autoradiography at specific time-points (summarized in FIG. 6, two far right columns labeled "Half-Life (hrs)"). The half-life of the CDKi's was estimated as the time-point at which half the original CDKi protein signal remained. The half-lives of adenovirus expressed p27 and p16 were similar, approximately 3 hours in quiescent cells. The half-lives of the truncated p27 derivatives were reduced compared to the full-length p27 molecule. The half-life of $p27_{12-178}$ was approximately 2 hours in quiescent cells and approximately one hour in proliferating cells. The $p27_{25-93}$ was extremely unstable with a half-life of less than one hour in CASMC's. The half-lives of the fusion protein CDKi, W3 and W9, were similar to the p27 molecule: approximately two hours in quiescent cells ($G_0$ cells) and approximately 6.5 and 4.5 hours, respectively, in proliferating cells. While the half-life of the W7 fusion protein was similar to the other CDKi in growth arrested SMC, it demonstrated a strikingly longer half live in pro-liferating cells (approximately 20 hours). This represented an increase of at least 6-times and 20-times in stability over the contributing p16 and $p27_{12-178}$ molecules, respectively.

In quiescent CASMC ($G_0$ cells), the p16, p27, W3, W7, and W9 proteins all had half-lives of 2 to 3 hours (see FIG. 6). In proliferating cells ($A_s$), the W7 protein demonstrated a half-life of 20 hours.

EXAMPLE V

Efficacy of the Recombinant Adenoviruses Encoding CDKi in Transducing Cells of the Vasculature To evaluate transduction efficiency of cells of the vasculature by ΔE1 deleted adenovirus, cultures of quiescent primary coronary artery smooth muscle cells (CASMC), aortic smooth muscle cells (AoSMC), coronary artery endothelial cells (CAEC), and control HeLa cells were incubated with increasing does of a ΔE1 adenovirus encoding the β-gal transgene. Human coronary artery smooth muscle cells (CASMC) and aortic smooth muscle cells (AoSMC) were obtained from Clonetics (Walkersville, Md.) and maintained in SMC media (Clonetics) supplemented with 5% fetal bovine serum (FBS). Human coronary artery endothelial cells (CAEC) were obtained from Clonetics (Walkersville, Md.) and maintained in EBM media supplemented with 5% bovine serum and growth factor supplements recommended by Clonetics. HeLa cells were maintained in DMEM containing 10% FBS.

Quiescent CASMC, AoSMC, CAEC or HeLa cells were seeded at confluency in the appropriate media containing 5% FBS and the cells were infected 24 hours later with ΔE1-deleted AV-CMV-Lac-Z at MOI of 10, 30 and 100. The next day, virus was removed and replaced with fresh media. The cells were harvested 4 days later, and the β-gal positive cells were detected using fluorescein di-b-D-galactopyranoside (FDG) substrate (Sigma, St. Louis, Mo.) and quantified by FACS analysis.

Figure 8A:
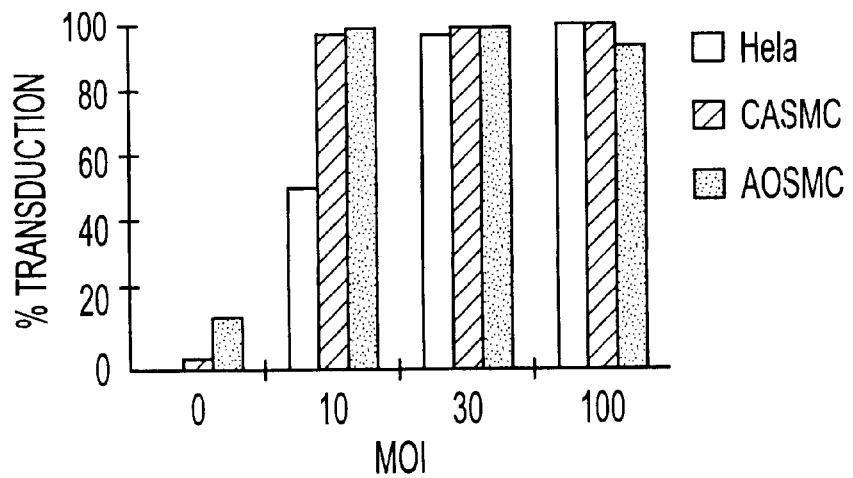
FIG. 8A is a graphic representation showing the transduction efficiency of smooth muscle cells with recombinant adenovirus expressing LacZ operably linked to the CMV promoter. Nonproliferating human aortic smooth muscle cells (AoSMC), CASMC, or HeLa cells were either mock treated or transduced with Ad-CMV-Lac-Z at MOI of 10, 30 and 100. Five days later, the percentage β-gal positive cells were determined by flow cytometry following staining with FDG substrate (Sigma). Both AoSMC and CASMC showed greater than 95% transduction efficiency at all the MOI tested.
Figure 8B:
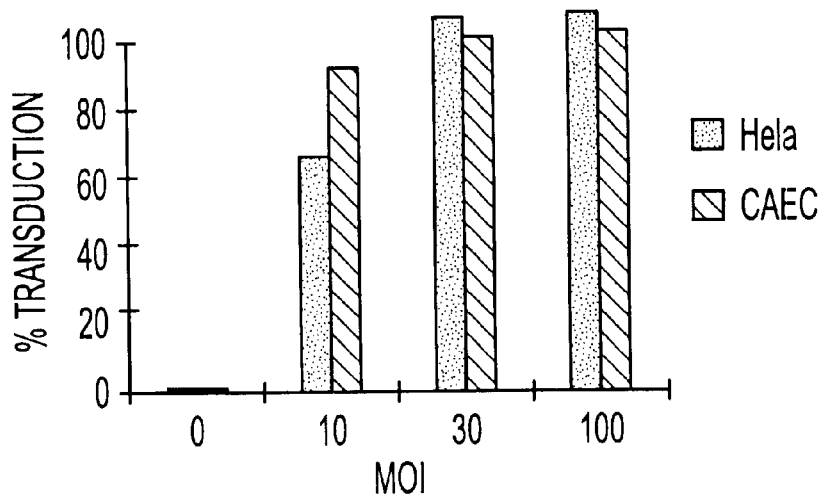
FIG. 8B is a graphic representation showing the transduction efficiency of endothelial cells with recombinant adenovirus expressing LacZ operably linked to the CMV promoter. Nonproliferating human coronary artery endothelial cells (CAECs) or HeLa cells were either mock treated or transduced with AV-CMV-Lac-Z at MOI of 10, 30 and 100. Two days later, the percentage of β-gal positive cells was determined by flow cytometry following staining with FDG substrate (Sigma). CAEC showed greater than 90% transduction efficiency at all the MOI tested.

Non-proliferating human CASMC, AoSMC and CAEC were readily transduced with transduction efficiencies approaching 100% at an MOI of 10 as shown in FIGS. 8A and 8B. Similar results were obtained with proliferating CASMC, AoSMC, and CAEC.

EXAMPLE VI

Inhibition of Smooth Muscle Cell Growth by CDK Inhibitors

For the growth inhibition studies with growth arrested (i.e., synchronously growing) cells, CASMC's were seeded at 1.3 or $3 \times 10^4$ cells/well in 24 well plates in the appropriate media supplemented with 5% FBS. Twenty-four hours later, the media was changed to low serum conditions (media with 0.05% FBS) to growth arrest the cells. After 48 hours, cells were infected in low serum conditions with adenoviruses encoding the CDK inhibitor (AV-CKI) transgene or trans-gene encoding no protein (AV-CMV, which contains only the CMV promoter) at MOI's of 1, 10, 50, 100 and 250 in duplicate wells. After 24 hours, virus was removed and fresh media containing 10% FBS was added back. The cells were harvested three days later and counted to determine cell recovery, or evaluated for DNA content. Apoptosis was assessed by TdT assay (Phoenix Flow Systems, San Diego, Calif.) and annexin binding assay (R&D Systems, Minneapolis, Minn.).

Figure 9:
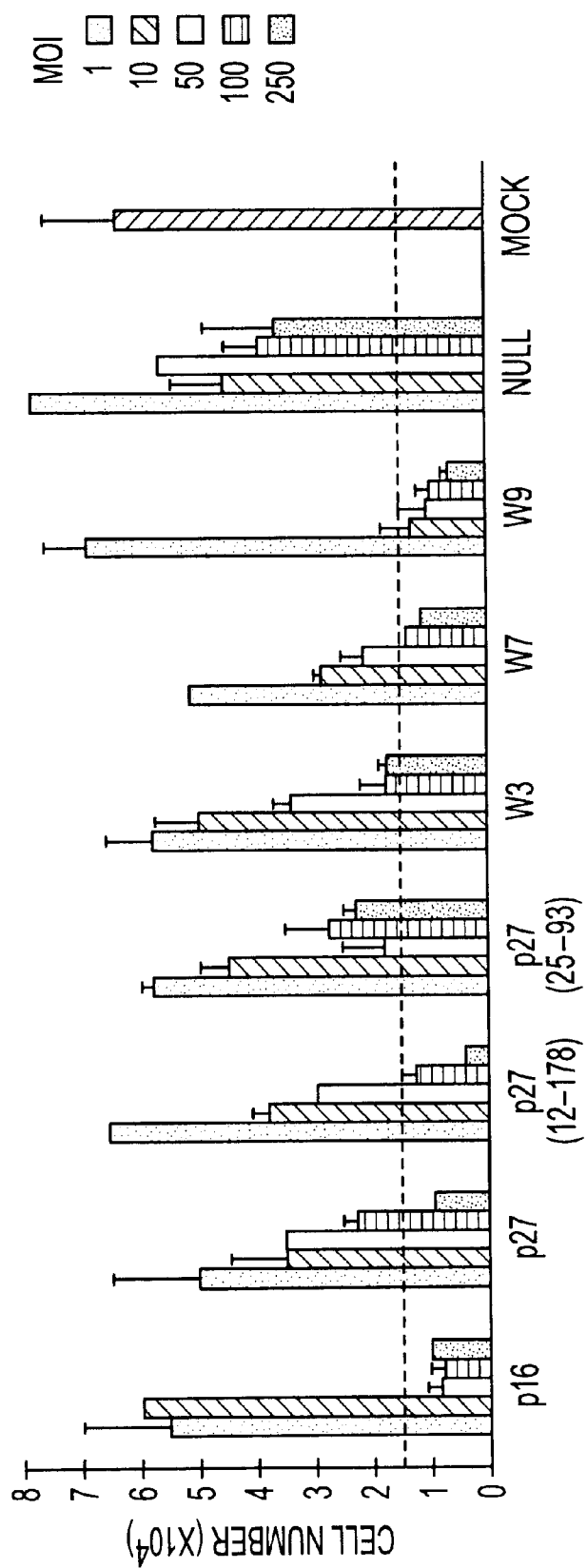
FIG. 9 is a graphic representation showing the inhibition of cell growth of synchronously growing CASMC by various AV-CDKi. CASMC's were made quiescent by incubation in low serum conditions and transduced with the indicated AV-CDKi's at MOI's of 1 to 250. The next day, cells were stimulated to enter the cell cycle by addition of 10% serum to the media. Cells were harvested 3 days after restimulation with serum-containing media and counted from duplicate wells. The dashed line represents starting cell number.

Uninfected synchronized CASMC underwent approximately a 6-fold expansion in a three day period (FIG. 9). AV-W9, encoding the $p27_{25-93}$-p16 fusion protein, was the most potent inhibitor of vascular smooth muscle cells, and demonstrated complete CASMC growth arrest at an MOI of 10, which coincided with the MOI sufficient to achieve complete adenovirus transduction of a population of CASMC (FIG. 9). AV-W7, which encodes the $p27_{12-178}$-p16 fusion protein, demonstrated complete inhibition of syn-chronized CASMC at a 5 to 10 fold higher MOI. The extent of inhibition with AV-p27, AV-$p27_{12-178}$, and AV-$p27_{25-93}$ was similar to AV-W3.

At an MOI of 50, transduction with AV-p16 resulted in a complete blockade of CASMC proliferation (FIG. 9). There was, however, some variability in relative activities of p16 and p27 from CASMC donor to donor. This inhibition profile may indicate the existence of a threshold mechanism of p16 inhibition that is operative in vivo. In all experiments involving CASMC, AV-W9 was the most active anti-proliferative agent. In this experiment, AV-p16 showed an inhibitory effect at MOI of 50 (FIG. 9). AV-W7, which encodes the $p27_{12-178}$-p16 fusion protein, demonstrated complete inhibition at 100 MOI. AV-W9 had the strongest effect in blocking cell growth following infection in quiescent CASMC. The virus particle to plaque forming units for AV-p16, AV-p27, AV-W7 and AV-W9 were similar (305 vp/pfu, 267 vp/pfu, 141 vp/pfu and 197 vp/pfu respectively). The primacy of AV-W9 was observed in three independent experiments in which CASMC from three different donors were tested (data from one experiment is shown in FIG. 9). Some variation was observed from donor to donor in the relative strength of inhibition by AV-p16 or AV-p27 alone. In all donors, however, AV-W9, AV-W7, and AV-W3 had inhibitory effects. Importantly, the effect of AV-W9 was clearly cytostatic and not cytocidal since CDKi induction of SMC apoptosis was not observed as assayed by annexin and propidium iodide staining and analyzed by FACS.

EXAMPLE VII

AV-W9 Transduction Induces a Blockage of Smooth Muscle Cells in G1 Phase and a Loss of Cells in S Phase The point in the cell cycle in which the AV-CDKi's transduced CASMC were growth arrested was determined by quantification of the cellular DNA content by FACS analysis. CASMC were transduced with AV-CDKi. Three days after restimulation, cells were washed once with PBS and fixed in 70% EtOH for at least 4 hours. Cells were then washed once with PBS and treated with 0.1% triton X-100, 200 μg/ml RNase A and 50 μg/ml propidium iodide in PBS at 37° C. for 15 minutes. Cells were analyzed on FACscan using Cell Quest software (Becton Dickinson, Santa Clara, Calif.). Cell cycle analyses were performed using ModFit LT software (Verity, Topsham, Me.). As controls for cell cycle analysis, cells were treated with n-butyrate or aphidicolin, which arrest cells in early $G_1$ (Darzynkiewicz et al. (1981) *Exp. Cell. Res.* 136(2):279–293) or early S phase (Sorscher and Cordeiro-Stone (1991) *Biochemistry* 30(4):1086–1090), respectively. 5 mM n-butyrate or 5 mg/ml aphidicolin was added to SMC at the time of restimulation, and cells were collected 36 hours later for analysis of DNA content.

Following incubation in low serum conditions, greater than 98% of SMC were synchronized in the $G_0/G_1$ phase (FIG. 10A, top panel, Serum Low). This block was similar to cells treated with n-butyrate, which blocks cell cycle progression in the early $G_1$ phase and entry into S phase of the cell cycle (Kruh, J. (1982) Mol Cell Biochem 42:65–82) (FIG. 10A, top panel, Early $G_1$ Block). Upon stimulation of the synchronized CASMC with complete media, the normal profile of cells in $G_0/G_1$ phase, S phase and $G_2/M$ phase was observed; 71%, 18% and 11%, respectively (FIG. 10A, top panel, Mock Control).

As predicted from the experiments shown in FIG. 9, transduction with AV-W9 had a profound effect on the cell cycle of CASMC. CASMC transduced with the AV-W9 at MOI of 10 showed complete block of entry into the $G_2/M$ phase; >1% for AV-W9 as compared to 11% in Mock (FIG. 10A; W9, compared gray FACS to mock control solid line overlay). At lower MOI, transduction with AV-W9 initially induced an increase in the population of cells in S phase (47%) (FIG. 10B, middle panel), similar to that observed with the aphidicolin treatment which blocks cells in early S phase (FIG. 10A, top panel, Early S Block). At higher MOI of 50 and 100, however, the percentage of cells in S phase decreased and the fraction of CASMC arrested in $G_0/G_1$ phase increased to over 80% (FIG. 10B, lower panel). A similar pattern of growth arrest was observed with the AV-W7 transduced cells but at five-fold higher MOI. Transduction with "empty" adenovirus, which demonstrated only modest inhibition of CASMC proliferation (FIG. 10A, Null), similarly had little effect on reducing the population of cells in $G_2/M$ even at MOI of greater than 100 (FIGS. 10A and 10B, Null). The AV-p27, AV-p27$_{12-178}$, AV-p27$_{25-93}$, and AV-W3 induced a depletion of the $G_2/M$ population and a corresponding increase in the percentage of cells in S phase, although at MOI's 10 to 100 fold higher than necessary for AV-W9.

Thus, as might be expected from the anti-proliferative activity date, the W9 and W7 CDKi's were readily distinguished in analysis of their impact on CASMC cell cycle progression. Transduction of CASMC with any of the AV-p27-p16 fusion CDKi's as well as AV-p27 and AV-p27 derivatives lead to blockade of cells in S phase and loss of the cells in $G_2/M$ phase. Transduction with AV-W9, however, led to blockade of cells in $G_1$ phase and loss of the cells in S phase. At higher MOI's AV-W7 produced a similar effect. This raises the possibility that at lower concentrations W9 and W7 primarily block CDK's whose activity is required for S-phase progression (CDK2/cyclin E or CDK2/cyclin A) and at higher concentrations, block the activity of CDK's whose activity is required in $G_1$ and at $G_1$/S (Cdk4, 6/cyclin D and Cdk2/cyclin E).

EXAMPLE VIII

Inhibition of Endothelial Cell Growth by CDK Inhibitors

For the growth inhibition studies with growth arrested (i.e., synchronized) cells, CAEC's were seeded at 1.3 or $3 \times 10^4$ cells/well in 24 well plates in the appropriate media supplemented with 5% FBS. Twenty-four hours later, the media was changed to low serum conditions (media with 0.05% FBS) to growth arrest the cells. After 48 hours, cells were infected in low serum conditions with adenoviruses encoding the CDK inhibitor (AV-CKI) transgene or transgene encoding no protein (AV-CMV; "AV-Null") at MOI's of 1, 10, 50, 100 and 250 in duplicate wells. After 24 hours, virus was removed and fresh media containing 10% FBS was added back. The cells were harvested 3 days later and counted to determine cell recovery, or evaluated for DNA content.

For growth inhibition studies with proliferating (i.e., asynchronous) cells, CAEC were plated at $5 \times 10^4$ per well in six-well plates. After 24 hours, cells were infected with 10 MOI AV-CDKi or AV-CMV. Cells were harvested two days later and counted to determine cell growth. Apoptosis was assessed by TdT assay (Phoenix Flow Systems, San Diego, Calif.) and annexin binding assay (R&D Systems, Minneapolis, Minn.).

Figure 11A:
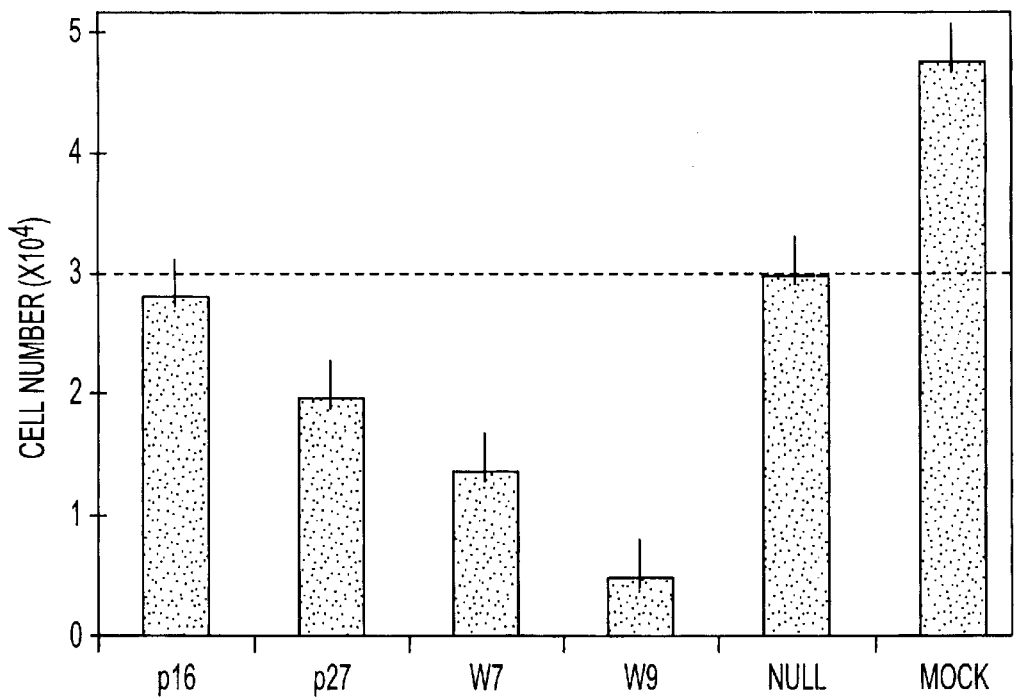
FIG. 11A is a graphic representation showing the inhibition of cell growth of synchronously growing CAEC by various AV-CDKi. Quiescent CAEC's were transduced with AV-CDKi at 10 MOI. The next day, virus was removed, and the cells were stimulated to enter the cell cycle by addition of 10% serum to the media. Cells were harvested 3 days later and counted. The dashed line represents starting cell number at time of transduction.
Figure 11B:
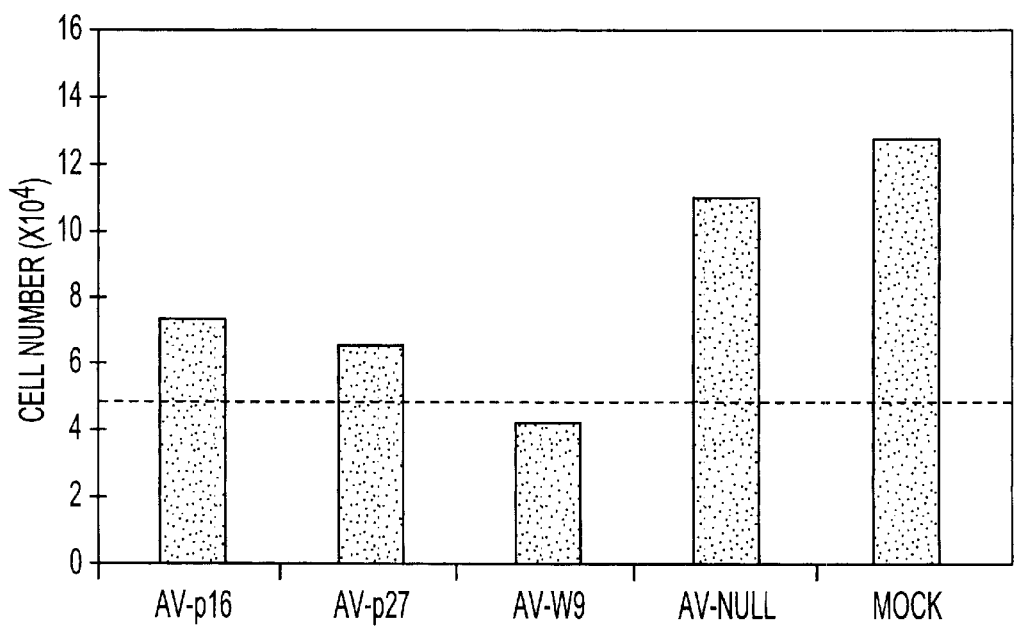
FIG. 11B is a graphic representation showing the inhibition of cell growth of asynchronous CAEC by various AV-CDKi. CAEC's were seeded in 6 well dishes and transduced the next day with indicated AV-CDKi at 10 MOI. Virus was removed on the following day, and the cells returned to full serum containing media. Cells were harvested 2 days later and counted. The dashed line represents starting cell number at the time of transduction.
Figure 12A:
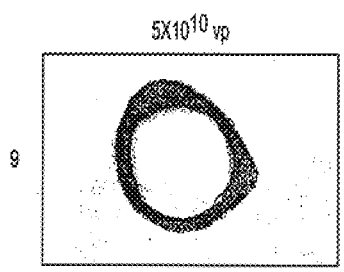
Figure 12B:
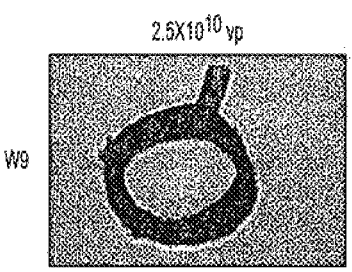
Figure 12C:
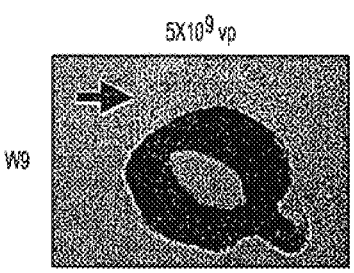
Figure 12D:
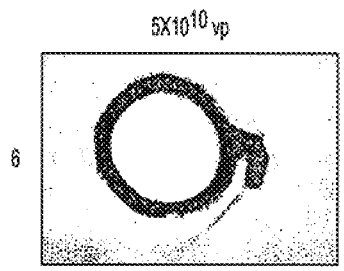
Figure 12E:
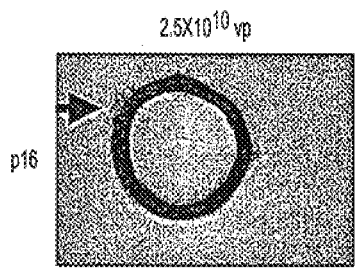
Figure 12F:
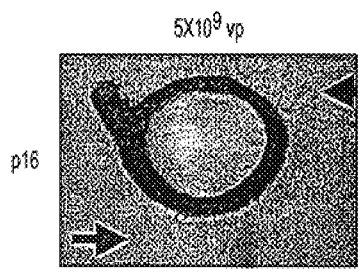
Figure 12G:
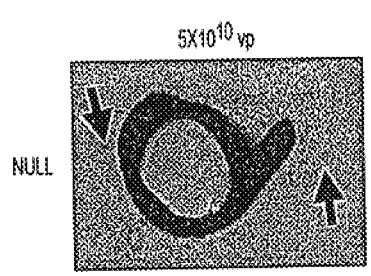
Figure 12H:
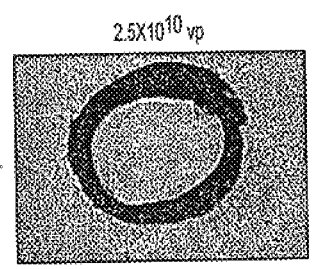
Figure 12I:
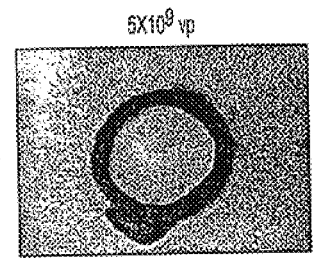

AV-W9 was observed to be the most potent inhibitor of endothelial cell proliferation using primary CAEC that had been growth arrested following serum deprivation (FIG. 11A). In these experiments however, AV-W9 not only inhibited cell proliferation, but also resulted in cell loss. The empty adenoviral vector (Null) induced less significant cell losses. When the experiment was repeated with proliferating endothelial cells that had not been growth arrested, W9 inhibited CAEC proliferation, while the AV-p16 and AV-CMV viruses had little effect (FIG. 11B). As observed with the SMC, there was not evidence of apoptosis following infection in either synchronized or proliferating EC as determined by Tunnel staining of DNA fragments or by annexin binding. Similar results were obtained with human aortic endothelial cells.

EXAMPLE IX

Adenovirus-Delivered CDKi Have Angiogenesis-Inhibiting Activity as Measured by the Aortic Ring Sprouting Assay Because AV-CDKi of the invention inhibited the growth of not only vascular smooth muscle cells, but also vascular endothelial cells, two of the AV-CDKi, AV-W9 and AV-p16, were tested for an angiogenesis-inhibiting activity. One standard method for measuring angiogenesis activity is the aortic ring sprouting assay (Villaschi and Nicosia (1993) Am. J. Pathol. 143(1):181–90). In this assay, a ring of tissue from the aorta of a rat is cultured for seven days in endothelial cell growth media on a substrate, such as matrigel, which promotes angiogenesis activity. Under these conditions, the ring of tissue will sprout visible microvessels. Because a reagent having angiogenesis-inhibiting activity will prevent ring sprouting, this assay was used to detect any angiogenesis-inhibiting activity in the AV-CDKi of the invention.

One day before the experiment, 2 ml pipets, 24 well plates, and tubes were placed in refrigerator at 4° C. MATRIGEL (Cat# 40234B; Becton-Dickinson, San Jose, Calif.), which is stored at −20° C., was thawed at 4° C. overnight on ice and kept on ice before use.

On the day of the experiment, a cooled 2 ml pipet was used to mix the MATRIGEL basement membrane matrix to homogeneity. Keeping the culture plates on ice, 300 µl of MATRIGEL was added to gel in each well of a 24 well plate. The MATRIGEL-containing plate was then incubated at 37° C. for 30 min. Meanwhile, aortas were isolated from 4–6 week old rats and placed in Hank's solution (Cat# 14025-092, Gibco-BRL, Gaithersburg, Md.) to clean off the outer fat with tweezers. The outer fat-free aortas were next rinsed several times to remove blood and debris. Finally, the aortas were sliced into very thin rings using a scalpel on a dry dish.

Each aortic ring was then either transduced with AV-p16, AV-W9, or AV-Null (which has no insert, but has the CMV promoter) using $5 \times 10^{10}$ viral particles, $2.5 \times 10^{10}$ viral particles, or $4 \times 10^9$ viral particles. The aortic ring was transduced with in 50 µl PBS for 10 to 60 minutes at 37° C.

Following transduction, the transduced aortic rings were placed onto gelled MATRIGEL in the wells of the 24 well plate (which gelled at incubation for 30 minutes at 37° C.). 200 µl MATRIGEL was then added to seal the ring in place when the plate was cooling on ice. One ml of serum-free endothelial cell growth media (Culture Medium—EGM-2 (or EGM) Bullet Kit; Cat# CC-3162, Clonetics, Walkersville, Md.) was added to each well.

One ml of serum-free endothelial cell growth media was added to each well. The ring-containing plates were incubated at 37° C. for seven days.

The incubated rings were next fixed with 1% glutaradehyde in PBS at room temperature for 20 min and stained with Diff Quick staining Solution II (Cat# B4132-12; VWR, Chester, Pa.) for 10 min. at room temperature. The ring sprouting was recorded with a digital camera.

Figures 9, 10, 10A, 11, 12:
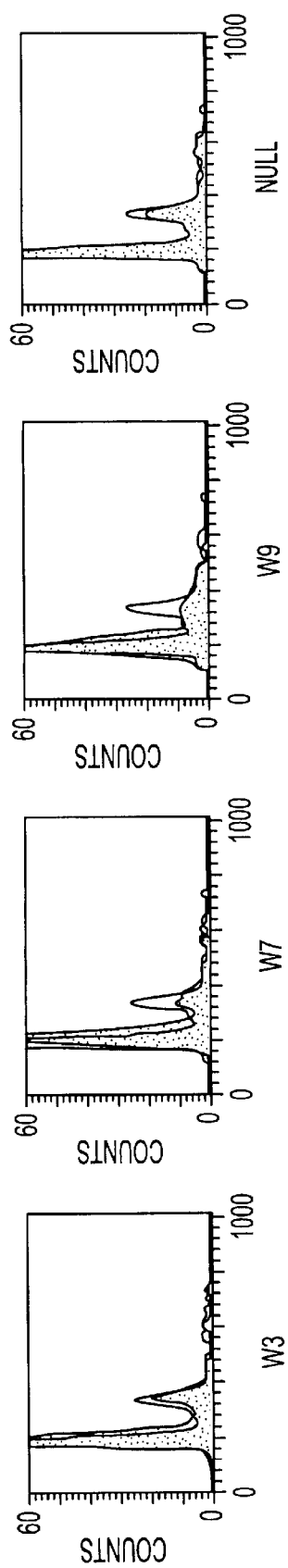
FIG. 12 is a representation of nine photographs showing the angiogenesis-inhibiting effects of AV-W9 and AV-p16 in the aortic ring sprouting assay. Aortic rings prepared from 4–6 week old rats were transduced with AV-CMV ("NULL"), AV-p16, and AV-W9 with $5 \times 10^{10}$ viral particles, $2.5 \times 10^{10}$ viral particle, and $5 \times 10^9$ viral particles.
Figures 1, 10B:
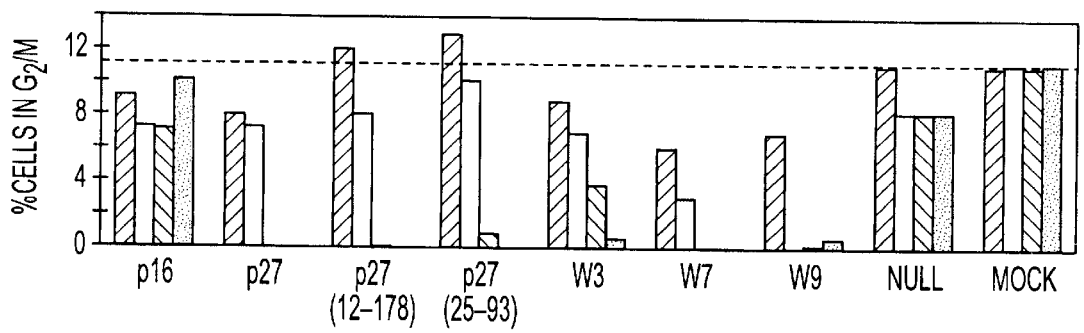
FIG. 10B is a schematic representation of a series of bar graphs comparing the cell cycle distributions (i.e., $G_2$/M phase, S phase, or $G_1$ phase) of the CASMCs transduced with 1, 10, 50, or 100 MOI of with recombinant adenovirus encoding the indicated CDKi or Null (i.e., AV-CMV), or no adenovirus (Mock). The proportion of cells in the different cell cycle stages was determined for mock transduced and adenovirus transduced (1–100 MOI) CASMC. The upper panel shows the percentage of cells in $G_2$/M phase; the middle panel shows the percentage of cells in S phase; the lower panel shows the percentage of cells in $G_1$ phase.
Figures 2, 10B:
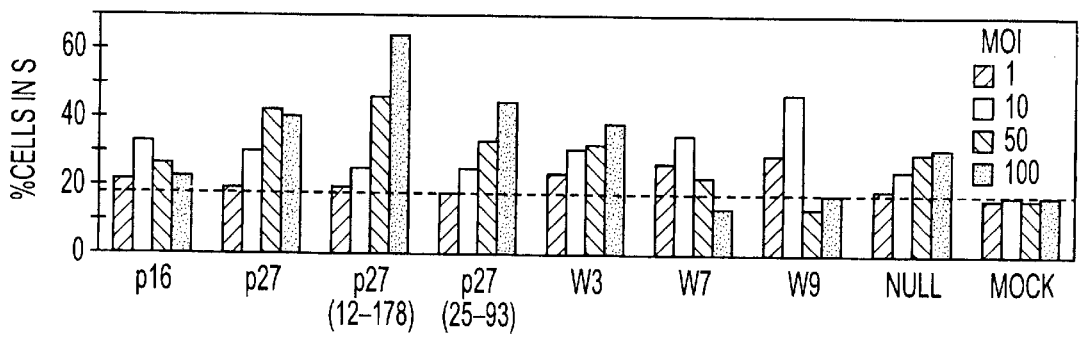
Figures 3, 10B:
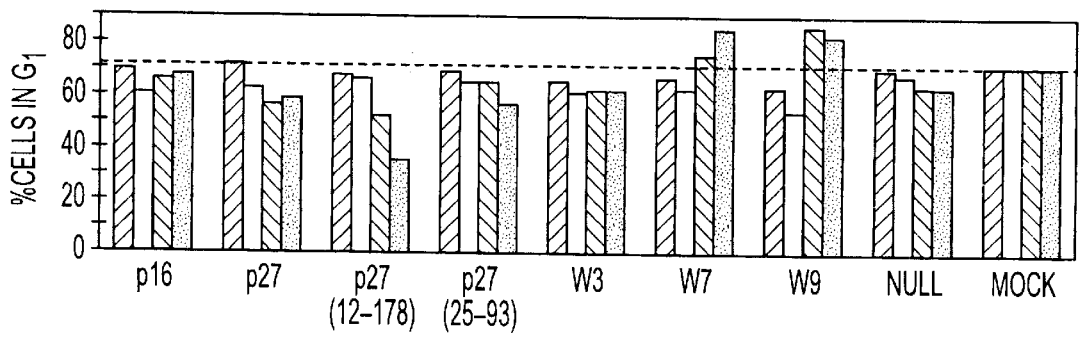

As can be seen in FIG. 12, aortic rings transduced with $5 \times 10^{10}$ viral particles of either AV-p16 or AV-W9 showed no sprouting of microvessels as compared to the null-infected ring (FIG. 12, left 3 panels). Transduction with $2.5 \times 10^{10}$ viral particles of AV-W9 similarly inhibited ring sprouting of microvessels; however, transduction with $2.5 \times 10^{10}$ viral particles of AV-p16 did not inhibit ring sprouting (FIG. 12, middle 3 panels). These results demonstrate that both AV-p16 and AV-W9 have angiogenesis-inhibiting activities; however, AV-W9 is more potent.

EXAMPLE X

Adenovirus Delivered CDKi Have Angiogenesis-Inhibiting Activity as Measured by the Matrigel Tube Assay AV-W9 was next tested for angiogenesis-inhibiting activity using the matrigel tube assay. The matrigel tube assay is a standard method for measuring angiogenesis activity. (see Nicosia and Ottinetti (1990) In Vitro Cell Devel. Bio. 26:119). In this assay, cells are plated onto matrigel. Given the multiple factors and matrixes provided by matrigel, if the cells are angiogenesis capable, they will form tube-like structures. However, if the cells are inhibited to undergo angiogenesis, no tube-like structures will result.

One day before the experiment, 1–2 boxes of P1000 tips, 24 well plates, and tubes were placed in refrigerator at 4° C. MATRIGEL, which is stored at −20° C., was thawed at 4° C. overnight on ice and kept on ice before use. Human umbilical vein endothelial cells (HUVEC, commercially available Clonetics, Walkersville, Md.) were transduced with AV-W9 twenty-four hours before the experiment. The HUVEC used were at passage 6 or less. The ratio of virus particle to cells was $5 \times 10^4$ p/c or $1 \times 10^4$ p/c. For positive control, HUVEC iu) cells were incubated in Matrigel supplemented with 50 ng/ml Fibroblast Growth Factor-basic (bFGF; Cat#F0291; Sigma Chemical Co., St. Louis, Mo.).

On the day of the experiment, the MATRIGEL basement membrane matrix was mixed to homogeneity by swirling the bottle. Keeping the culture plates on ice, 300 µl of MATRIGEL was added to gel in each well of a 24 well plate. The MATRIGEL-containing plate was then incubated at 37° C. for 30 minutes, at which point they were ready for use.

Meanwhile, the transduced and control HUVEC cells were prepared. The cells were first rinsed with HBSS (HEPES buffered saline solution). Next, a trypsin/EDTA solution (10 µg/ml trypsin plus 0.25 mg/ml EDTA) was added into the flask of cells, and incubated at room temperature for approximately 5 min with gentle rocking. The cells were checked under microscope to determine when they were dislodged from the flask. Once all the cells were dislodged, the reaction was stopped with the addition of TNS (Trypsin Neutralizing Solution;

Clonetics, Walkersville, Md.). Note that all of the reagents and medium used were brought to room temperature prior to use.

The dislodged cells were next spun down at 1000 rpm on a benchtop centrifuge. The pelleted cells were resuspended in 5 to 10 ml medium and counted. The HUVEC were resuspended to a final concentration of $4 \times 10^4$ cells/ml in endothelial cell growth media (Culture Medium—EGM-2 (or EGM) Bullet Kit; Cat# CC-3162, Clonetics, Walkersville, Md.). One ml of cell suspension was aliquoted into each MATRIGEL-coated plate.

The plated cells were incubated at 37° C. overnight, and the plates then checked under a microscope. Next, the cells were stained with Dip Quick Fix and Solution II (Cat# J322, Jorgenson Laboratories, Inc., Loveland, Colo.). The stained cells, and any resulting tubes, were quantitated with NIH image or Optomax.

Figures 13A, 13B, 13C:
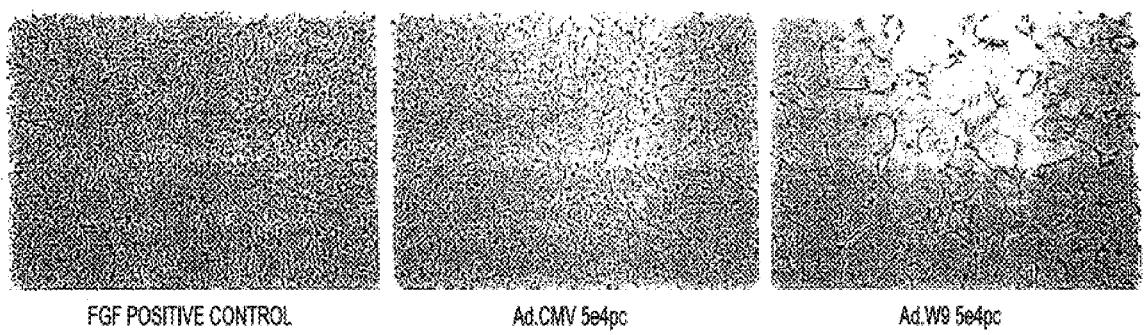
FIG. 13A is a photographic representation showing the angiogenesis-inhibiting effect of AV-W9 in a matrigel tube assay, where HUVEC have been treated with basic fibroblast growth factor.
FIG. 13B is a photographic representation showing the angiogenesis-inhibiting effect of AV-W9 in a matrigel tube assay, where HUVEC have been transduced with $5 \times 10^4$ AV-CMV (which contains only the CMV promoter) viral particles per cell.
FIG. 13C is a photographic representation showing the angiogenesis-inhibiting effect of AV-W9 in a matrigel tube assay, where HUVEC have been transduced with $5 \times 10^4$ AV-W9 viral particles per cell.

As shown in FIG. 13, HUVEC transduced with AV-W9 failed to form tubes when cultured on matrigel (right panel). In contrast, HUVEC transduced with the control adenovirus, AV-CMV, were stimulated to form tubes (FIG. 13, middle panel). The bFGF-treated HUVEC, of course, formed an abundance of tubes when cultured on matrigel (FIG. 13, right panel). These results demonstrate that transduction with AV-W9 inhibited angiogenesis.

EXAMPLE XI

An Adenovirus Lacking Both the E1 and the E4 Regions And Expressing the W9 Fusion Protein has Angiogenesis-Inhibiting Activity A replication-defective recombinant adenovirus lacking both the E1 and the E4 regions has recently been described (see Wang et al., U.S. patent application Ser. No. 08/552,829, filed Nov. 3, 1995, the entirety of which is hereby incorporated by reference). This adenovirus results in reduced pathologic effects and prolonged expression of the transgene. Moreover, the ΔE1/ΔE4 adenovirus can accommodate larger transgene(s) than the singly deleted (i.e., ΔE1) adenovirus.

A ΔE1/ΔE4 adenovirus encoding W9 is generated using the methods and cells generally described in Wang et al., U.S. patent application Ser. No. 08/552,829, filed Nov. 3, 1995. Because deletion of the adenovirus E4 region is a lethal mutation to adenoviruses, these recombinant adenoviruses are packaged in a 293-E4 cell, which is stably transfected with nucleic acid comprising the entire adenovirus E4 region under the control of the inducible promoter. The only adenovirus E4 region protein expressed by this E4 region-deleted adenoviruses is the E4orf4 protein, and that in very low amounts.

When endothelial cells are transduced with this W9-encoding adenovirus lacking both the E1 region and the E4 region, the cells show an inhibited ability to undergo angiogenesis in both the matrigel tube assay and the aortic ring sprouting assay. Accordingly, the E4 region of adenovirus, or a protein (or active fragment) encoded thereby, is not involved in the angiogenesis-inhibiting activity of AV-W9 (the singly deleted ΔE1 adenovirus encoding W9).

EXAMPLE XII

Angiogenesis-Inhibiting Activity of Recombinant Lentiviruses Expressing CDKi Fusion Proteins A second virus-based delivery vehicle for the CDKi fusion proteins is generated. Here, a lentivirus vector previously described (see Dull et al. (1998) *J. Virol.* 72:8463–8471) is used to generate recombinant lentiviruses encoding W9, W7, p16, and p27. Transgenes similar to those described in Example III (i.e., a transgene consisting of CMV enhancer/promoter-CDKi insert-SV40 polyA) are inserted into the lentivirus transfer vector, pRRL.sin-18, between the splice acceptor cite and the 3' LTR (Dull et al., supra). These lentivirus-expressed CDKi are generated such that they do not have the 6 His, HA tag.

The recombinant lentiviruses are packaged essentially as described in Dull et al., supra. The recombinant lentiviruses are used to transduce endothelial cells according to the methods generally described above for the recombinant adenoviruses. For example, for CAEC cells, the cells are seeded at $1.3 \times 10^4$ or $3 \times 10^4$ cells/well in a 24 well plate in EBM media supplemented with 5% FBS. The following day, the media is aspirated, and new media (1 ml/well) is added with or without polybrene at a final concentration of 8 pg/ml. The cells are then transduced with an equivalent number of viral particles of lentiviruses encoding W7, W9, p16, or p27. Twenty-four hours following transduction, the media of the cells is changed, and angiogenesis-inhibiting activity, as measured by the matrigel tube assay and/or the aortic ring sprouting assay, is tested 48 hours later (i.e., three days post-transduction).

In a slight modification, a second form of recombinant lentivirus is generated encoding CDKi fusion proteins of the invention. FIG. 14A illustrates a representative recombinant lentivirus vector containing a W9 expression cassette (i.e., W9-encoding nucleic acid sequence operably linked to regulatory sequences) flanked by HIV LTRS. Downstream of the 5' LTR, the vector contains the HIV leader sequence, the major 5' splice donor site (SD), the packaging sequence (Ψ), the first 43 bps of the HIV gag gene, the HIV Rev Response Element (RRE), and the splice acceptor sites (SA) of the second exon of HIV tat and HIV rev. This vector may be packaged according to standard techniques to generate a recombinant lentivirus that encodes W9 (see Dull et al., supra).

Another recombinant lentiviral vector is shown on FIG. 14B. This self-inactivating lentiviral vector contains a W9 expression cassette flanked by a 5' HIV LTR having a substituted U3 region and a 3' HIV LTR, or a 5' HIV LTR and a deleted 3' HIV LTR. This vector further contains downstream from the 5' LTR and HIV leader sequence, the major 5' SD, Ψ, the first 43 bps of the gag gene, the RRE, and the SA of the second exon at tat and rev (see Naldini et al. (1996) *Science* 272:263–267).

These studies show that W9 delivered by lentivirus in the absence of any adenovirus-encoded proteins induces angiogenesis-inhibition in endothelial cells.

EXAMPLE XIII

Purified W9 Protein Has Angiogenesis-Inhibiting Activity

The W9 fusion CDKi protein and other fusion CDKi proteins of the invention (including W7 and W3), as well as parental proteins p16, p27, $p27_{12-178}$, and $p27_{25-93}$ are purified from 293 cells transduced with the respective AV-CDKi. With the exception of p16, the fusion CDKi and parental protein are purified over an affinity column using anti-p27 antibody. One such antibody is the p27/Kip1 antibody commercially available from Transduction Laboratories, Lexington, Ky. The p16 protein is purified from 293 cells transduced with AV-p16 using an anti-p16 antibody. One such antibody is the p16-C20, which is commercially available from Santa Cruz Biotech., Santa Cruz, Calif.

The purified proteins are then used in the aortic ring assay to detect an angiogenesis-inhibiting activity. In this method, rat aortic rings are prepared as described above and plated on matrigel basement membrane coated wells of a 24 well plate. The rings are then covered with endothelial cell media to which has been added nothing (positive control), and various amounts of the following purified proteins: p16, p27, $p27_{12-178}$, and $p27_{25-93}$, W9, W7, and W3. After incubation for seven days, the rings are photographed. Although several of the purified proteins show an angiogenesis-inhibiting effect, purified W9 has the strongest angiogenesis-inhibiting effect at the lowest concentration.

Equivalents

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the invention is as set forth in the appended claims rather than being limited to the examples contained in the foregoing description.

What is claimed is:

1. A method for inhibiting angiogenesis, comprising:
   (a) transducing endothelial cells with an effective amount of a replication-deficient viral vector that comprises a transgene encoding a cyclin dependent kinase inhibitor (CDKi) and
   (b) expressing said transgene in the endothelial cells resulting in generation of transduced endothelial cells, wherein said transduced endothelial cells exhibit a decrease in proliferation or migration and said cyclin dependent kinase inhibitor is a fusion protein consisting of amino acids 25–93 of p27 fused to p16 (SEQ ID NO:14) or a fusion protein consisting of amino acids 12–178 of p27 fused to p16 (SEQ ID NO:20).

2. The method according to claim 1 wherein the fusion protein consists of amino acids 25–93 of p27 fused to p16.

3. The method according to claim 1 wherein the fusion protein consists of amino acids 12–178 of p27 fused to p16.

4. The method according to claim 1 wherein the endothelial cell proliferation or migration is caused by a condition selected from the group consisting of neoplasia, rheumatoid arthritis, vascular retinopathy, endometriosis and psoriasis.

5. The method according to claim 4 wherein the condition is neoplasia.

6. The method according to claim 1 wherein the replication-deficient viral vector is an adenoviral vector that lacks a functional E1 region.

7. The method according to claim 6 wherein the fusion protein consists of amino acids 25–93 of p27 fused to p16.

8. The method according to claim 6 wherein the fusion protein consists of amino acids 12–178 of p27 fused to p16.

9. The method according to claim 6 wherein the endothelial cell proliferation migration is caused by neoplasia.

10. The method according to claim 6 wherein the replication-deficient adenoviral vector further lacks a functional E4 region.

11. The method according to claim 10 wherein the endothelial cell proliferation or migration is caused by neoplasia.

12. The method according to claim 10 wherein the fusion protein consists of amino acids 25–93 of p27 fused to p16.

13. The method according to claim 10 wherein the fusion protein consists of amino acids 12–178 of p27 fused to p16.

14. The method according to claim 6 wherein the replication-deficient adenovirus further lacks a functional E3 region.

15. The method according to claim 14 wherein the endothelial cell proliferation or migration is caused by neoplasia.

16. The method according to claim 14 wherein the fusion protein consists of amino acids 25–93 of p27 fused to p16.

17. The method according to claim 14 wherein the fusion protein consists of amino acids 12–178 of p27 fused to p16.

18. The method according to claim 1 wherein the replication-deficient viral vector is a lentivirus.

19. The method according to claim 18 wherein the fusion protein consists of amino acids 25–93 of p27 fused to p16.

20. The method according to claim 18 wherein the fusion protein consists of amino acids 12–178 of p27 fused to p16.

21. The method according to claim 18 wherein the endothelial cell proliferation or migration is caused by neoplasia.

* * * * *

SEQUENCE LISTING

<160> NUMBER OF SEQ ID NOS: 32

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 1
gcggccggtc atatgcacca ccatcaccat cactcaaacg tgcgagtgtc t           51

<210> SEQ ID NO 2
<211> LENGTH: 96
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 2
gccgccggcg tcgactcggc cgaattcgga tccaccccg ccggaaccgc caccccgct    60 gccccgcca cccgtttgac gtcttctgag gccagg                             96

<210> SEQ ID NO 3
<211> LENGTH: 1420
<212> TYPE: DNA
<213> ORGANISM: Homo sapiens

<400> SEQUENCE: 3
catatgcacc accatcacca tcactcaaac gtgcgagtgt ctaacgggag ccctagcctg   60
gagcggatgg acgccaggca ggcggagcac cccaagccct cggcctgcag gaacctcttc   120
ggcccggtgg accacgaaga gttaacccgg gacttggaga agcactgcag agacatggaa   180
gaggcgagcc agcgcaagtg gaatttcgat tttcagaatc acaaacccct agagggcaag   240
tacgagtggc aagaggtgga aagggcagc ttgcccgagt tctactacag accccgcgg    300 cccccaaag tgcctgcaa ggtgccggcg caggagagcc aggatgtcag cgggagccgc    360
ccggcggcgc cttttaattgg ggctccggct aactctgagg acacgcattt ggtggaccca   420
aagactgatc cgtcggacag ccagacgggg ttagcggagc aatgcgcagg aataaggaag   480
cgacctgcaa ccgacgattc ttctactcaa acaaaagag ccaacagaac agaagaaaat   540
gtttcagacg gttccccaaa tgccggttct gtggagcaga cgcccaagaa gcctggcctc   600
agaagacgtc aaacggggtgg cgggggcagc gggggtggcg gttccggcgg gggtggatcc   660
gaattctgcg gccgcgcgtg cgctcggcgg ctgcggagag gggagagcat gcagcgggcg   720
gcggggagca gcatggagcc ttcggctgac tggctggcca cggccgcggc ccggggtcgg   780
gtagaggagg tgcgggcgct gctggaggcg gtggcgctgc ccaacgcacc gaatagttac   840
ggtcggaggc cgatccaggt catgatgatg ggcagcgccc gagtggcgga gctgctgctg   900
ctccacggcg cggagcccaa ctgcgccgac cccgccactc tcacccgacc cgtgcacgac   960
gctgcccggg agggcttcct ggacacgctg gtggtgctgc accggccgg ggcgcggctg   1020 gacgtgcgcg atgcctgggg ccgtctgccc gtgacctgg ctgaggagct gggccatcgc   1080
gatgtcgcac ggtacctgcg cgcggctgcg ggggcacca gaggcagtaa ccatgcccgc   1140
atagatgccg cggaaggtcc ctcagacatc cccgattgaa agaaccagag aggctctgag   1200

-continued

```
aaacctcggg aaacttagat catcagtcac cgaaggtcct acagggccac aactgccccc   1260
gccacaaccc accccgcttt cgtagttttc atttagaaaa tagagctttt aaaaatgtcc   1320
tgccttttaa cgtagatata agccttcccc cactaccgta aatgtccatt tatatcattt   1380
tttatatatt cttataaaaa tgtaaaaaag aaaactcgag                         1420
```

<210> SEQ ID NO 4
<211> LENGTH: 391
<212> TYPE: PRT
<213> ORGANISM: Homo sapiens

<400> SEQUENCE: 4

```
Met His His His His His Ser Asn Val Arg Val Ser Asn Gly Ser
 1               5                  10                  15

Pro Ser Leu Glu Arg Met Asp Ala Arg Gln Ala Glu His Pro Lys Pro
                20                  25                  30

Ser Ala Cys Arg Asn Leu Phe Gly Pro Val Asp His Glu Glu Leu Thr
            35                  40                  45

Arg Asp Leu Glu Lys His Cys Arg Asp Met Glu Glu Ala Ser Gln Arg
        50                  55                  60

Lys Trp Asn Phe Asp Phe Gln Asn His Lys Pro Leu Glu Gly Lys Tyr
    65                  70                  75                  80

Glu Trp Gln Glu Val Glu Lys Gly Ser Leu Pro Glu Phe Tyr Tyr Arg
                85                  90                  95

Pro Pro Arg Pro Pro Lys Gly Ala Cys Lys Val Pro Ala Gln Glu Ser
                100                 105                 110

Gln Asp Val Ser Gly Ser Arg Pro Ala Ala Pro Leu Ile Gly Ala Pro
            115                 120                 125

Ala Asn Ser Glu Asp Thr His Leu Val Asp Pro Lys Thr Asp Pro Ser
        130                 135                 140

Asp Ser Gln Thr Gly Leu Ala Glu Gln Cys Ala Gly Ile Arg Lys Arg
    145                 150                 155                 160

Pro Ala Thr Asp Asp Ser Ser Thr Gln Asn Lys Arg Ala Asn Arg Thr
                165                 170                 175

Glu Glu Asn Val Ser Asp Gly Ser Pro Asn Ala Gly Ser Val Glu Gln
            180                 185                 190

Thr Pro Lys Lys Pro Gly Leu Arg Arg Arg Gln Thr Gly Gly Gly Gly
        195                 200                 205

Ser Gly Gly Gly Gly Ser Gly Gly Gly Ser Glu Phe Cys Gly Arg
    210                 215                 220

Ala Cys Ala Arg Arg Leu Arg Arg Gly Glu Ser Met Gln Arg Ala Ala
225                 230                 235                 240

Gly Ser Ser Met Glu Pro Ser Ala Asp Trp Leu Ala Thr Ala Ala
                245                 250                 255

Arg Gly Arg Val Glu Glu Val Arg Ala Leu Leu Glu Ala Val Ala Leu
            260                 265                 270

Pro Asn Ala Pro Asn Ser Tyr Gly Arg Arg Pro Ile Gln Val Met Met
        275                 280                 285

Met Gly Ser Ala Arg Val Ala Glu Leu Leu Leu His Gly Ala Glu
    290                 295                 300

Pro Asn Cys Ala Asp Pro Ala Thr Leu Thr Arg Pro Val His Asp Ala
305                 310                 315                 320

Ala Arg Glu Gly Phe Leu Asp Thr Leu Val Val Leu His Arg Ala Gly
                325                 330                 335
```

```
Ala Arg Leu Asp Val Arg Asp Ala Trp Gly Arg Leu Pro Val Asp Leu
        340                 345                 350

Ala Glu Glu Leu Gly His Arg Asp Val Ala Arg Tyr Leu Arg Ala Ala
        355                 360                 365

Ala Gly Gly Thr Arg Gly Ser Asn His Ala Arg Ile Asp Ala Ala Glu
    370                 375                 380

Gly Pro Ser Asp Ile Pro Asp
385                 390

<210> SEQ ID NO 5
<211> LENGTH: 1121
<212> TYPE: DNA
<213> ORGANISM: Homo sapiens

<400> SEQUENCE: 5
gaattcgccg ccaccatggg atacccttat gatgtgccag attatgcctc aaacgtgcga     60
gtgtctaacg gccgccctag cctggagcgg atggacgcca ggcaggcgga gcaccccaag    120
ccctcggcct gcaggaacct cttcggcccg gtggaccacg aagagttaac ccggacttg    180 gagaagcact gcagagacat ggaagaggcg agccagcgca agtggaattt cgattttcag    240
aatcacaaac ccctagaggg caagtacgag tggcaagagg tggagaaggg cagcttgccc    300
gagttctact acagaccccc gcggcccccc aaaggtgcct gcaaggtgcc ggcgcaggag    360
agccaggatg tcagcgggag ccgcccggcg gcgcctttaa ttggggctcc ggctaactct    420
gaggacacgc atttggtgga cccaaagact gatccgtcgg agagccagac ggggttagcg    480
gagcaatgcg caggaataag gaagcgacct gcaaccgacg attcttctac tcaaaacaaa    540
agagccaaca gaacagaaga aaatgtttca gacggttccc caaatgccgg ttctgtggag    600
cagacgccca gaagcctggc ctcagaaga cgtcaaacgg tcgaggatcc ggcggcgggg    660
agcagcatgg agccttcggc tgactggctg ccacggccg cggcccgggg tcgggtagag    720
gaggtgcggg cgctgctgga ggcggggcg ctgcccaacg caccgaatag ttacggtcgg    780
aggccgatcc aggtcatgat gatgggcagc gcccgagtgg cggagctgct gctgctccac    840
ggcgcggagc ccaactgcgc cgaccccgcc actctcaccc gacccgtgca cgacgctgcc    900
cgggagggct tcctggacac gctggtggtg ctgcaccggg ccggggcgcg gctggacgtg    960
cgcgatgcct ggggccgtct gcccgtggac ctggctgagg agctgggcca tcgcgatgtc   1020
gcacggtacc tgcgcgcggc tgcggggggc accagaggca gtaaccatgc ccgcatagat   1080
gccgcggaag gtccctcaga catccccgat tgagcggccg c                       1121

<210> SEQ ID NO 6
<211> LENGTH: 365
<212> TYPE: PRT
<213> ORGANISM: Homo sapiens

<400> SEQUENCE: 6

Met Gly Tyr Pro Tyr Asp Val Pro Asp Tyr Ala Ser Asn Val Pro Val
  1               5                  10                  15

Ser Asn Gly Arg Pro Ser Leu Glu Arg Met Asp Ala Arg Gln Ala Glu
             20                  25                  30

His Pro Lys Pro Ser Ala Cys Arg Asn Leu Phe Gly Pro Val Asp His
         35                  40                  45

Glu Glu Leu Thr Arg Asp Leu Glu Lys His Cys Arg Asp Met Glu Glu
     50                  55                  60
```

```
Ala Ser Gln Arg Lys Trp Asn Phe Asp Phe Gln Asn His Lys Pro Leu
 65                  70                  75                  80

Glu Gly Lys Tyr Glu Trp Gln Glu Val Glu Lys Gly Ser Leu Pro Glu
                 85                  90                  95

Phe Tyr Tyr Arg Pro Arg Pro Lys Gly Ala Cys Lys Val Pro
            100                 105                 110

Ala Gln Glu Ser Gln Asp Val Ser Gly Ser Arg Pro Ala Ala Pro Leu
            115                 120                 125

Ile Gly Ala Pro Ala Asn Ser Glu Asp Thr His Leu Val Asp Pro Lys
130                 135                 140

Thr Asp Pro Ser Asp Ser Gln Thr Gly Leu Ala Glu Gln Cys Ala Gly
145                 150                 155                 160

Ile Arg Lys Arg Pro Ala Thr Asp Asp Ser Ser Thr Gln Asn Lys Arg
                165                 170                 175

Ala Asn Arg Thr Glu Glu Asn Val Ser Asp Gly Ser Pro Asn Ala Gly
            180                 185                 190

Ser Val Glu Gln Thr Pro Lys Lys Pro Gly Leu Arg Arg Arg Gln Thr
            195                 200                 205

Val Glu Asp Pro Ala Ala Gly Ser Ser Met Glu Pro Ser Ala Asp Trp
210                 215                 220

Leu Ala Thr Ala Ala Ala Arg Gly Arg Val Glu Val Arg Ala Leu
225                 230                 235                 240

Leu Glu Ala Gly Ala Leu Pro Asn Ala Pro Asn Ser Tyr Gly Arg Arg
                245                 250                 255

Pro Ile Gln Val Met Met Met Gly Ser Ala Arg Val Ala Glu Leu Leu
            260                 265                 270

Leu Leu His Gly Ala Glu Pro Asn Cys Ala Asp Pro Ala Thr Leu Thr
            275                 280                 285

Arg Pro Val His Asp Ala Ala Arg Glu Gly Phe Leu Asp Thr Leu Val
            290                 295                 300

Val Leu His Arg Ala Gly Ala Arg Leu Asp Val Arg Asp Ala Trp Gly
305                 310                 315                 320

Arg Leu Pro Val Asp Leu Ala Glu Glu Leu Gly His Arg Asp Val Ala
                325                 330                 335

Arg Tyr Leu Arg Ala Ala Ala Gly Gly Thr Arg Gly Ser Asn His Ala
            340                 345                 350

Arg Ile Asp Ala Ala Glu Gly Pro Ser Asp Ile Pro Asp
            355                 360                 365

<210> SEQ ID NO 7
<211> LENGTH: 1143
<212> TYPE: DNA
<213> ORGANISM: Homo sapiens

<400> SEQUENCE: 7
atgggatacc cttatgatgt gccagattat gccgatccgg cggcggggag cagcatggag      60
ccttcggctg actggctggc cacggccgcg gcccggggtc gggtagagga ggtgcgggcg     120
ctgctggagg cggggggcgct gcccaacgca ccgaatagtt acggtcggag gccgatccag     180
gtcatgatga tggcagcgc ccgagtggcg gagctgctgc tgctccacgg cgcggagccc     240
aactgcgccg accccgccac tctcacccga cccgtgcacg acgctgcccg ggagggcttc     300
ctggacacgc tggtggtgct gcaccgggcc ggggcgcggc tggacgtgcg cgatgcctgg     360
ggccgtctgc ccgtggacct ggctgaggag ctgggccatc gcgatgtcgc acggtacctg     420
```

-continued

```
cgcgcggctg cgggggggcac cagaggcagt aaccatgccc gcatagatgc cgcggaaggt    480
ccctcagaca tccccgatgg tggcgggggc agcgggggtg gcggttccgg cggggggtgga   540 tccgtcgagt caaacgtgcg agtgtctaac gggcgcccta gcctggagcg gatgggacgcc   600 aggcaggcgg agcaccccaa gccctcggcc tgcaggaacc tcttcggccc ggtggaccac    660
gaagagttaa cccgggactt ggagaagcac tgcagagaca tggaagaggc gagccagcgc    720
aagtggaatt tcgattttca gaatcacaaa ccctagagg gcaagtacga gtggcaagag     780
gtggagaagg gcagcttgcc cgagttctac tacagacccc cgcggccccc caaaggtgcc    840
tgcaaggtgc cggcgcagga gagccaggat gtcagcggga gccgcccggc ggcgcctta     900 attgggctc cggctaactc tgaggacacg catttggtgg acccaaagac tgatccgtcg     960
gacagccaga cggggttagc ggagcaatgc gcaggaataa ggaagcgacc tgcaaccgac    1020
gattcttcta ctcaaaacaa aagagccaac agaacagaag aaaatgtttc agacggttcc    1080
ccaaatgccg gttctgtgga gcagacgccc aagaagcctg gcctcagaag acgtcaaacg    1140
taa                                                                  1143
```

<210> SEQ ID NO 8
<211> LENGTH: 380
<212> TYPE: PRT
<213> ORGANISM: Homo sapiens

<400> SEQUENCE: 8

```
Met Gly Tyr Pro Tyr Asp Val Pro Asp Tyr Ala Asp Pro Ala Ala Gly
  1               5                  10                  15

Ser Ser Met Glu Pro Ser Ala Asp Trp Leu Ala Thr Ala Ala Arg
             20                  25                  30

Gly Arg Val Glu Glu Val Arg Ala Leu Leu Glu Ala Gly Ala Leu Pro
         35                  40                  45

Asn Ala Pro Asn Ser Tyr Gly Arg Arg Pro Ile Gln Val Met Met Met
     50                  55                  60

Gly Ser Ala Arg Val Ala Glu Leu Leu Leu Leu His Gly Ala Glu Pro
 65                  70                  75                  80

Asn Cys Ala Asp Pro Ala Thr Leu Thr Arg Pro Val His Asp Ala Ala
                 85                  90                  95

Arg Glu Gly Phe Leu Asp Thr Leu Val Val Leu His Arg Ala Gly Ala
            100                 105                 110

Arg Leu Asp Val Arg Asp Ala Trp Gly Arg Leu Pro Val Asp Leu Ala
        115                 120                 125

Glu Glu Leu Gly His Arg Asp Val Ala Arg Tyr Leu Arg Ala Ala Ala
    130                 135                 140

Gly Gly Thr Arg Gly Ser Asn His Ala Arg Ile Asp Ala Ala Glu Gly
145                 150                 155                 160

Pro Ser Asp Ile Pro Asp Gly Gly Gly Ser Gly Gly Gly Gly Ser
                165                 170                 175

Gly Gly Gly Gly Ser Val Glu Ser Asn Val Arg Val Ser Asn Gly Arg
            180                 185                 190

Pro Ser Leu Glu Arg Met Asp Ala Arg Gln Ala Glu His Pro Lys Pro
        195                 200                 205

Ser Ala Cys Arg Asn Leu Phe Gly Pro Val Asp His Glu Glu Leu Thr
    210                 215                 220

Arg Asp Leu Glu Lys His Cys Arg Asp Met Glu Glu Ala Ser Gln Arg
225                 230                 235                 240
```

```
Lys Trp Asn Phe Asp Phe Gln Asn His Lys Pro Leu Glu Gly Lys Tyr
                245                 250                 255
Glu Trp Gln Glu Val Glu Lys Gly Ser Leu Pro Glu Phe Tyr Tyr Arg
            260                 265                 270
Pro Pro Arg Pro Pro Lys Gly Ala Cys Lys Val Pro Ala Gln Glu Ser
            275                 280                 285
Gln Asp Val Ser Gly Ser Arg Pro Ala Ala Pro Leu Ile Gly Ala Pro
        290                 295                 300
Ala Asn Ser Glu Asp Thr His Leu Val Asp Pro Lys Thr Asp Pro Ser
305                 310                 315                 320
Asp Ser Gln Thr Gly Leu Ala Glu Gln Cys Ala Gly Ile Arg Lys Arg
                325                 330                 335
Pro Ala Thr Asp Asp Ser Ser Thr Gln Asn Lys Arg Ala Asn Arg Thr
            340                 345                 350
Glu Glu Asn Val Ser Asp Gly Ser Pro Asn Ala Gly Ser Val Glu Gln
            355                 360                 365
Thr Pro Lys Lys Pro Gly Leu Arg Arg Arg Gln Thr
    370                 375                 380

<210> SEQ ID NO 9
<211> LENGTH: 1098
<212> TYPE: DNA
<213> ORGANISM: Homo sapiens

<400> SEQUENCE: 9
atgggatacc cttatgatgt gccagattat gccgatccgg cggcggggag cagcatggag      60
ccttcggctg actggctggc cacggccgcg gcccggggtc gggtagagga ggtgcgggcg     120
ctgctggagg cggggggcgct gcccaacgca ccgaatagtt acggtcggag gccgatccag     180
gtcatgatga tgggcagcgc ccgagtggcg gagctgctgc tgctccacgg cgcggagccc     240
aactgcgccg accccgccac tctcacccga cccgtgcacg acgctgcccg ggagggcttc     300
ctggacacgc tggtggtgct gcaccgggcc ggggcgcggc tggacgtgcg cgatgcctgg     360
ggccgtctgc ccgtggacct ggctgaggag ctgggccatc gcgatgtcgc acggtacctg     420
cgcgcggctg cgggggggcac cagaggcagt aaccatgccc gcatagatgc gcggaaggt      480 ccctcagaca tccccgatgt cgagtcaaac gtgcgagtgt ctaacgggcg ccctagcctg     540
gagcggatgg acgccaggca ggcggagcac cccaagccct cggcctgcag gaacctcttc     600
ggcccggtgg accacgaaga gttaacccgg gacttggaga agcactgcag agacatggaa     660
gaggcgagcc agcgcaagtg gaatttcgat tttcagaatc acaaacccct agagggcaag     720
tacgagtggc aagaggtgga aagggcagc ttgcccgagt tctactacag accccgcgg      780 ccccccaaag gtgcctgcaa ggtgccggcg caggagagcc aggatgtcag cgggagccgc     840
ccggcggcgc ctttaattgg ggctccggct aactctgagg acacgcattt ggtggaccca     900
aagactgatc cgtcggacag ccagacgggg ttagcggagc aatgcgcagg aataaggaag     960
cgacctgcaa ccgacgattc ttctactcaa acaaaagag ccaacagaac agaagaaaat    1020
gtttcagacg gttccccaaa tgccggttct gtggagcaga cgcccaagaa gcctggcctc    1080
agaagacgtc aaacgtaa                                                 1098

<210> SEQ ID NO 10
<211> LENGTH: 365
<212> TYPE: PRT
<213> ORGANISM: Homo sapiens
```

```
<400> SEQUENCE: 10

Met Gly Tyr Pro Tyr Asp Val Pro Asp Tyr Ala Asp Pro Ala Ala Gly
  1               5                  10                  15

Ser Ser Met Glu Pro Ser Ala Asp Trp Leu Ala Thr Ala Ala Ala Arg
             20                  25                  30

Gly Arg Val Glu Glu Val Arg Ala Leu Leu Glu Ala Gly Ala Leu Pro
             35                  40                  45

Asn Ala Pro Asn Ser Tyr Gly Arg Arg Pro Ile Gln Val Met Met Met
 50                  55                  60

Gly Ser Ala Arg Val Ala Glu Leu Leu Leu Leu His Gly Ala Glu Pro
 65                  70                  75                  80

Asn Cys Ala Asp Pro Ala Thr Leu Thr Arg Pro Val His Asp Ala Ala
                 85                  90                  95

Arg Glu Gly Phe Leu Asp Thr Leu Val Val Leu His Arg Ala Gly Ala
                100                 105                 110

Arg Leu Asp Val Arg Asp Ala Trp Gly Arg Leu Pro Val Asp Leu Ala
            115                 120                 125

Glu Glu Leu Gly His Arg Asp Val Ala Arg Tyr Leu Arg Ala Ala Ala
130                 135                 140

Gly Gly Thr Arg Gly Ser Asn His Ala Arg Ile Asp Ala Ala Glu Gly
145                 150                 155                 160

Pro Ser Asp Ile Pro Asp Val Glu Ser Asn Val Arg Val Ser Asn Gly
                165                 170                 175

Arg Pro Ser Leu Glu Arg Met Asp Ala Arg Gln Ala Glu His Pro Lys
            180                 185                 190

Pro Ser Ala Cys Arg Asn Leu Phe Gly Pro Val Asp His Glu Glu Leu
        195                 200                 205

Thr Arg Asp Leu Glu Lys His Cys Arg Asp Met Glu Glu Ala Ser Gln
210                 215                 220

Arg Lys Trp Asn Phe Asp Phe Gln Asn His Lys Pro Leu Glu Gly Lys
225                 230                 235                 240

Tyr Glu Trp Gln Glu Val Glu Lys Gly Ser Leu Pro Glu Phe Tyr Tyr
                245                 250                 255

Arg Pro Pro Arg Pro Pro Lys Gly Ala Cys Lys Val Pro Ala Gln Glu
            260                 265                 270

Ser Gln Asp Val Ser Gly Ser Arg Pro Ala Ala Pro Leu Ile Gly Ala
        275                 280                 285

Pro Ala Asn Ser Glu Asp Thr His Leu Val Asp Pro Lys Thr Asp Pro
290                 295                 300

Ser Asp Ser Gln Thr Gly Leu Ala Glu Gln Cys Ala Gly Ile Arg Lys
305                 310                 315                 320

Arg Pro Ala Thr Asp Asp Ser Ser Thr Gln Asn Lys Arg Ala Asn Arg
                325                 330                 335

Thr Glu Glu Asn Val Ser Asp Gly Ser Pro Asn Ala Gly Ser Val Glu
            340                 345                 350

Gln Thr Pro Lys Lys Pro Gly Leu Arg Arg Arg Gln Thr
        355                 360                 365

<210> SEQ ID NO 11
<211> LENGTH: 557
<212> TYPE: DNA
<213> ORGANISM: Homo sapiens

<400> SEQUENCE: 11
```

-continued

```
gaattcgccg ccaccatggg atacccttat gatgtgccag attatgccag cctggagcgg     60
atggacgcca ggcaggcgga gcaccccaag ccctcggcct gcaggaacct cttcggcccg    120
gtggaccacg aagagttaac ccgggacttg gagaagcact gcagagacat ggaagaggcg    180
agccagcgca agtggaattt cgattttcag aatcacaaac ccctagaggg caagtacgag    240 tgcaagagg tggagaaggg cagcttgccc gagttctact acagaccccc gcggcccccc    300
aaaggtgcct gcaaggtgcc ggcgcaggag agccaggatg tcagcgggag ccgcccggcg    360 gcgccttta ttggggctcc ggctaactct gaggacacgc atttggtgga cccaaagact    420
gatccgtcgg acagccagac ggggttagcg gagcaatgcg caggaataag gaagcgacct    480
gcaaccgacg attcttctac tcaaaacaaa agagccaaca gaacagaaga aaatgtttca    540
gacggttagg cggccgc                                                   557
```

<210> SEQ ID NO 12
<211> LENGTH: 177
<212> TYPE: PRT
<213> ORGANISM: Homo sapiens

<400> SEQUENCE: 12

```
Met Gly Tyr Pro Tyr Asp Val Pro Asp Tyr Ala Ser Leu Glu Arg Met
 1               5                  10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly
```

<210> SEQ ID NO 13
<211> LENGTH: 1073
<212> TYPE: DNA
<213> ORGANISM: Homo sapiens

<400> SEQUENCE: 13

```
gaattcgccg ccaccatggg atacccttat gatgtgccag attatgccag cctggagcgg     60
atggacgcca ggcaggcgga gcaccccaag ccctcggcct gcaggaacct cttcggcccg    120
gtggaccacg aagagttaac ccgggacttg gagaagcact gcagagacat ggaagaggcg    180
agccagcgca agtggaattt cgattttcag aatcacaaac ccctagaggg caagtacgag    240
```

-continued

```
tggcaagagg tggagaaggg cagcttgccc gagttctact acagaccccc gcggccccc     300 aaaggtgcct gcaaggtgcc ggcgcaggag agccaggatg tcagcgggag ccgcccggcg     360
gcgcctttaa ttggggctcc ggctaactct gaggacacgc atttggtgga cccaaagact     420
gatccgtcgg acagccagac ggggttagcg gagcaatgcg caggaataag gaagcgacct     480
gcaaccgacg attcttctac tcaaaacaaa agagccaaca gaacagaaga aaatgtttca     540
gacggtggtg gcggggcag cggggtggc ggttccggcg ggggtggatc cgtcgaggat      600
ccggcggcgg ggagcagcat ggagccttcg gctgactggc tggccacggc gcggcccgg     660 ggtcgggtag aggaggtgcg ggcgctgctg gaggcggggg cgctgcccaa cgcaccgaat     720
agttacggtc ggaggccgat ccaggtcatg atgatgggca cgcccgagt ggcggagctg      780 ctgctgctcc acggcgcgga gcccaactgc gccgaccccg ccactctcac ccgacccgtg     840
cacgacgctg cccgggaggg cttcctggac acgctggtgg tgctgcaccg ggccggggcg     900
cggctggacg tgcgcgatgc ctgggccgt ctgcccgtgg acctggctga ggagctgggc      960
catcgcgatg tcgcacggta cctgcgcgcg ctgcggggg gcaccagagg cagtaaccat     1020
gcccgcatag atgccgcgga aggtccctca gacatccccg attgagcggc cgc            1073
```

<210> SEQ ID NO 14
<211> LENGTH: 348
<212> TYPE: PRT
<213> ORGANISM: Homo sapiens

<400> SEQUENCE: 14

```
Met Gly Tyr Pro Tyr Asp Val Pro Asp Tyr Ala Ser Leu Glu Arg Met
  1               5                  10                  15

Asp Ala Arg Gln Ala Glu His Pro Lys Pro Ser Ala Cys Arg Asn Leu
             20                  25                  30

Phe Gly Pro Val Asp His Glu Glu Leu Thr Arg Asp Leu Glu Lys His
         35                  40                  45

Cys Arg Asp Met Glu Glu Ala Ser Gln Arg Lys Trp Asn Phe Asp Phe
     50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Arg Pro Pro Lys
                 85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Gly Gly Gly Gly Ser Gly Gly Gly Ser Gly Gly Gly Ser
            180                 185                 190

Val Glu Asp Pro Ala Ala Gly Ser Ser Met Glu Pro Ser Ala Asp Trp
        195                 200                 205

Leu Ala Thr Ala Ala Ala Arg Gly Arg Val Glu Val Arg Ala Leu
    210                 215                 220

Leu Glu Ala Gly Ala Leu Pro Asn Ala Pro Asn Ser Tyr Gly Arg Arg
```

```
                225                 230                 235                 240
Pro Ile Gln Val Met Met Met Gly Ser Ala Arg Val Ala Glu Leu Leu
                    245                 250                 255

Leu Leu His Gly Ala Glu Pro Asn Cys Ala Asp Pro Ala Thr Leu Thr
            260                 265                 270

Arg Pro Val His Asp Ala Ala Arg Glu Gly Phe Leu Asp Thr Leu Val
        275                 280                 285

Val Leu His Arg Ala Gly Ala Arg Leu Asp Val Arg Asp Ala Trp Gly
    290                 295                 300

Leu Pro Val Asp Leu Ala Glu Glu Leu Gly His Arg Asp Val Ala Arg
305                 310                 315                 320

Tyr Leu Arg Ala Ala Ala Gly Gly Thr Arg Gly Ser Asn His Ala Arg
                325                 330                 335

Ile Asp Ala Ala Glu Gly Pro Ser Asp Ile Pro Asp
                340                 345
```

<210> SEQ ID NO 15
<211> LENGTH: 1028
<212> TYPE: DNA
<213> ORGANISM: Homo sapiens

<400> SEQUENCE: 15

```
gaattcgccg ccaccatggg ataccettat gatgtgccag attatgccag cctggagcgg      60
atggacgcca ggcaggcgga gcaccccaag ccctcggcct gcaggaacct cttcggcccg     120
gtggaccacg aagagttaac ccgggacttg agaagcact gcagagacat ggaagaggcg     180
agccagcgca gtggaatttt cgattttcag aatcacaaac ccctagaggg caagtacgag     240
tggcaagagg tggagaaggg cagcttgccc gagttctact acagaccccc gcggccccc      300
aaaggtgcct gcaaggtgcc ggcgcaggag agccaggatg tcagcgggag ccgcccggcg     360
gcgcctttaa ttgggctcc ggctaactct gaggacacgc atttggtgga cccaaagact      420
gatccgtcgg acagccagac gggttagcg gagcaatgcg caggaataag gaagcgacct      480
gcaaccgacg attcttctac tcaaaacaaa agagccaaca gaacagaaga aaatgtttca     540
gacggtgtcg aggatccggc ggcgggagc agcatggagc cttcggctga ctggctggcc      600
acggccgcgg cccggggtcg ggtagaggag gtgcgggcgc tgctggaggc gggggcgctg     660
cccaacgcac cgaatagtta cggtcggagg ccgatccagg tcatgatgat gggcagcgcc     720
cgagtggcgg agctgctgct gctccacggc gcggagccca actgcgccga ccccgccact     780
ctcacccgac ccgtgcacga cgctgcccgg gagggcttcc tggacacgct ggtggtgctg     840
caccgggccg gggcgcggct ggacgtgcgc gatgcctggg gccgtctgcc cgtggacctg     900
gctgaggagc tgggccatcg cgatgtcgca cggtacctgc gcgcggctgc ggggggcacc     960
agaggcagta accatgcccg catagatgcc gcggaaggtc cctcagacat ccccgattga    1020
gcggccgc                                                             1028
```

<210> SEQ ID NO 16
<211> LENGTH: 334
<212> TYPE: PRT
<213> ORGANISM: Homo sapiens

<400> SEQUENCE: 16

```
Met Gly Tyr Pro Tyr Asp Val Pro Asp Tyr Ala Ser Leu Glu Arg Met
  1               5                  10                  15

Asp Ala Arg Gln Ala Glu His Pro Lys Pro Ser Ala Cys Arg Asn Leu
```

```
                      20                      25                      30
        Phe Gly Pro Val Asp His Glu Glu Leu Thr Arg Asp Leu Glu Lys His
                     35                      40                      45
        Cys Arg Asp Met Glu Glu Ala Ser Gln Arg Lys Trp Asn Phe Asp Phe
         50                      55                      60
        Gln Asn His Lys Pro Leu Glu Gly Lys Tyr Glu Trp Gln Glu Val Glu
         65                      70                      75                      80
        Lys Gly Ser Leu Pro Glu Phe Tyr Tyr Arg Pro Arg Pro Pro Lys
                             85                      90                      95
        Gly Ala Cys Lys Val Pro Ala Gln Glu Ser Gln Asp Val Ser Gly Ser
                            100                     105                     110
        Arg Pro Ala Ala Pro Leu Ile Gly Ala Pro Ala Asn Ser Glu Asp Thr
                            115                     120                     125
        His Leu Val Asp Pro Lys Thr Asp Pro Ser Asp Ser Gln Thr Gly Leu
                            130                     135                     140
        Ala Glu Gln Cys Ala Gly Ile Arg Lys Arg Pro Ala Thr Asp Asp Ser
        145                     150                     155                     160
        Ser Thr Gln Asn Lys Arg Ala Asn Arg Thr Glu Glu Asn Val Ser Asp
                            165                     170                     175
        Gly Val Glu Asp Pro Ala Ala Gly Ser Ser Met Glu Pro Ser Ala Asp
                            180                     185                     190
        Trp Leu Ala Thr Ala Ala Arg Gly Arg Val Glu Glu Val Arg Ala
                            195                     200                     205
        Leu Leu Glu Ala Gly Ala Leu Pro Asn Ala Pro Asn Ser Tyr Gly Arg
                            210                     215                     220
        Arg Pro Ile Gln Val Met Met Met Gly Ser Ala Arg Val Ala Glu Leu
        225                     230                     235                     240
        Leu Leu Leu His Gly Ala Glu Pro Asn Cys Ala Asp Pro Ala Thr Leu
                            245                     250                     255
        Thr Arg Pro Val His Asp Ala Ala Arg Glu Gly Phe Leu Asp Thr Leu
                            260                     265                     270
        Val Val Leu His Arg Ala Gly Ala Arg Leu Asp Val Arg Asp Ala Trp
                            275                     280                     285
        Gly Arg Leu Pro Val Asp Leu Ala Glu Glu Leu Gly His Arg Asp Val
                            290                     295                     300
        Ala Arg Tyr Leu Arg Ala Ala Ala Gly Gly Thr Arg Gly Ser Asn His
        305                     310                     315                     320
        Ala Arg Ile Asp Ala Ala Glu Gly Pro Ser Asp Ile Pro Asp
                            325                     330

<210> SEQ ID NO 17
<211> LENGTH: 266
<212> TYPE: DNA
<213> ORGANISM: Homo sapiens

<400> SEQUENCE: 17
gaattcgccg ccaccatggg ataccttat gatgtgccag attatgccaa gccctcggcc        60
tgcaggaacc tcttcggccc ggtggaccac gaagagttaa cccgggactt ggagaagcac      120
tgcagagaca tggaagaggc gagccagcgc aagtggaatt tcgattttca gaatcacaaa      180 ccctagagg gcaagtacga gtggcaagag gtggagaagg gcagcttgcc cgagttctac      240
tacagacccc gcggtaggc ggccgc                                            266

<210> SEQ ID NO 18
```

```
<211> LENGTH: 80
<212> TYPE: PRT
<213> ORGANISM: Homo sapiens

<400> SEQUENCE: 18

Met Gly Tyr Pro Tyr Asp Val Pro Asp Tyr Ala Lys Pro Ser Ala Cys
 1               5                  10                  15

Arg Asn Leu Phe Gly Pro Val Asp His Glu Glu Leu Thr Arg Asp Leu
             20                  25                  30

Glu Lys His Cys Arg Asp Met Glu Glu Ala Ser Gln Arg Lys Trp Asn
         35                  40                  45

Phe Asp Phe Gln Asn His Lys Pro Leu Glu Gly Lys Tyr Glu Trp Gln
     50                  55                  60

Glu Val Glu Lys Gly Ser Leu Pro Glu Phe Tyr Tyr Arg Pro Pro Arg
 65                  70                  75                  80

<210> SEQ ID NO 19
<211> LENGTH: 737
<212> TYPE: DNA
<213> ORGANISM: Homo sapiens

<400> SEQUENCE: 19
gaattcgccg ccaccatggg atacccttat gatgtgccag attatgccaa gccctcggcc    60
tgcaggaacc tcttcggccc ggtggaccac gaagagttaa cccgggactt ggagaagcac   120
tgcagagaca tggaagaggc gagccagcgc aagtggaatt tcgattttca gaatcacaaa   180
cccctagagg gcaagtacga gtggcaagag gtggagaagg gcagcttgcc cgagttctac   240
tacagacccc cgcgggtcga ggatccggcg cgggggagca gcatggagcc ttcggctgac   300
tggctggcca cggccgcggc ccggggtcgg gtagaggagg tgcgggcgct gctggaggcg   360
ggggcgctgc ccaacgcacc gaatagttac ggtcggaggc cgatccaggt catgatgatg   420
ggcagcgccc gagtggcgga gctgctgctg ctccacggcg cggagcccaa ctgcgccgac   480
cccgccactc tcacccgacc cgtgcacgac gctgcccggg agggcttcct ggacacgcta   540
gtggtgctgc accgggccgg ggcgcggctg acgtgcgcg atgcctgggg ccgtctgccc   600
gtggacctgg ctgaggagct gggccatcgc gatgtcgcac ggtacctgcg cgcggctgcg   660
gggggcacca gaggcagtaa ccatgcccgc atagatgccg cggaaggtcc ctcagacatc   720
cccgattgag cggccgc                                                  737

<210> SEQ ID NO 20
<211> LENGTH: 237
<212> TYPE: PRT
<213> ORGANISM: Homo sapiens

<400> SEQUENCE: 20

Met Gly Tyr Pro Tyr Asp Val Pro Asp Tyr Ala Lys Pro Ser Ala Cys
 1               5                  10                  15

Arg Asn Leu Phe Gly Pro Val Asp His Glu Glu Leu Thr Arg Asp Leu
             20                  25                  30

Glu Lys His Cys Arg Asp Met Glu Glu Ala Ser Gln Arg Lys Trp Asn
         35                  40                  45

Phe Asp Phe Gln Asn His Lys Pro Leu Glu Gly Lys Tyr Glu Trp Gln
     50                  55                  60

Glu Val Glu Lys Gly Ser Leu Pro Glu Phe Tyr Tyr Arg Pro Pro Arg
 65                  70                  75                  80

Val Glu Asp Pro Ala Ala Gly Ser Ser Met Glu Pro Ser Ala Asp Trp
```

```
                        85                 90                      95
Leu Ala Thr Ala Ala Arg Gly Arg Val Glu Val Arg Ala Leu
                100                 105                 110
Leu Glu Ala Gly Ala Leu Pro Asn Ala Pro Asn Ser Tyr Gly Arg Arg
            115                 120                 125
Pro Ile Gln Val Met Met Met Gly Ser Ala Arg Val Ala Glu Leu Leu
    130                 135                 140
Leu Leu His Gly Ala Glu Pro Asn Cys Ala Asp Pro Ala Thr Leu Thr
145                 150                 155                 160
Arg Pro Val His Asp Ala Ala Arg Glu Gly Phe Leu Asp Thr Leu Val
                165                 170                 175
Val Leu His Arg Ala Gly Ala Arg Leu Asp Val Arg Asp Ala Trp Gly
                180                 185                 190
Arg Leu Pro Val Asp Leu Ala Glu Glu Leu Gly His Arg Asp Val Ala
            195                 200                 205
Arg Tyr Leu Arg Ala Ala Ala Gly Gly Thr Arg Gly Ser Asn His Ala
        210                 215                 220
Arg Ile Asp Ala Ala Glu Gly Pro Ser Asp Ile Pro Asp
225                 230                 235
```

<210> SEQ ID NO 21
<211> LENGTH: 782
<212> TYPE: DNA
<213> ORGANISM: Homo sapiens

<400> SEQUENCE: 21

```
gaattcgccg ccaccatggg atacccttat gatgtgccag attatgccaa gccctcggcc      60
tgcaggaacc tcttcggccc ggtggaccac gaagagttaa cccgggactt ggagaagcac     120
tgcagagaca tggaagaggc gagccagcgc aagtggaatt tcgattttca gaatcacaaa     180
cccctagagg gcaagtacga gtggcaagag gtggagaagg gcagcttgcc cgagttctac     240
tacagacccc gcggggtgg cggggcagc ggggtggcg gttccggcgg ggtggatcc         300
gtcgaggatc cggcggcggg gagcagcatg gagccttcgg ctgactggct ggccacggcc     360
gcggcccggg gtcgggtaga ggaggtgcgg gcgctgctgg aggcgggggc gctgcccaac     420
gcaccgaata gttacggtcg gaggccgatc caggtcatga tgatgggcag cgcccgagtg     480
gcggagctgc tgctgctcca cggcgcggag cccaactgcg ccgaccccgc cactctcacc     540
cgacccgtgc acgacgctgc ccgggagggc ttcctggaca cgctggtggt gctgcaccgg     600
gccgggcgc ggctggacgt gcgcgatgcc tggggccgtc tgcccgtgga cctggctgag     660
gagctgggcc atcgcgatgt cgcacggtac ctgcgcgcg ctgcgggggg caccagaggc     720
agtaaccatg cccgcataga tgccgcggaa ggtccctcag acatccccga ttgagcggcc     780
gc                                                                    782
```

<210> SEQ ID NO 22
<211> LENGTH: 252
<212> TYPE: PRT
<213> ORGANISM: Homo sapiens

<400> SEQUENCE: 22

```
Met Gly Tyr Pro Tyr Asp Val Pro Asp Tyr Ala Lys Pro Ser Ala Cys
 1               5                  10                  15
Arg Asn Leu Phe Gly Pro Val Asp His Glu Glu Leu Thr Arg Asp Leu
            20                  25                  30
```

-continued

```
Glu Lys His Cys Arg Asp Met Glu Glu Ala Ser Gln Arg Lys Trp Asn
            35                  40                  45

Phe Asp Phe Gln Asn His Lys Pro Leu Glu Gly Lys Tyr Glu Trp Gln
 50                  55                  60

Glu Val Glu Lys Gly Ser Leu Pro Glu Phe Tyr Tyr Arg Pro Pro Arg
 65                  70                  75                  80

Gly Gly Gly Gly Ser Gly Gly Gly Ser Gly Gly Gly Ser Val
                85                  90                  95

Glu Asp Pro Ala Ala Gly Ser Ser Met Glu Pro Ser Ala Asp Trp Leu
            100                 105                 110

Ala Thr Ala Ala Ala Arg Gly Arg Val Glu Val Arg Ala Leu Leu
            115                 120                 125

Glu Ala Gly Ala Leu Pro Asn Ala Pro Asn Ser Tyr Gly Arg Arg Pro
 130                 135                 140

Ile Gln Val Met Met Met Gly Ser Ala Arg Val Ala Glu Leu Leu Leu
145                 150                 155                 160

Leu His Gly Ala Glu Pro Asn Cys Ala Asp Pro Ala Thr Leu Thr Arg
            165                 170                 175

Pro Val His Asp Ala Ala Arg Glu Gly Phe Leu Asp Thr Leu Val Val
            180                 185                 190

Leu His Arg Ala Gly Ala Arg Leu Asp Val Arg Asp Ala Trp Gly Arg
            195                 200                 205

Leu Pro Val Asp Leu Ala Glu Glu Leu Gly His Arg Asp Val Ala Arg
 210                 215                 220

Tyr Leu Arg Ala Ala Gly Gly Thr Arg Gly Ser Asn His Ala Arg
225                 230                 235                 240

Ile Asp Ala Ala Glu Gly Pro Ser Asp Ile Pro Asp
            245                 250
```

<210> SEQ ID NO 23
<211> LENGTH: 687
<212> TYPE: DNA
<213> ORGANISM: Homo sapiens

<400> SEQUENCE: 23

```
atggccaagc cctcggcctg caggaacctc ttcggcccgg tggaccacga agagttaacc    60
cgggacttgg agaagcactg cagagacatg gaagaggcga gccagcgcaa gtggaatttc   120
gattttcaga atcacaaacc cctagagggc aagtacgagt ggcaagaggt ggagaagggc   180
agcttgcccg agttctacta cagacccccg cgggtcgagg atccggcggc ggggagcagc   240
atggagcctt cggctgactg gctggccacg gccgcggccc gggtcgggt agaggaggtg    300
cgggcgctgc tggaggcggg ggcgctgccc aacgcaccga atagttacgg tcggaggccg   360
atccaggtca tgatgatggg cagcgcccga gtggcggagc tgctgctgct ccacggcgcg   420
gagcccaact gcgccgaccc cgccactctc acccgacccg tgcacgacgc tgcccgggag   480
ggcttcctgg acacgctggt ggtgctgcac cgggccgggg cgcggctgga cgtgcgcgat   540
gcctggggcc gtctgcccgt ggacctggct gaggagctgg gccatcgcga tgtcgcacgg   600
tacctgcgcg cggctgcggg gggcaccaga ggcagtaacc atgcccgcat agatgccgcg   660
gaaggtccct cagacatccc cgattga                                       687
```

<210> SEQ ID NO 24
<211> LENGTH: 228
<212> TYPE: PRT
<213> ORGANISM: Homo sapiens

<400> SEQUENCE: 24

```
Met Ala Lys Pro Ser Ala Cys Arg Asn Leu Phe Gly Pro Val Asp His
  1               5                  10                  15
Glu Glu Leu Thr Arg Asp Leu Glu Lys His Cys Arg Asp Met Glu Glu
                 20                  25                  30
Ala Ser Gln Arg Lys Trp Asn Phe Asp Phe Gln Asn His Lys Pro Leu
             35                  40                  45
Glu Gly Lys Tyr Glu Trp Gln Glu Val Glu Lys Gly Ser Leu Pro Glu
         50                  55                  60
Phe Tyr Tyr Arg Pro Pro Arg Val Glu Asp Pro Ala Ala Gly Ser Ser
 65                  70                  75                  80
Met Glu Pro Ser Ala Asp Trp Leu Ala Thr Ala Ala Ala Arg Gly Arg
                 85                  90                  95
Val Glu Glu Val Arg Ala Leu Leu Glu Ala Gly Ala Leu Pro Asn Ala
                100                 105                 110
Pro Asn Ser Tyr Gly Arg Arg Pro Ile Gln Val Met Met Met Gly Ser
            115                 120                 125
Ala Arg Val Ala Glu Leu Leu Leu Leu His Gly Ala Glu Pro Asn Cys
130                 135                 140
Ala Asp Pro Ala Thr Leu Thr Arg Pro Val His Asp Ala Ala Arg Glu
145                 150                 155                 160
Gly Phe Leu Asp Thr Leu Val Val Leu His Arg Ala Gly Ala Arg Leu
                165                 170                 175
Asp Val Arg Asp Ala Trp Gly Arg Leu Pro Val Asp Leu Ala Glu Glu
                180                 185                 190
Leu Gly His Arg Asp Val Ala Arg Tyr Leu Arg Ala Ala Ala Gly Gly
            195                 200                 205
Thr Arg Gly Ser Asn His Ala Arg Ile Asp Ala Ala Glu Gly Pro Ser
        210                 215                 220
Asp Ile Pro Asp
225
```

<210> SEQ ID NO 25
<211> LENGTH: 597
<212> TYPE: DNA
<213> ORGANISM: Homo sapiens

<400> SEQUENCE: 25

```
atgtcaaacg tgcgagtgtc taacgggagc cctagcctgg agcggatgga cgccaggcag    60
gcggagcacc ccaagccctc ggcctgcagg aacctcttcg gccggtgga ccacgaagag   120
ttaacccggg acttggagaa gcactgcaga gacatggaag aggcgagcca gcgcaagtgg   180
aatttcgatt ttcagaatca caaaccccta gagggcaagt acgagtggca agaggtggag   240
aagggcagct tgcccgagtt ctactacaga ccccgcggc ccccaaagg tgcctgcaag   300
gtgccggcgc aggagagcca ggatgtcagc gggagccgcc cggcggcgcc tttaattggg   360
gctccggcta actctgagga cacgcatttg gtggacccaa agactgatcc gtcggacagc   420
cagacggggt tagcggagca atgcgcagga ataaggaagc gacctgcaac cgacgattct   480
tctactcaaa acaaaagagc caacagaaca gaagaaaatg tttcagacgg ttccccaaat   540
gccggttctg tggagcagac gcccaagaag cctggcctca agacgtca aacgtaa    597
```

<210> SEQ ID NO 26
<211> LENGTH: 198

<210> SEQ ID NO 26
<211> LENGTH: 197 (inferred)
<212> TYPE: PRT
<213> ORGANISM: Homo sapiens

<400> SEQUENCE: 26

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 27
<211> LENGTH: 987
<212> TYPE: DNA
<213> ORGANISM: Homo sapiens

<400> SEQUENCE: 27
cggagagggg gagaacagac aacgggcggc ggggagcagc atggagccgg cggcggggag      60
cagcatggag ccttcggctg actggctggc cacggccgcg gcccggggtc gggtagagga     120
ggtgcgggcg ctgctggagg cggggggcgct gcccaacgca ccgaatagtt acggtcggag     180
gccgatccag gtcatgatga tgggcagcgc ccgagtggcg gagctgctgc tgctccacgg     240
cgcggagccc aactgcgccg accccgccac tctcacccga cccgtgcacg acgctgcccg     300
ggagggcttc ctggacacgc tggtggtgct gcaccgggcc ggggcgcggc tggacgtgcg     360
cgatgcctgg ggccgtctgc ccgtggacct ggctgaggag ctgggccatc gcgatgtcgc     420
acggtacctg cgcgcggctg cgggggggcac cagaggcagt aaccatgccc gcatagatgc     480
cgcggaaggt ccctcagaca tccccgattg aaagaaccag agaggctctg agaaacctcg     540
ggaaacttag atcatcagtc accgaaggtc ctacagggcc acaactgccc cgccacaac      600 ccaccccgct ttcgtagttt tcatttagaa aatagagctt ttaaaaatgt cctgccttttt    660 aacgtagata taagccttcc cccactaccg taaatgtcca tttatatcat tttttatata     720
ttcttataaa aatgtaaaaa agaaaaacac cgcttctgcc ttttcactgt gttggagttt    780
tctggagtga gcactcacgc cctaagcgca cattcatgtg ggcatttctt gcgagcctcg     840

-continued

```
cagcctccgg aagctgtcga cttcatgaca agcattttgt gaactaggga agctcagggg    900
ggttactggc ttctcttgag tcacactgct agcaaatggc agaaccaaag ctcaaataaa    960
aataaaataa ttttcattca ttcactc                                        987
```

<210> SEQ ID NO 28
<211> LENGTH: 156
<212> TYPE: PRT
<213> ORGANISM: Homo sapiens

<400> SEQUENCE: 28

```
Met Glu Pro Ala Ala Gly Ser Ser Met Glu Pro Ser Ala Asp Trp Leu
  1               5                  10                  15

Ala Thr Ala Ala Ala Arg Gly Arg Val Glu Val Arg Ala Leu Leu
                 20                  25                  30

Glu Ala Gly Ala Leu Pro Asn Ala Pro Asn Ser Tyr Gly Arg Arg Pro
             35                  40                  45

Ile Gln Val Met Met Met Gly Ser Ala Arg Val Ala Glu Leu Leu Leu
 50                  55                  60

Leu His Gly Ala Glu Pro Asn Cys Ala Asp Pro Ala Thr Leu Thr Arg
 65                  70                  75                  80

Pro Val His Asp Ala Ala Arg Glu Gly Phe Leu Asp Thr Leu Val Val
                 85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
        130                 135                 140

Ile Asp Ala Ala Glu Gly Pro Ser Asp Ile Pro Asp
145                 150                 155
```

<210> SEQ ID NO 29
<211> LENGTH: 972
<212> TYPE: DNA
<213> ORGANISM: Homo sapiens

<400> SEQUENCE: 29

```
atggccctgt ggatgcgcct cctgccctg ctggcgctgc tggccctctg gggacctgac     60
ccagccgcag ccatggagct ggtagatcct aacctagagc cttggaatca tccggggagt    120
cagcctacga ctgcttgtag caagtgttac tgtaaaaaat gttgctggca ttgccaacta    180
tgctttctga aaaaggctt aggcatctcc catggcagga agaagcggaa gcaccgacga    240
agaactcctc agagcagtaa agatcatcaa tatcctatac cagagcaagc caagccctcg    300
gcctgcagga acctcttcgg cccggtggac acgaagagt taacccggga cttggagaag    360
cactgcagag acatggaaga ggcgagccag cgcaagtgga atttcgattt tcagaatcac    420 aaaccctag agggcaagta cgagtggcaa gaggtggaga agggcagctt gccgagttc    480 tactacagac ccccgcgggt cgaggatccg gcggcgggga gcagcatgga gccttcggct    540
gactggctgg ccacgccgc ggcccggggt cgggtagagg aggtgcgggc gctgctggag    600 gcggggcgc tgcccaacgc accgaatagt tacggtcgga ggccgatcca ggtcatgatg    660 atggcagcg cccgagtggc ggagctgctg ctgctccacg gcgcggagcc caactgcgcc    720
gaccccgcca ctctcacccg accgtgcac gacgctgccc gggagggctt cctggacacg    780
```

```
ctggtggtgc tgcaccgggc cggggcgcgg ctggacgtgc gcgatgcctg gggccgtctg     840
cccgtggacc tggctgagga gctgggccat cgcgatgtcg cacggtacct gcgcgcggct     900
gcgggggcca ccagaggcag taaccatgcc cgcatagatg ccgcggaagg tccctcagac     960
atccccgatt ga                                                         972
```

<210> SEQ ID NO 30
<211> LENGTH: 323
<212> TYPE: PRT
<213> ORGANISM: Homo sapiens

<400> SEQUENCE: 30

```
Met Ala Leu Trp Met Arg Leu Leu Pro Leu Leu Ala Leu Leu Ala Leu
 1               5                  10                  15

Trp Gly Pro Asp Pro Ala Ala Ala Met Glu Leu Val Asp Pro Asn Leu
            20                  25                  30

Glu Pro Trp Asn His Pro Gly Ser Gln Pro Thr Thr Ala Cys Ser Lys
        35                  40                  45

Cys Tyr Cys Lys Lys Cys Cys Trp His Cys Gln Leu Cys Phe Leu Lys
    50                  55                  60

Lys Gly Leu Gly Ile Ser His Gly Arg Lys Arg Lys His Arg Arg
65                  70                  75                  80

Arg Thr Pro Gln Ser Ser Lys Asp His Gln Tyr Pro Ile Pro Glu Gln
                85                  90                  95

Ala Lys Pro Ser Ala Cys Arg Asn Leu Phe Gly Pro Val Asp His Glu
            100                 105                 110

Glu Leu Thr Arg Asp Leu Glu Lys His Cys Arg Asp Met Glu Glu Ala
        115                 120                 125

Ser Gln Arg Lys Trp Asn Phe Asp Phe Gln Asn His Lys Pro Leu Glu
    130                 135                 140

Gly Lys Tyr Glu Trp Gln Glu Val Glu Lys Gly Ser Leu Pro Glu Phe
145                 150                 155                 160

Tyr Tyr Arg Pro Pro Arg Val Glu Asp Pro Ala Ala Gly Ser Ser Met
                165                 170                 175

Glu Pro Ser Ala Asp Trp Leu Ala Thr Ala Ala Ala Arg Gly Arg Val
            180                 185                 190

Glu Glu Val Arg Ala Leu Leu Glu Ala Gly Ala Leu Pro Asn Ala Pro
        195                 200                 205

Asn Ser Tyr Gly Arg Arg Pro Ile Gln Val Met Met Met Gly Ser Ala
    210                 215                 220

Arg Val Ala Glu Leu Leu Leu Leu His Gly Ala Glu Pro Asn Cys Ala
225                 230                 235                 240

Asp Pro Ala Thr Leu Thr Arg Pro Val His Asp Ala Ala Arg Glu Gly
                245                 250                 255

Phe Leu Asp Thr Leu Val Val Leu His Arg Ala Gly Ala Arg Leu Asp
            260                 265                 270

Val Arg Asp Ala Trp Gly Arg Leu Pro Val Asp Leu Ala Glu Glu Leu
        275                 280                 285

Gly His Arg Asp Val Ala Arg Tyr Leu Arg Ala Ala Gly Gly Thr
    290                 295                 300

Arg Gly Ser Asn His Ala Arg Ile Asp Ala Ala Glu Gly Pro Ser Asp
305                 310                 315                 320

Ile Pro Asp
```

```
<210> SEQ ID NO 31
<211> LENGTH: 1017
<212> TYPE: DNA
<213> ORGANISM: Homo sapiens

<400> SEQUENCE: 31
atggccctgt ggatgcgcct cctgcccctg ctggcgctgc tggccctctg gggacctgac      60
ccagccgcag ccatggagct ggtagatcct aacctagagc cttggaatca tccggggagt     120
cagcctacga ctgcttgtag caagtgttac tgtaaaaaat gttgctggca ttgccaacta     180
tgctttctga aaaaaggctt aggcatctcc catggcagga gaagcggaa gcaccgacga     240
agaactcctc agagcagtaa agatcatcaa tatcctatac cagagcaagg tggcgggggc     300
agcgggggtg gcggttccgg cggggtgga tccgccaagc cctcggcctg caggaacctc     360
ttcggcccgg tggaccacga agagttaacc cgggacttgg agaagcactg cagagacatg     420
gaagaggcga gccagcgcaa gtggaatttc gattttcaga atcacaaacc cctagagggc     480
aagtacgagt ggcaagaggt ggagaagggc agcttgcccg agttctacta cagacccccg     540
cgggtcgagg atccggcggc ggggagcagc atggagcctt cggctgactg gctggccacg     600
gccgcggccc ggggtcgggt agaggaggtg cgggcgctgc tggaggcggg ggcgctgccc     660
aacgcaccga atagttacgg tcggaggccg atccaggtca tgatgatggg cagcgcccga     720
gtggcggagc tgctgctgct ccacggcgcg gagcccaact gcgccgaccc cgccactctc     780
acccgacccg tgcacgacgc tgcccgggag ggcttcctgg acacgctggt ggtgctgcac     840
cgggccgggg cgcggctgga cgtgcgcgat gcctggggcc gtctgcccgt ggacctggct     900
gaggagctgg ccatcgcga tgtcgcacgg tacctgcgcg cggctgcggg gggcaccaga     960
ggcagtaacc atgcccgcat agatgccgcg gaaggtccct cagacatccc cgattga     1017

<210> SEQ ID NO 32
<211> LENGTH: 337
<212> TYPE: PRT
<213> ORGANISM: Homo sapiens

<400> SEQUENCE: 32

Met Ala Leu Trp Met Arg Leu Leu Pro Leu Leu Ala Leu Leu Ala Leu
 1               5                  10                  15

Trp Gly Pro Asp Pro Ala Ala Ala Met Glu Leu Val Asp Pro Asn Leu
                20                  25                  30

Glu Pro Trp Asn His Pro Gly Ser Gln Pro Thr Thr Ala Cys Ser Lys
            35                  40                  45

Cys Tyr Cys Lys Lys Cys Cys Trp His Cys Gln Leu Cys Phe Leu Lys
        50                  55                  60

Lys Gly Leu Gly Ile Ser His Gly Arg Lys Arg Lys His Arg Arg
 65                  70                  75                  80

Arg Thr Pro Gln Ser Ser Lys Asp His Gln Tyr Pro Ile Pro Glu Gln
                85                  90                  95

Gly Gly Gly Gly Ser Gly Gly Gly Ser Gly Gly Gly Ser Ala
                100                 105                 110

Lys Pro Ser Ala Cys Arg Asn Leu Phe Gly Pro Val Asp His Glu Glu
            115                 120                 125

Leu Thr Arg Asp Leu Glu Lys His Cys Arg Asp Met Glu Glu Ala Ser
        130                 135                 140

Gln Arg Lys Trp Asn Phe Asp Phe Gln Asn His Lys Pro Leu Glu Gly
145                 150                 155                 160
```

-continued

```
Lys Tyr Glu Trp Gln Glu Val Glu Lys Gly Ser Leu Pro Glu Phe Tyr
            165                 170                 175

Tyr Arg Pro Pro Arg Val Glu Asp Pro Ala Ala Gly Ser Ser Met Glu
            180                 185                 190

Pro Ser Ala Asp Trp Leu Ala Thr Ala Ala Arg Gly Arg Val Glu
        195                 200                 205

Glu Val Arg Ala Leu Leu Glu Ala Gly Ala Leu Pro Asn Ala Pro Asn
        210                 215                 220

Ser Tyr Gly Arg Arg Pro Ile Gln Val Met Met Met Gly Ser Ala Arg
225                 230                 235                 240

Val Ala Glu Leu Leu Leu Leu His Gly Ala Glu Pro Asn Cys Ala Asp
                245                 250                 255

Pro Ala Thr Leu Thr Arg Pro Val His Asp Ala Ala Arg Glu Gly Phe
                260                 265                 270

Leu Asp Thr Leu Val Val Leu His Arg Ala Gly Ala Arg Leu Asp Val
            275                 280                 285

Arg Asp Ala Trp Gly Arg Leu Pro Val Asp Leu Ala Glu Glu Leu Gly
        290                 295                 300

His Arg Asp Val Ala Arg Tyr Leu Arg Ala Ala Ala Gly Gly Thr Arg
305                 310                 315                 320

Gly Ser Asn His Ala Arg Ile Asp Ala Ala Glu Gly Pro Ser Asp Ile
                325                 330                 335

Pro
```